US012522870B2

(12) United States Patent
Zhou et al.

(10) Patent No.: US 12,522,870 B2
(45) Date of Patent: Jan. 13, 2026

(54) OLIGONUCLEOTIDE-TEMPLATED PHOTOREDUCTION FLUOROGENIC PROBE PAIRS AND THEIR USE IN QUANTITATIVE DETECTION OF TARGET RNA SEQUENCES

(71) Applicant: Jan Biotech, Inc., Ithaca, NY (US)

(72) Inventors: Can Zhou, Ithaca, NY (US); Janet Lockwood Huie, Ithaca, NY (US); Jennifer Anastasia Nichols, Ithaca, NY (US)

(73) Assignee: Jan Biotech, Inc., Ithaca, NY (US)

( * ) Notice: Subject to any disclaimer, the term of this patent is extended or adjusted under 35 U.S.C. 154(b) by 1160 days.

(21) Appl. No.: 17/209,381

(22) Filed: Mar. 23, 2021

(65) Prior Publication Data

US 2022/0127670 A1 Apr. 28, 2022

Related U.S. Application Data

(60) Provisional application No. 62/994,115, filed on Mar. 24, 2020.

(51) Int. Cl.

| | |
|---|---|
| ***C12Q 1/68*** | (2018.01) |
| ***C12Q 1/6816*** | (2018.01) |
| ***C12Q 1/6876*** | (2018.01) |
| ***C12Q 1/70*** | (2006.01) |

(52) U.S. Cl.

CPC ......... *C12Q 1/6876* (2013.01); *C12Q 1/6816* (2013.01); *C12Q 1/70* (2013.01); *C12Q 1/703* (2013.01); *G01N 2333/08* (2013.01)

(58) Field of Classification Search

CPC .... C12Q 1/6876; C12Q 1/6816; C12Q 1/703; G01N 2333/08

See application file for complete search history.

(56) References Cited

U.S. PATENT DOCUMENTS

2018/0002743 A1* 1/2018 Huie ...................... C12Q 1/703

FOREIGN PATENT DOCUMENTS

WO WO-2018069470 A1 * 4/2018 ........... C07D 401/12

OTHER PUBLICATIONS

Beatty et al., "Amine Functionalization via Oxidative Photoredox Catalysis: Methodology Development and Complex Molecule Synthesis," American Chemical Society 48, pp. 1474-1484 (2015).
Chang et al., "Accelerating Turnover Frequency in Nucleic Acid Templated Re-actions," Bioconjugate Chem. 29, pp. 158-163, (2018).
Chang et al., "Accelerating Turnover Frequency in Nucleic Acid Templated Re-actions," Supporting Information, 49 pages (2018).
Chang et al., "Critical Analysis of Rate Constants and Turnover Frequency in Nucleic Acid-Templated Reactions: Reaching Terminal Velocity," Supporting Information, 39 pages (2017).
Chang et al., "Critical Analysis of Rate Constants and Turnover Frequency in Nucleic Acid-Templated Reactions: Reaching Terminal Velocity," J. Am. Chem. Soc., pp. 1-7 (2017).
Chen et al., "A Biomolecule-Compatible Visible Light-Induced Azide Reduction from a DNA-Encoded Reaction Discovery System," Nat Chem. 3(2), pp. 146-153 (2011).
Furukawa et al., "Reduction-Triggered Fluorescent Amplification Probe for the Detection of Endogenous RNAs in Living Human Cells," Bioconjugate Chem., 2009, 20, pp. 1026-1036.
Guerra et al., "Visible-light photoredox catalysis using a macromolecular ruthenium complex: reactivity and recovery by size-exclusion nanofiltration in continuous flow," Catalysis Science & Technology, 2016, 6, pp. 4695-4699.
Holtzer et al., "Nucleic-acid templated chemical reaction in a live vertebrate," American Chemical Society, 2016, 2, pp. 394-400.
Holtzer et al., "Nucleic-acid templated chemical reaction in a live vertebrate," Supplementary Information, 25 pages (2016).
Kaiser et al., "Assays for precise quantification of total (including short) and elongated HIV-1 transcripts," J Virol Methods, 2017, 242: pp. 1-20.
Lavis et al., "Latent Blue and Red Fluorophores Based on the Trimethyl Lock," Chem BioChem 7, pp. 1151-1154 (2006).
Prier et al., "Visible Light Photoredox Catalysis with Transition Metal Complexes: Applications in Organic Synthesis," Chem Rev. 113, pp. 5322-5363 (2013).
Röthlingshofer et al., "Nucleic Acid Templated Uncaging of Fluorophores Using Ru-Catalyzed Photoreduction with Visible Light," Organic Letters 14(2), pp. 482-485 (2012).
Röthlingshofer et al., "Nucleic Acid Templated Uncaging of Fluorophores Using Ru-Catalyzed Photoreduction with Visible Light," Supporting Information, 13 pages (2012).
Sadhu et al., "Detection of miRNA in Live Cells by Using Templated Rull-Catalyzed Unmasking of a Fluorophore," Chem. Eur. J. 19, pp. 8182-8189 (2013).

(Continued)

*Primary Examiner* — Jezia Riley
(74) *Attorney, Agent, or Firm* — McNeill PLLC

(57) ABSTRACT

This application describes a fluorogenic nucleic acid kit or composition for quantitative detection of a target ribonucleic acid (RNA) sequence in a test sample comprising at least one pair of oligonucleotide probes comprising a photocatalyst probe and a profluorophore probe, wherein one of the photocatalyst probe and the profluorophore probe is complementary to and capable of specifically binding an upstream portion of the target RNA sequence, and the other probe is complementary to and capable of specifically binding to a downstream portion of the target RNA sequence, the photocatalyst probe comprises a first oligonucleotide covalently bound to a photocatalyst, the profluorophore probe comprises a second oligonucleotide covalently bound to a profluorophore, and the photocatalyst is activatable by exposure to light and a reducing agent to form a reduced, activated photocatalyst that, when both probes of the pair are hybridized to the target RNA sequence, is capable of photoreducing the profluorophore to form a detectable fluorophore. The application also describes methods for quantitative detection of target RNA.

20 Claims, 27 Drawing Sheets

Specification includes a Sequence Listing.

(56) References Cited

OTHER PUBLICATIONS

Sadhu et al., "Detection of miRNA in Live Cells by Using Templated Rull-Catalyzed Unmasking of a Fluorophore," Supporting Information, 12 pages (2013).

Sigma-Aldrich "Bis(2,2'-bipyridine)-4'-methyl-4-carboxybipyridine-ruthenium N-succinimidyl esterbis (hexafluorophosphate)" https://www.sigmaaldrich.com/US/en/product/sigma/96631, 3 pages (2019).

* cited by examiner (M)

(N)

OLIGONUCLEOTIDE-TEMPLATED PHOTOREDUCTION FLUOROGENIC PROBE PAIRS AND THEIR USE IN QUANTITATIVE DETECTION OF TARGET RNA SEQUENCES

CROSS REFERENCE TO RELATED APPLICATIONS

This application claims priority to U.S. Provisional Application No. 62/994,115, filed on Mar. 24, 2020, the disclosure of which is hereby incorporated by reference in its entirety.

This invention was made with government support under R44AI116358 awarded by the National Institute of Allergy and Infectious Diseases of the National Institutes of Health. The government has certain rights in the invention.

FIELD

Novel compositions, reagents, methods, assays, and kits within the field of fluorogenic, nonenzymatic, quantitative detection, oligonucleotide-templated photoreduction (OTP) reactions, and their use in research, diagnostic, and clinical applications, to rapidly, precisely, accurately, and specifically quantitate low levels of target ribonucleic acid (RNA) sequences present in a test sample.

BACKGROUND

With the introduction of combination/highly active antiretroviral therapy (cART or HAART) in 1996, HIV-1 infection, properly controlled with frequent (often daily) medication, has become a chronic condition. However, due to the existence of latent pools of HIV-1 infected cells ("latent reservoirs," or "LR") in patients on cART/HAART, HIV-1 viral levels rebound for almost all infected individuals within 1-3 weeks after stopping treatment. Thus, HIV-1 infected individuals must commit to lifelong adherence to HAART regimens, with an estimated cost of over half a million dollars per individual. Significant government and industry resources have been deployed to generate a cure for HIV/AIDS. Formed in 1986, the National Institutes of Health Division of AIDS (DAIDS) was tasked with a national research agenda to end the HIV/AIDS epidemic. DAIDS supports a global research portfolio on HIV/AIDS, related co-infections, and co-morbidities. The goal is to create an AIDS-free generation through innovative approaches aimed at: 1) halting the spread of HIV-1 through effective and acceptable prevention strategies and a preventive vaccine; 2) treating and curing HIV-1 infection; 3) establishing treatment and prevention strategies for the HIV-1 co-infections and co-morbidities of greatest significance; and 4) partnering with scientific and community stakeholders to implement effective interventions. If a cure or remission therapy becomes available, it will transform the lives of HIV-1 infected individuals and the financial landscape of this devastating disease. The ability to measure low levels of HIV-1 precisely and accurately in latent reservoirs is a critical bottleneck in achieving a cure or longer-acting antiretroviral therapies for HIV/AIDS.

Latent reservoirs consist of resting or memory CD4+ cells and other cells carrying, for example, the HIV-1 viral genome, either as pre-integration plasmids or integrated into relatively inactive regions of the DNA of CD4+ and potentially other host cells, as well as HIV-1 infected cells in HAART-inaccessible regions of the body. HIV-1 latent reservoirs include peripheral blood, lymph nodes (B cell follicles), gut-associated lymphatic tissue (GALT), central nervous system (brain and spinal cord), and oral mucosa.

Resting memory CD4+ T cells, typically sampled from peripheral blood mononuclear cells (PBMC), are the most readily accessible component of the HIV-1 latent reservoir (LR). While a variety of culture- and PCR-based assays have been developed to measure the size of the LR in peripheral blood, there is little agreement between different assay results and no available assay appears to provide an accurate measurement of LR size. The lack of an accepted standard assay has remained a significant impediment in clinical trials seeking to evaluate novel HIV-1 eradication strategies. Well-validated, high-throughput assays that accurately quantitate the LR are urgently needed to assess complete eradication of HIV-1. Existing assays quantitate HIV TAR RNA but do not quantitate the HIV latent reservoir. Currently, there are no commercially or noncommercially available assays that adequately address this need and that can be translated to widespread use.

The oral mucosa is a HAART-resistant HIV-1 latent reservoir (LR), which, unlike systemic immunity, is not restored to full immune competence by HAART treatment. The oral mucosa LR appears to include not only the expected CD4+ T cells, but also dendritic cells, which are under constant reactivation by oral microbes and endotoxin. Further, oral epithelial cells, such as keratinocytes, may be susceptible to HIV-1 infection and may contribute to the oral HIV-1 LR. The oral cavity is highly accessible for sequential noninvasive sampling and can routinely be sampled in outpatient or remote areas where resources are limited. An assay that accurately and precisely quantifies the HIV-1 LR, along with corresponding viral output, from oral mucosa test samples would greatly facilitate development and dispensation of a cure or remission treatments for HIV-1 infection.

A high throughput assay that can detect low levels of cell-based HIV-1 RNA has the potential to be particularly valuable in HIV-1 therapy, as such an assay could be used to detect differences in the size and transcriptional profile of the LR due to differences in HIV-1 infected individuals' responses to ART, including timing of ART initiation and duration of treatment, and to predict the time to viral rebound after treatment interruption based on the size and activation level of the LR.

The challenges in developing a quantitative diagnostic for the HIV-1 LR are several: (1) low levels of HIV-1 RNAs produced by latently infected cells; (2) variable expression of HIV-1 RNAs produced by latently infected cells; (3) low levels of latently infected cells; and (4) lack of reliable sampling methods for measuring cell-based HIV-1 RNA levels from anatomical locations most relevant to eradicating the latent reservoir. Detection of low-level RNA in cellular environments may prove very useful for detection of RNA of other viruses, bacteria, and other organisms.

In the past, direct detection of RNA has been difficult to achieve except by the use of hybridizing probes, which entail lengthy hybridization periods and multiple wash steps, followed by visualization procedures. There is a lack of RNA-specific enzymes similar to those used with DNA that achieve PCR amplification, single-nucleotide polymorphism (SNP) detection, and detection of specific RNA sequences and secondary structures.

The HIV-1 Pol/Int region has a relatively linear RNA secondary structure, is well-conserved across different HIV-1 viral genome subtypes, and its presence in HIV-1 infected cells is indicative of production of long, processive, unspliced HIV-1 RNA, which may be predictive of time to viral rebound after treatment interruption. Such long, processive HIV-1 RNA transcripts, as well as singly, multiply, and unspliced HIV-1 RNAs, are required for production of HIV-1 virus. Thus, there is a need for a reliable, sensitive assay to detect long, processive, unspliced HIV-1 RNA containing the Pol/Int region in cellular samples.

Latent HIV-1 infected cells, which constitute the HIV-1 LR in HIV-1 positive individuals who are viremia free due to anti-retroviral therapy, express (1) a high level and accumulation of short, non-processive HIV-1 transcripts consisting of HIV-1 TAR (transactivation response) RNA, and (2) a low level of labile, multiply-spliced (tat-rev) HIV-1 RNA. Through activation or interruption of antiretroviral treatment, latent HIV-infected cells and latent cell line models undergo a transition from short HIV-1 TAR RNA transcripts to long, processive HIV-1 RNA transcripts. Thus, there is additionally a need for a reliable, sensitive assay to detect short HIV-1 non-processive (abortive) RNAs such as HIV-1 TAR in cellular samples.

However, detection of short HIV-1 TAR abortive RNA transcripts by RT-PCR, including ddPCR and qPCR, is hampered by the relatively low efficiency of the reverse transcriptase (RT) enzyme, and also by the secondary structure of the HIV-1 TAR sequence, which is intact at the temperature at which the RT enzyme operates. HIV-1 TAR short transcripts (59-60 nt) (1) must be purified using a method that retains small RNAs, requiring the addition of carrier tRNA, use of phenol/chloroform, and/or the use of a column specific for isolation of small RNAs but that is effective for double-stranded short RNAs such as HIV-1 TAR; and (2) its stable secondary structure inhibits hybridization with complementary or random hexamer primers for reverse transcription. For reliable efficiency, reverse transcription of HIV-1 TAR requires addition of a poly (A) tail sequence, using Poly (A) polymerase, prior to the RT and PCR steps, which adds materials, time, and handling. The secondary structure of HIV-1 TAR also inhibits hybridization with typical hybridization probes.

Fluorogenic detection reactions, including oligonucleotide-templated photoreduction (OTP) reactions, can be useful for low-level detection of nucleic acids, but they have not been developed for RNA, including RNA spliced sites, RNA secondary structure, linear RNA sequences, or cell-based viral RNA. Röthlingshöfer et al. described an OTP detection assay targeting DNA using a 10 nucleotide (nt) PNA-Ru photocatalyst probe and an 8 nt PNA-Azido-Coumarin profluorophore probe in the presence of a few DNA sequences that lack any secondary structure (Röthlingshöfer et al., *Organic Lett.* 2012, 14 (2), 482-485). The reactions were performed in a buffer solution of 0.5 M Tris-HCl, and 0.05% polysorbate 20, at pH 7.4. The background reaction was high (10%) and a large excess of profluorophore probe (500 nM) was used to detect target DNA sequences in the nanomolar (nM) concentration range.

While DNA-targeted OTP reactions have been described, the background reaction needs to be reduced and sensitivity needs to be improved for diagnostic utility. More importantly, RNA-targeted OTP detection reactions have not been developed. Adaptation of templated detection reactions to RNA detection requires the design and development of new probe sequences, new probe chemistries (backbone structure and modifications), and new OTP reactions (photocatalysts and profluorophores) that allow detection of very low concentrations of target RNA sequences in complex environments. Suitable RNA detection protocols using OTP include performing the reaction under flexible conditions, such as with or without denaturing target-probe complexes, the use of opener probes, and isothermal or thermocycling conditions. OTP detection of RNA targets should also be adaptable to using multiple profluorophores, allowing detection of multiple RNA targets in the same sample, thereby enabling multiplex detection.

Thus, there remains a need for new methods for direct detection of RNA targets, particularly low-level RNA targets such as cell-based HIV-1 RNAs, including full-length (such as those containing the Pol/Int sequence), spliced (such as those containing the Tat-Rev spliced site), and abortive (such as those containing the TAR sequence) transcripts that may be indicative of the quantity and the activation level of the HIV-1 LR in an infected individual.

BRIEF SUMMARY

Described herein is a high turnover, sequence-based RNA assay for cellular RNA detection using oligonucleotide-templated photoreduction (OTP). An oligonucleotide (such as PNA or DNA) probe functionalized with a photocatalyst catalytic moiety (the photocatalyst probe can also be referred to as a photocatalyst precursor probe) serves as an anchored pro-catalyst for a fluorogenic reaction with a second, oligonucleotide (such as PNA or DNA) probe functionalized with a profluorophore moiety (the profluorophore probe) that binds adjacently on the target RNA sequence. The profluorophore probe is designed to cycle on and off the target RNA. When the probes are bound to the target sequence, the photocatalyst can be activated and then reduced using light and a reducing agent. The reduced photocatalyst then reduces the profluorophore on the profluorophore probe to form a detectable fluorophore and regenerate the photocatalyst. The fluorophore probe cycles off the target RNA sequence and is replaced by another profluorophore probe (present in the reaction in excess) at a sufficiently high turnover rate to allow for signal amplification. In some embodiments, the probes are designed for high target specificity, to hybridize to target RNA sequences that are conserved across subtypes and clades of a particular virus, such as HIV-1, bacteria, or other genetic target sequence of interest, to achieve a high turnover frequency for the profluorophore probe, to achieve picomolar RNA detection, to provide a total reaction time of 20 min to 24 h, and to facilitate high turnover frequency at an isothermal temperature. Photoreduction of fluorogenic probe pairs provides an improved molecular assay for quantification of target RNA sequences and target RNA-producing cells, such as those present in latent HIV-1 reservoirs, with improved accuracy and precision. In some embodiments, probe pairs are tailored for detection of particular HIV-1 RNA species. In some embodiments, the probe pairs exhibit high selectivity for target RNA sequences, as the short probe sequences are able to discriminate between matched probes and probes with a single nucleotide polymorphism (SNP), as described in Example 7.

In some embodiments, the compositions, reagents, methods, assays, and kits described herein overcome the limitations in the prior art to quantitate latent reservoirs (LR) of HIV-1 infected cells more accurately and more sensitively in virally suppressed individuals under HAART/cART therapy. In some embodiments, the improved probe compositions, reagents, methods, assays, and kits address the need for highly-specific and sensitive detection of cell-based HIV-1 mRNA purified from peripheral blood CD4+ cells isolated from virally suppressed individuals, which may successfully be deployed in the development and evaluation of new treatments for HIV-1 AIDS, including cure treatments. In some embodiments, the presently disclosed compositions, assays, and kits are also useful for elucidating the relationship between production of full-length spliced RNA and virus production by latent and activated cells, data critical to efforts to discover a cure to HIV-1 infection.

The embodiments herein further can be used for detection of specific RNAs and RNA structures involved in other diseases, cell regulation and development, and across populations, allowing for sensitive and quantitative detection of functionally important RNA molecules and monitoring changes in RNA levels as a function of time and treatment. Some embodiments may be used in principle to quantitatively detect a broad range of ribonucleic acid target sequences, and is suitable, for example, to quantitatively detect RNA spliced sites, quantitatively differentiate alternatively spliced forms, or differentially detect RNA in a mixed RNA-DNA sample, such as in a live cell or in samples also containing DNA. Some embodiments are further useful for detecting sequence variants of a target sequence, including single nucleotide polymorphisms (SNP), insertions, deletions, repeats, as well as across short deletions or insertions of up to four bases at the ligation point of a target sequence. Some embodiments are also useful for detection of RNA hairpins, pseudoknots, and other RNA secondary, tertiary, and quaternary structures. Detection specificity is facilitated by the use of short, stabilized probes. Short length allows detection of short, conserved regions within otherwise poorly conserved sequences, particularly found in RNA viruses.

The embodiments herein can also be used for in vivo and in situ detection and quantification of RNA and has broad applicability to the quantitative detection of spliced RNA associated with active or latent viral infection, genetic disease, cancer, gene fusions, and other medically- or environmentally-relevant mutations. Embodiments are suitable for use in point-of-care or high throughput diagnostic devices, including, by way of example, detection in oral and other mucosa, lymphatic tissue, central nervous system (CNS) tissue including brain, cerebrospinal fluid (CSF), GALT, blood, urine, semen, sputum, tears, and other bodily fluids and tissues. Suitable detection platforms include, without limitation, microarrays, in situ detection in tissues or cells, and microfluidic detection. Detection paradigms include, without limitation, quantitative, staging, monitoring, definitive, and point-of-care diagnoses of acute and latent viral and bacterial infections, cancers, and genetic diseases.

Thus, disclosed herein are compositions, reagents, methods, assays, and kits for highly sensitive, precise, and accurate detection and quantification of target ribonucleic acid (RNA) sequences, such as RNA sequences containing spliced sites, as well as RNA sequences containing stem-loops or other topological configurations generated through RNA secondary structure, but also including RNA sequences that do not contain such features. The compositions, reagents, methods, assays, and kits employ quantitative, oligonucleotide-templated photoreduction (OTP) for direct, rapid, precise, and accurate quantification of low RNA levels in a test sample.

In one aspect, the disclosure relates to a fluorogenic nucleic acid composition or kit for quantitative detection of a target ribonucleic acid (RNA) sequence in a test sample comprising at least one pair of oligonucleotide probes comprising a photocatalyst probe and a profluorophore probe, wherein one of the photocatalyst probe and the profluorophore probe is complementary to and capable of specifically binding an upstream portion of the target RNA sequence, and the other probe is complementary to and capable of specifically binding to a downstream portion of the target RNA sequence, the photocatalyst probe comprises a first oligonucleotide covalently bound to a photocatalyst, the profluorophore probe comprises a second oligonucleotide covalently bound to a profluorophore, and the photocatalyst is activatable by exposure to light and a reducing agent to form a reduced, activated photocatalyst that, when both probes of the pair are hybridized to the target RNA sequence, is capable of reducing the profluorophore to form a detectable fluorophore.

In another aspect, the disclosure relates to a fluorogenic method for quantitatively detecting a target ribonucleic acid (RNA) sequence in a sample with a fluorogenic nucleic acid composition or kit as described herein, comprising:

a) in a buffer in the presence or absence of a reducing agent, hybridizing the photocatalyst probe to the target RNA sequence to form a hybridized sample;

b) optionally in a) also including a DNA or PNA opener to hybridize to the target RNA sequence to form a hybridized sample, for the purpose of rendering RNA secondary structure more accessible to either or both of the photocatalyst probe and the profluorophore probe;

c) in a buffer in the presence or absence of a reducing agent, hybridizing the profluorophore probe to the target RNA sequence to form a hybridized profluorophore probe to bring profluorophore and photocatalyst in close proximity and thereby increasing the effective concentration for OTP reaction;

d) optionally, both a) and c), both a) and b), or a), b) and c) hybridizations occur at the same time, in the same tube, at the same temperature and buffer, in the presence or absence of a reducing agent;

e) exposing the hybridized sample to (i) light of a wavelength of about 440 nm and to about 460 nm, preferably 455 nm, and (ii) a reducing agent, if not already present, thereby activating, in the presence of the reducing agent, the photocatalyst to form a reduced, activated photocatalyst. The reduced, activated photocatalyst then spontaneously reduces the profluorophore on the hybridized profluorophore probe to a fluorophore, thereby forming a hybridized fluorophore probe and regenerating the photocatalyst;

f) denaturing the hybridized fluorophore probe from the target RNA sequence under conditions whereby the photocatalyst probe remains hybridized to the target RNA sequence;

g) optionally repeating step c) or d), step e) and step f) at an isothermal temperature or thermocycling; and h) detecting the amount of fluorescence emitted by the fluorophore using a fluorometer that provides the excitation wavelength for the fluorophore and can measure the emission wavelength of the fluorophore after excitation. Preferred is a plate-reader or microfluidic fluorometer for high throughput or small volume, integrated fluorimetry, and a stable background for the fluorometer at the emission wavelength detected.

In another aspect, the disclosure relates to a test kit for quantitative detection of cell-associated RNA or any RNA in a test sample comprising the photocatalyst probe and the profluorophore probe or any of the fluorogenic nucleic acid compositions or kits as described herein and at least one buffer.

This disclosure includes a profluorophore reagent of Formula A, B, C, D, or E:

(A)

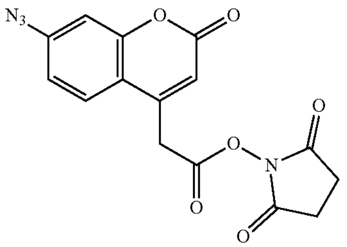

(B)

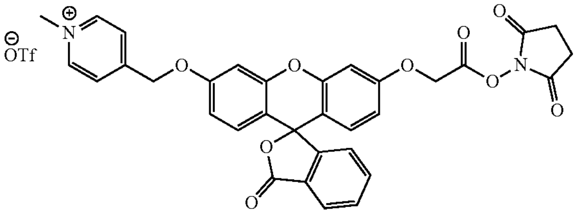

(C)

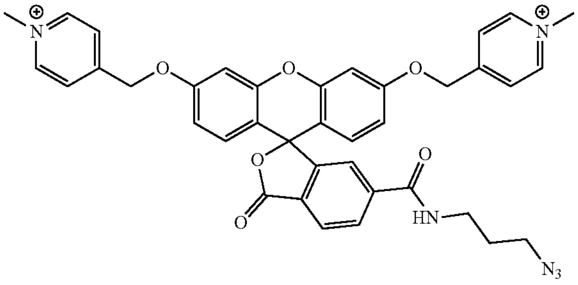

(D)

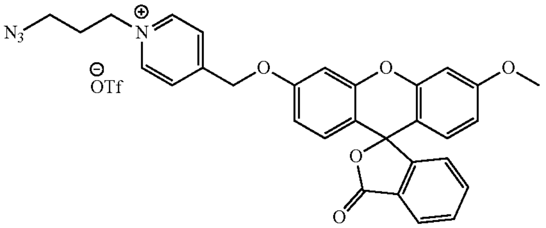

or (E)

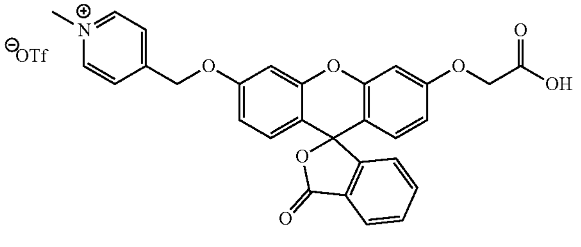

This disclosure includes a photocatalyst reagent of Formula F or G:

(F)

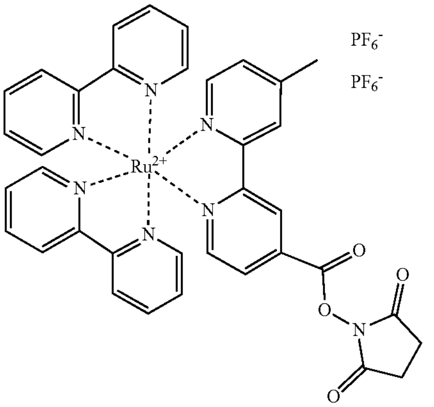

(G)

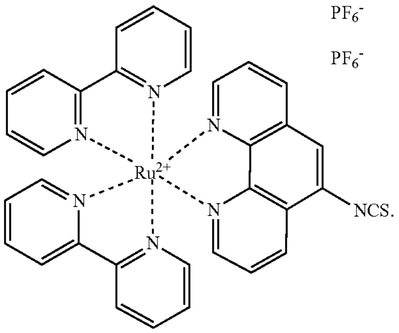

In another aspect, this disclosure provides compositions, reagents, methods, assays, and kits as exemplified by the following non-limiting list of embodiments.

Embodiment 1 is a fluorogenic nucleic acid kit or composition for quantitative detection of a target ribonucleic acid (RNA) sequence in a test sample comprising at least one pair of oligonucleotide probes comprising a photocatalyst probe and a profluorophore probe, wherein one of the photocatalyst probe and the profluorophore probe is complementary to and capable of specifically binding an upstream portion of the target RNA sequence, and the other probe is complementary to and capable of specifically binding to a downstream portion of the target RNA sequence, the photocatalyst probe comprises a first oligonucleotide covalently bound to a photocatalyst, the profluorophore probe comprises a second oligonucleotide covalently bound to a profluorophore, optionally through a self-immolative covalent bond that is broken during the photoreduction reaction to release the activated fluorophore from the profluorophore probe, and the photocatalyst is activatable by exposure to light and a reducing agent to form a reduced, activated photocatalyst such that, when both probes of the pair are hybridized to the target RNA sequence, is capable of photoreducing the profluorophore to form a detectable fluorophore.

Embodiment 2 is the fluorogenic nucleic acid composition or kit of embodiment 1, wherein the target RNA sequence is part of a linear RNA structure, i.e., containing RNA-RNA binding regions with a Tm less than or equal to the reaction temperature.

Embodiment 3 is the fluorogenic nucleic acid composition or kit of embodiment 1, wherein the target RNA sequence is part of a nonlinear RNA secondary structure, i.e., containing RNA-RNA binding regions with a Tm higher than the reaction temperature.

Embodiment 4 is the fluorogenic nucleic acid composition or kit of embodiment 1, wherein the target RNA sequence is viral, bacterial, mammalian, other animal, plant, fungal, protozoan, or archaebacterial RNA.

Embodiment 5 is the fluorogenic nucleic acid composition or kit of embodiment 4, wherein the target RNA sequence is viral RNA.

Embodiment 6 is the fluorogenic nucleic acid composition or kit of embodiment 5, wherein the viral RNA is from a virus selected from an RNA virus, a retrovirus, a flavivirus, and a coronavirus.

Embodiment 7 is the fluorogenic nucleic acid composition or kit of embodiment 5, wherein the viral RNA is from a virus selected from HIV-1, HIV-2, Ebola hemorrhagic fever, SARS, influenza, hepatitis C, West Nile, polio, measles, CMV, Herpes, Zika, Norwalk, yellow fever, dengue, Lassa, Rift Valley fever, Chikungunya, Influenza A, Hantavirus, Marburg, Ebola hemorrhagic fever, Nipah, Rubella, Canine Influenza, HoBi-like pestivirus, Schmallenberg, Simian immunodeficiency (SIV), Powassan, Hepatitis E, Canine hepacivirus, Colorado tick fever, Theiler's disease associated, Ross River, Barmah Forest, and SARS-COV-2 (also named Coronavirus 2019-nCoV, which causes COVID-19) viruses.

Embodiment 8 is the fluorogenic nucleic acid composition or kit of embodiment 5, wherein the viral RNA is from a virus selected from HIV-1, HIV-2, Ebola hemorrhagic fever, SARS, influenza, hepatitis C, West Nile, polio, measles, CMV, Herpes, Zika, Norwalk, yellow fever, dengue, and SARS-COV-2 (also named Coronavirus 2019-nCOV, which causes COVID-19) viruses.

Embodiment 9a is the fluorogenic nucleic acid composition or kit of embodiment 5, wherein the viral RNA is from HIV-1 or HIV-2 viruses. Embodiment 9b is the fluorogenic nucleic acid composition or kit of embodiment 5, wherein the viral RNA is from HIV-1 or HIV-2 or SARS-COV-2 viruses.

Embodiment 10 is the fluorogenic nucleic acid composition or kit of embodiment 9, wherein the target RNA sequence is HIV-1 Pol/Int, TAR, Gag, Env, Nef, Rev, Tat, Vif, Vpr, Vpu, 5'LTR, or 3'LTR.

Embodiment 11 is the fluorogenic nucleic acid composition or kit of embodiment 9, wherein the target RNA sequence is HIV-1 Pol/Int or HIV-1 TAR.

Embodiment 12 is the fluorogenic nucleic acid composition or kit of embodiment 9, wherein the target HIV-1 RNA sequence is spliced at the D4 to A7 splice sites.

Embodiment 13 is the fluorogenic nucleic acid composition or kit of embodiment 9, wherein the target HIV-1 RNA sequence is spliced at the DI to A1 splice sites.

Embodiment 14 is the fluorogenic nucleic acid composition or kit of embodiment 9, wherein the target HIV-1 RNA sequence is spliced at the DI to A1 and possibly also spliced at the D2 to A2 splice sites and possibly also spliced at the D3 to A3, A4a, A4b, A4c, or A5 splice sites, and either spliced or not spliced at the D4 to A7 splice sites.

Embodiment 15 is the fluorogenic nucleic acid composition or kit of embodiment 4, wherein the target RNA sequence is from bacteria.

Embodiment 16 is the fluorogenic nucleic acid composition or kit of embodiment 15, wherein the bacteria is *Borrelia burgdorferi, Mycobacterium tuberculosis, Coxiella burnetii, Neisseria gonorrhoeae, Chlamydia trachomatis, Mycoplasma genitalium, Trichomonas vaginalis*, Group A streptococci, *Helicobacter pylori, Salmonella typhi, Leptospira* bacteria, *Leptospira interrogans* serovars, *Rickettsia* bacteria, or *Orientia tsutsugamushi* bacteria.

Embodiment 17 is the fluorogenic nucleic acid composition or kit of embodiment 4, wherein the target RNA sequence is mammalian RNA.

Embodiment 18 is the fluorogenic nucleic acid composition or kit of embodiment 17, wherein the mammalian RNA is a spliced RNA variant.

Embodiment 19 is the fluorogenic nucleic acid composition or kit of embodiment 18, wherein the spliced RNA variant is selected from CD46, Klotho, DENNDIA, BC200-lncRNA, Dominant negative (DN)-RBFOX2 isoform, SF3B1, BRCA1, ITGB4, PYCR1, and CD44.

Embodiment 20 is the fluorogenic nucleic acid composition or kit of embodiment 17, wherein the mammalian RNA comprises RNA linear structure with a Gibbs free energy (delta G) of equal to or greater than 0 at 20-40° C. and a Tm equal to or below 20-40° C.

Embodiment 21 is the fluorogenic nucleic acid composition or kit of embodiment 17, wherein the mammalian RNA comprises RNA secondary structure with a Gibbs free energy (delta G) of equal to or less than 0 at 20-40° C. and a Tm above 20-40° C.

Embodiment 22 is the fluorogenic nucleic acid composition or kit of any one of embodiments 1 to 21, wherein the photocatalyst is bound to the downstream end of the upstream first probe and the profluorophore is bound to the upstream end of the downstream second probe.

Embodiment 23 is the fluorogenic nucleic acid composition or kit of any one of embodiments 1 to 21, wherein the profluorophore is bound to the downstream end of the upstream first probe and the photocatalyst is bound to the upstream end of the downstream second probe.

Embodiment 24 is the fluorogenic nucleic acid composition or kit of any of the preceding embodiments, wherein at least one of the oligonucleotide probes in a pair comprises at least one modified-backbone nucleotide.

Embodiment 25 is the fluorogenic nucleic acid composition or kit of any of embodiments 1 to 24, wherein the two probes in the pair are DNA probes, the two probes in the pair are PNA probes, or one probe in the pair is a DNA probe and the other probe is a PNA probe.

Embodiment 26 is the fluorogenic nucleic acid composition or kit of any of embodiments 1 to 24, wherein the two probes in the pair are both DNA probes.

Embodiment 27 is the fluorogenic nucleic acid composition or kit of any of embodiments 1 to 24, wherein the two probes in the pair are PNA probes, wherein each PNA probe optionally comprises one or more hydrophilic monomers.

Embodiment 28 is the fluorogenic nucleic acid composition or kit of any of embodiments 1 to 24, wherein one probe in the pair is a DNA probe and the other probe is a PNA probe, wherein the PNA probe optionally comprises one or more hydrophilic monomers.

Embodiment 29 is the fluorogenic nucleic acid composition or kit of embodiment 27 or embodiment 28, wherein the one or more hydrophilic monomers are each independently a monomer of structure (A):

(A)

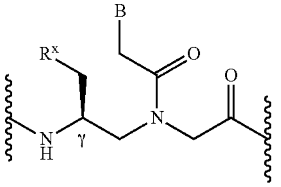

where $R^x$ is $—O(CH_2OCH_2)_p—OH$ or $—O(CH_2OCH_2)_p—OCH_3$, wherein p is 0, 1, 2, 3, 4, or 5.

Embodiment 30 is the fluorogenic nucleic acid composition or kit of any of the preceding embodiments, wherein the binding of the probes of the probe pair to the target RNA sequence leaves a single-stranded gap of 0 to 8 nucleotides of the target RNA sequence between the bound probes.

Embodiment 31 is the fluorogenic nucleic acid composition or kit of embodiment 29, wherein the gap is from 0 to 7 nucleotides, optionally wherein the two probes in the pair are DNA probes or one probe in the pair is a DNA probe and the other probe is a PNA probe, or the gap is 1 to 7 nucleotides, optionally wherein the two probes in the pair are PNA probes.

Embodiment 32 is the fluorogenic nucleic acid composition or kit of any of the preceding embodiments, wherein the photocatalyst probe comprises an oligonucleotide sequence with a melting temperature (Tm) of above the reaction temperature, to allow the photocatalyst probe to remain in place through more than one catalytic cycle, and at least 5° C. or more above the reaction temperature.

Embodiment 33 is the fluorogenic nucleic acid composition or kit of any of the preceding embodiments, wherein the profluorophore probe comprises an oligonucleotide sequence with a Tm of equal to or below the reaction temperature, to allow for release of the fluorophore probe from the target sequence and binding of an unreacted profluorophore probe after one catalytic cycle. In a reaction, the profluorophore is provided at 2-10 times or more in excess of the concentration of photocatalyst to allow for a high reaction turnover and thus amplification of the resulting fluorophore signal.

Embodiment 34 is the fluorogenic nucleic acid composition or kit of any one of the preceding embodiments, wherein the target RNA sequence is HIV-1 Pol/Int, the photocatalyst probe is a DNA probe with the sequence: 5'-GCACTGACTAATTTATCTACT-3' (SEQ ID NO: 1), and/or the profluorophore probe is a DNA probe with a sequence selected from: (a) 5'-TTCATTTCCT-3' (SEQ ID NO: 2); (b) 5'-TTCATTTCCTCCAAT-3' (SEQ ID NO: 3); and (c) 5'-TTCATTTCCTCCAATTCC-3' (SEQ ID NO: 4).

Embodiment 35 is the fluorogenic nucleic acid composition or kit of embodiment 34, wherein the photocatalyst probe is the DNA probe with the sequence of SEQ ID NO: 1 and the profluorophore probe is the DNA probe with the sequence of SEQ ID NO: 2.

Embodiment 36 is the fluorogenic nucleic acid composition or kit of any one of embodiments 1 to 33, wherein the target RNA sequence is HIV-1 Pol/Int, the photocatalyst probe is a PNA probe with the sequence: 5'-Acetyl-O-TTTATCTACT-Lys-3' (SEQ ID NO: 5), and/or the profluorophore probe is a PNA probe with a sequence selected from: (a) 5'-TTCATTTC-O-3' (SEQ ID NO: 6); (b) 5'-TTCATTT-O-3' (SEQ ID NO: 7); and (c) 5'-TTCATT-O-3' (SEQ ID NO: 8).

Embodiment 37 is the fluorogenic nucleic acid composition or kit of any one of embodiments 1 to 33, wherein the target RNA sequence is HIV-1 TAR, the photocatalyst probe is a PNA probe with the sequence: 5'-Acetyl-O-GA*GCT*CCC*AG-Lys-3' (SEQ ID NO: 9) or a DNA probe with the sequence: 5'-TAGCCAGAGAGCTCCCAG-3' (SEQ ID NO: 10), and/or the profluorophore probe is a PNA probe with the sequence: 5'-TCA*GAT*CT-O-3' (SEQ ID NO: 11) or a DNA probe with the sequence: 5'-TCA-GATCT-3' (SEQ ID NO: 12) or 5'-TCAGATCTGGT-3' (SEQ ID NO: 13).

Embodiment 38 is the fluorogenic nucleic acid composition or kit of embodiment 37, wherein the photocatalyst probe has the sequence of SEQ ID NO: 9 and the profluorophore probe is a PNA probe with the sequence of SEQ ID NO: 11 or is a DNA probe with the sequence of SEQ ID NO: 12.

Embodiment 39 is the fluorogenic nucleic acid composition or kit of embodiment 37, wherein the photocatalyst probe is a DNA probe with the sequence of SEQ ID NO: 10 and the profluorophore probe is a DNA probe with the sequence of SEQ ID NO: 12 or 13.

Embodiment 40 is the fluorogenic nucleic acid composition or kit of any of the preceding embodiments, wherein the photocatalyst comprises a photoactivatable complex of ruthenium (II), iridium (III), rhodium (III), osmium (II), palladium (II), or platinum (II).

Embodiment 41 is the fluorogenic nucleic acid composition or kit of embodiment 40, wherein the photocatalyst comprises a photoactivatable pyridyl complex of ruthenium (II) or iridium (III).

Embodiment 42 is the fluorogenic nucleic acid composition or kit of embodiment 40, wherein the photocatalyst comprises $Ru(bpy)_3^{2+}$, $Ru(bpy)_2(phen)^{2+}$, $Ru(bpy)_2(MeCN)_2(PF_6)_2$, or $Ir(ppy)_3$.

Embodiment 43 is the fluorogenic nucleic acid composition or kit of embodiment 40, wherein the photocatalyst is:

(F)

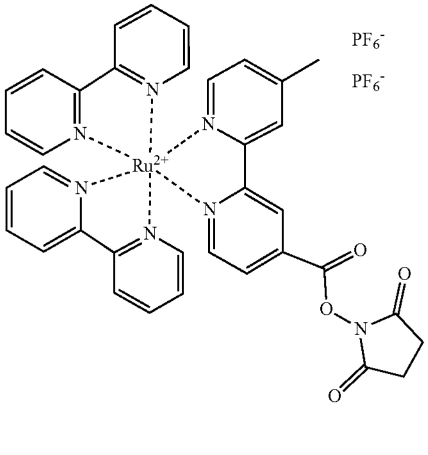

or

-continued (G)

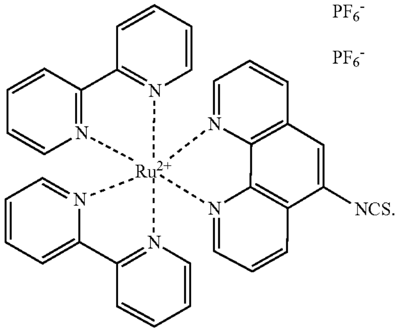

Embodiment 44 is the fluorogenic nucleic acid composition or kit of any of the preceding embodiments, wherein the light is visible light in a wavelength from 400 to 500, 420 to 480, from 440 to 460 nm, or 455 nm.

Embodiment 45 is the fluorogenic nucleic acid composition or kit of any of the preceding embodiments, wherein the profluorophore comprises a photoreactive aryl azido moiety or a pyridinium moiety.

Embodiment 46 is the fluorogenic nucleic acid composition or kit of any of the preceding embodiments, wherein the profluorophore comprises a coumarin or a fluorescein group.

Embodiment 47 is the fluorogenic nucleic acid composition or kit of any of the preceding embodiments, wherein the profluorophore is:

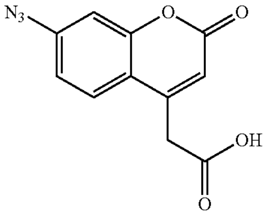

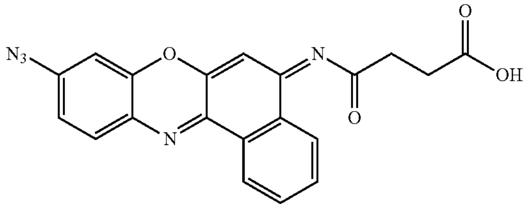

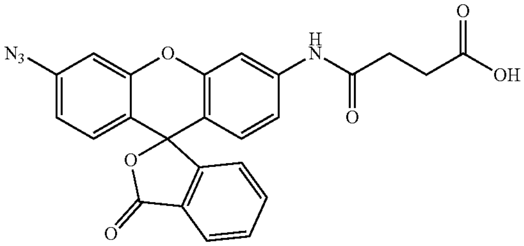

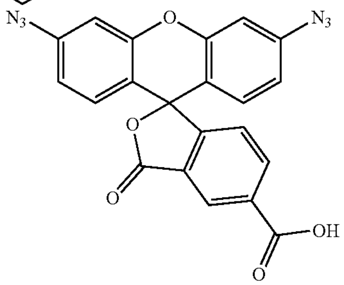

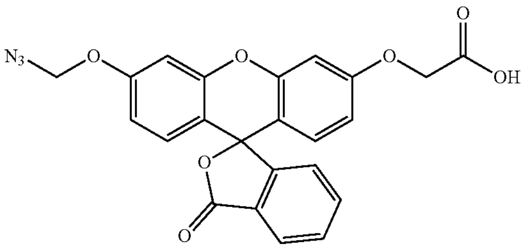

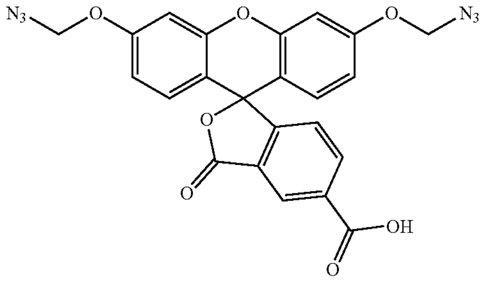

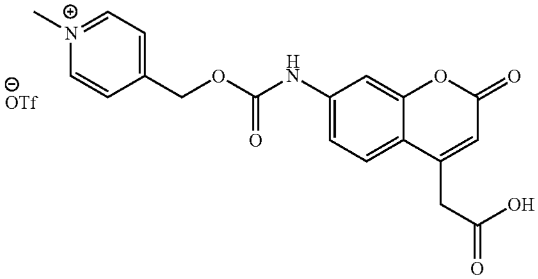

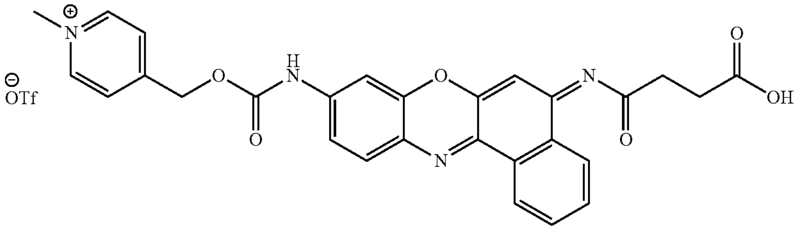

-continued
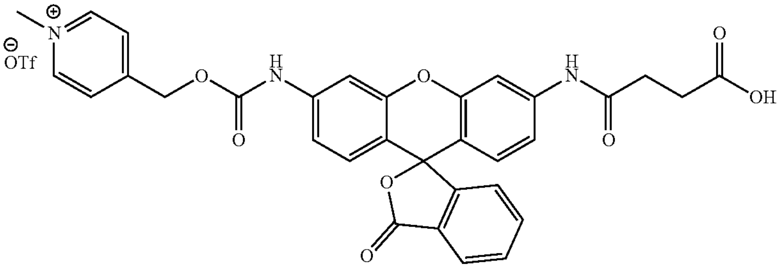
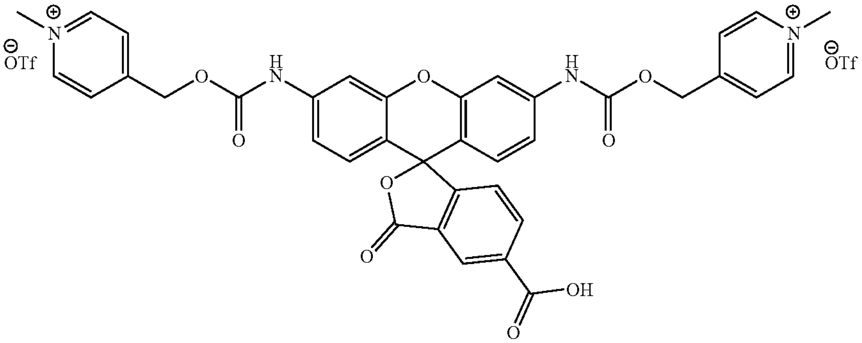
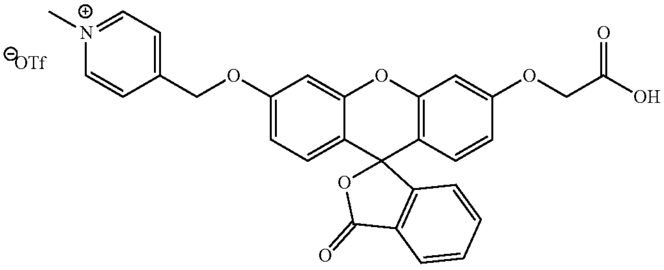
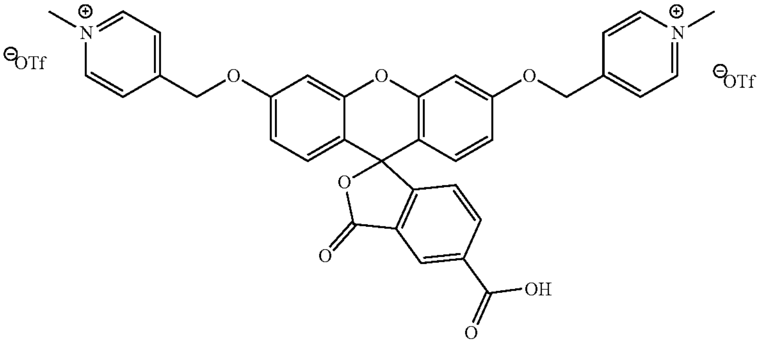
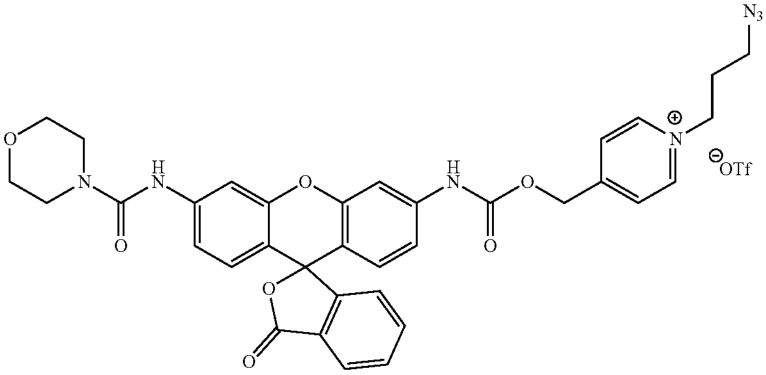

-continued
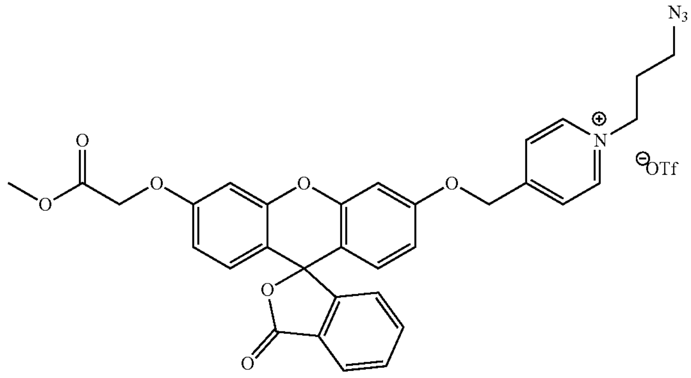
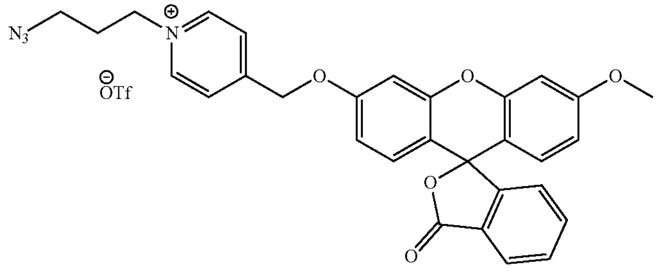
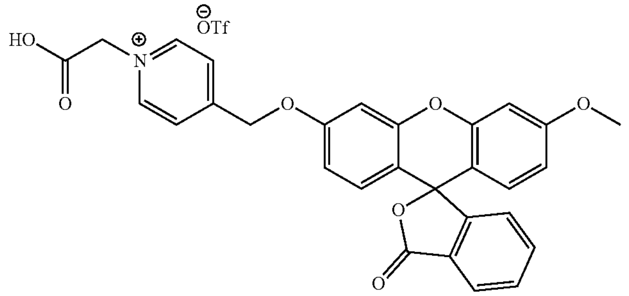
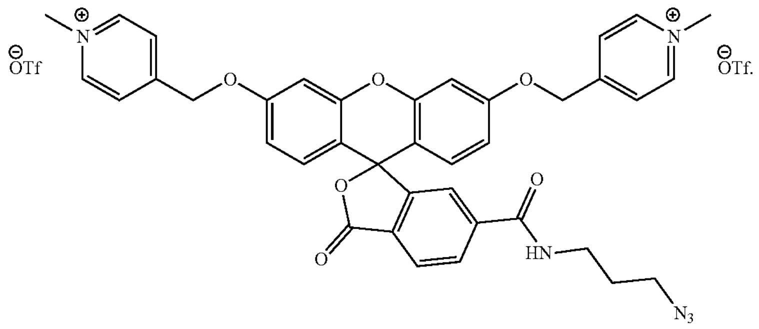

Embodiment 48 is the fluorogenic nucleic acid composition or kit of any of the preceding embodiments, wherein the profluorophore comprises 7-azidocoumarin or pyridinium-substituted fluorescein.

Embodiment 49 is the fluorogenic nucleic acid composition or kit of any of the preceding embodiments, wherein the profluorophore is:

(A)

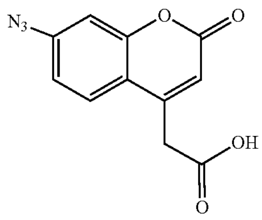

or (B)

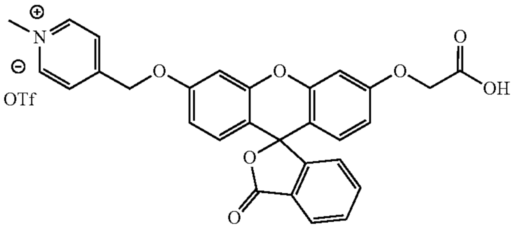

or (C)

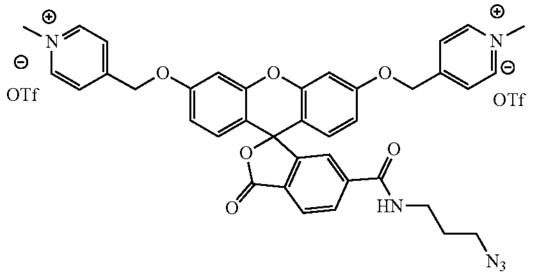

or (D)

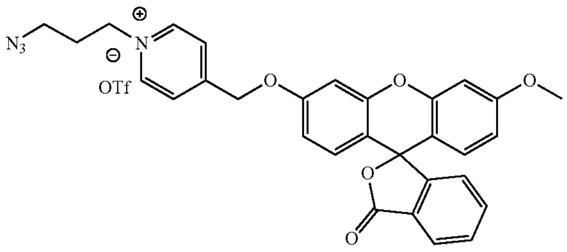

and the photocatalyst is:

(F)

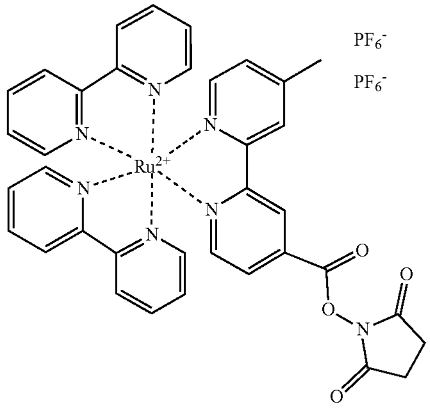

or (G)

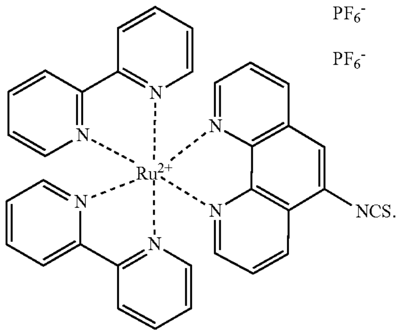

Embodiment 50 is the fluorogenic nucleic acid composition or kit of any one of the preceding embodiments, wherein the probe pair is selected from:

(1) Probe Pair 1 (DNA Probe Pair for HIV-1 Pol/Int):

(SEQ ID NO: 15)
5'-GCACTGACTAATTTATCTACT-Ru-3' (21 nt)

(SEQ ID NO: 16)
5'-Azido-Coumarin-TTCATTTCCT-3' (10 nt)

(2) Probe Pair 2 (DNA Probe Pair for HIV-1 Pol/Int):

SEQ ID NO: 15
(21 nt)

(SEQ ID NO: 17)
5'-Azido-Coumarin-TTCATTTCCTCCAAT-3' (15 nt)

(3) Probe Pair 3 (DNA Probe Pair for HIV-1 Pol/Int):

SEQ ID NO: 15
(21 nt)

(SEQ ID NO: 18)
5'-Azido-Coumarin-TTCATTTCCTCCAATTCC-3' (18 nt)

(4) Probe Pair 4 (PNA Probe Pair for HIV-1 Pol/Int):

(SEQ ID NO: 19)
5'-Acetyl-O-TTTATCTACT-Lys-Ru-3' (10 nt)

(SEQ ID NO: 20)
5'-Azido-Coumarin-TTCATTTC-O-3' (8 nt), wherein O is an O-linker -continued (5) Probe Pair 5 (PNA Probe Pair for HIV-1 Pol/Int):

SEQ ID NO: 19 (10 nt)

(SEQ ID NO: 21)
5'-Azido-Coumarin-TTCATTT-O-3' (7 nt)

(6) Probe Pair 6 (PNA Probe Pair for HIV-1 Pol/Int):

SEQ ID NO: 19 (10 nt)

(SEQ ID NO: 22)
5'-Azido-Coumarin-TTCATT-O-3' (6 nt)

(7) Probe Pair 7 (PNA Probe Pair for HIV-1 TAR):

(SEQ ID NO: 24)
5'-Acetyl-O-GA*GCT*CCC*AG-Lys-Ru-3' (10 nt)

(SEQ ID NO: 25)
5'-Azido-Coumarin-TCA*GAT*CT-O-3' (8 nt)

(8) Probe Pair 8 (PNA-DNA Probe Pair for HIV-1 TAR):

SEQ ID NO: 24 (10 nt)

(SEQ ID NO: 26)
5'-Azido-Coumarin-TCAGATCT-3' (8 nt)

(9) Probe Pair 9 (DNA-DNA Probe Pair for HIV-1 TAR):

(SEQ ID NO: 27)
5'-TAGCCAGAGAGCTCCCAG-Ru-3' (18 nt)

SEQ ID NO: 26 (8 nt)

(10) Probe Pair 10 (DNA-DNA Probe Pair for HIV-1 TAR):

SEQ ID NO: 27 (18 nt)

(SEQ ID NO: 29)
5'-Azido-Coumarin-TCAGATCTGGT-3' (11 nt)

(11) Probe Pair 11 (DNA-DNA Probe Pair for HIV-1 TAR) (underlined base is single base mismatch with HIV-1 TAR RNA template SEQ ID NO: 23):

(SEQ ID NO: 28)
5'-TAGCCAGAGA<u>A</u>CTCCCAG-Ru-3' (18 nt)

SEQ ID NO: 29 (11 nt).

(12) Probe Pair 12 (PNA-PNA Probe Pair for HIV-1 TAR):

SEQ ID NO: 24

(SEQ ID NO: 33)
5'-Pyridinium-Fluorescein-TC*AGA*TCT*O-3'

(13) Probe Pair 13 (PNA-PNA Probe Pair for HIV-1 TAR):

SEQ ID NO: 24

(SEQ ID NO: 34)
5'-Pyridinium-Fluorescein-O-TC*AGA*TCT*O-3'

(14) Probe Pair 14 (PNA-DNA Probe Pair for HIV-1 TAR):

SEQ ID NO: 24

(SEQ ID NO: 35)
5'-Pyridinium-Fluorescein-TCAGATCT-3'

(15) Probe Pair 15 (DNA-DNA Probe Pair for HIV-1 TAR):

SEQ ID NO: 27 (18 nt)

(SEQ ID NO: 35)
5'-Pyridinium-Fluorescein-TCAGATCT-3'

-continued

(16) Probe Pair 16 (DNA-DNA Probe Pair for SARS-CoV-2 Spike RNA):

(SEQ ID NO: 37)
5'-TGATAACTAGCGCATATACCTG-Ru-Ru-3'

(SEQ ID NO: 38)
5'-Azido-Coumarin-CCAATGGG-3'

(17) Probe Pair 17 (DNA-DNA Probe Pair for SARS-CoV-2 ORF8 RNA):

(SEQ ID NO: 40)
5'-CACAATTCAATTAAAGGTGCT-Ru-3'

(SEQ ID NO: 41)
5'-Azido-Coumarin-TTTTCTAGCT-3'

Embodiment 51 is the fluorogenic nucleic acid composition or kit of any one of the preceding embodiments, wherein a DNA or PNA opener is selected from:

(1) HIV-1 TAR DNA Opener (SEQ ID NO: 30)
5'-GGTCTAACCAGAGAGACCCA-3'

(2) HIV-1 TAR PNA Opener (SEQ ID NO: 31)
5'-GGT*CTA*ACC*AGA*GAG*ACC*CA-3'

Embodiment 52 is a fluorogenic method for quantitatively detecting a target ribonucleic acid (RNA) sequence in a sample with the fluorogenic nucleic acid composition or kit of any one of embodiments 1 to 51, comprising a) hybridizing the photocatalyst probe to the target RNA sequence to form a hybridized sample in the reaction buffer in the presence or absence of a reducing agent;
b) optionally hybridizing the photocatalyst probe to the target RNA sequence to form a hybridized sample in the presence of a DNA or PNA opener in the reaction buffer in the presence or absence of a reducing agent;
c) optionally hybridizing the photocatalyst probe to the target RNA sequence to form a hybridized sample in the presence or absence of a DNA or PNA opener and exposing the mixture to denaturing conditions followed by a temperature 5° C. below the annealing temperature of the photocatalyst probe and/or opener to its target RNA sequence, in the reaction buffer in the presence or absence of a reducing agent;
d) hybridizing the profluorophore probe to the target RNA sequence to form a hybridized profluorophore probe, in the reaction buffer in the presence or absence of a reducing agent;
e) optionally performing steps a) and d) together, containing photocatalyst probe, profluorophore probe, and target RNA sequence, in the reaction buffer in the presence or absence of a reducing agent;
f) optionally performing steps b) and d) together, containing photocatalyst probe, profluorophore probe, DNA or PNA opener, and target RNA sequence, in the reaction buffer in the presence or absence of a reducing agent;
g) exposing the fully hybridized sample from d), e), or f) containing photocatalyst probe, profluorophore probe, and optional DNA or PNA opener, in reaction buffer to (i) light of a wavelength of about 440 nm to about 460 nm, preferably 455 nm, and (ii) a reducing agent (if not already in the reaction mixture), thereby activating the photocatalyst to form a reduced, activated photocatalyst, which then spontaneously reduces the profluorophore on the hybridized profluorophore probe to a fluorophore, thereby forming a hybridized fluorophore probe and regenerating the photocatalyst;

h) denaturing the hybridized fluorophore probe from the target RNA sequence under conditions whereby the photocatalyst probe remains hybridized to the target RNA sequence;

i) optionally repeating step d), g) and step h); and j) detecting the amount of fluorescence emitted by the fluorophore using a fluorometer that provides the excitation wavelength for the fluorophore and can measure the emission wavelength of the fluorophore after excitation.

Embodiment 53 is the method of embodiment 52, wherein the fluorogenic nucleic acid composition or kit is the composition or kit of embodiment 50 or embodiment 51.

Embodiment 54 is the method of embodiment 52 or embodiment 53, wherein the concentration of the profluorophore probe during the hybridization step is from about 25 nM to about 500 nM, or about 50 nM to about 200 nM, or about 100 nM.

Embodiment 55 is the method of embodiment 52 or embodiment 53, wherein the concentration of the photocatalyst probe during the hybridization step is from about 5 nM to about 200 nM, or about 25 to about 125 nM, or about 25 nM or 50 nM.

Embodiment 56 is the method of any one of embodiments 52 to 55, wherein the reducing agent is sodium ascorbate, formamide, N-diisopropylethylamine, or NADPH.

Embodiment 57 is the method of any one of embodiments 52 to 56, wherein the denaturing comprises heating at a temperature from about 70° C. to about 100° C., optionally followed by an opener annealing temperature of about 30° C. to about 70° C.

Embodiment 58 is the method of any one of embodiments 52 to 57, wherein the denaturing is performed under isothermal conditions.

Embodiment 59 is the method of embodiment 58, wherein the isothermal conditions comprise a temperature from about 20° C. to about 70° C.

Embodiment 60 is the method of embodiment 58, wherein the isothermal conditions comprise a temperature from about 20° C. to about 40° C.

Embodiment 61 is the method of any one of embodiments 52 to 57, wherein steps d), e), or f) and h) are performed under thermocycling conditions.

Embodiment 62 is the method of embodiment 61, wherein step h) is performed at a temperature from about 30° C. to about 50° C., and step d), e), or f) is performed at a temperature from about 20° C. to about 40° C.

Embodiment 63 is the method of embodiment 61, wherein step h) is performed at a temperature from about 30° C. to about 70° C., and step d), e), or f) is performed at a temperature from about 20° C. to about 50° C.

Embodiment 64 is the method of embodiment 61, wherein step h) is performed at a temperature from about 40° C. to about 80° C., and step d), e), or f) is performed at a temperature from about 20° C. to about 60° C.

Embodiment 65 is the method of any one of embodiments 52 to 64, wherein an excess (with regards to the concentration of target RNA sequence) of each probe of the fluorogenic nucleic acid composition or kit is added to the sample in a buffer (such as phosphate-buffered saline (PBS)) or in a buffered salt concentration of about 0.05 to about 20×, in the presence or absence of a reducing agent.

Embodiment 66 is the method of any one of embodiments 52 to 65, wherein the hybridizing of photocatalyst probe and/or the profluorophore probe is performed in the presence of a DNA or PNA opener, optionally at a temperature of about 40° C. to about 80° C., or about 50° C. to about 70° C., or about 55° C. to about 65° C., or about 65° C.

Embodiment 67 is the method of any one of embodiments 52 to 66, wherein the hybridizing of the photocatalyst probe and/or the profluorophore probe is performed in the presence of at least one additive selected from DMSO, formamide, betaine, spermidine, and a detergent.

Embodiment 68 is the method of any one of embodiments 52 to 67, wherein the method comprises normalizing the amount of fluorescence that is detected to the amount of fluorescence that is detected in a negative control sample that contains a non-target RNA sequence.

Embodiment 69 is the method of any one of embodiments 52 to 67, wherein the method comprises normalizing the amount of fluorescence that is detected to the amount of fluorescence that is detected in a positive control sample that contains a target RNA sequence of known concentration.

Embodiment 70 is the fluorogenic method of any one of embodiments 52 to 69, wherein the method comprises performing the method on a first sample that is obtained from a patient before administration of an anti-HIV medication and performing the method on a second sample that is obtained from the patient after administration of the anti-HIV medication, and comparing the results of the method for the first and second samples.

Embodiment 71 is the fluorogenic method of any one of embodiments 52 to 70, wherein the sample is obtained from a patient and the detected fluorescence shows the patient has a latent HIV reservoir.

Embodiment 72 is the fluorogenic method of embodiment 71, comprising administering an anti-HIV medication to the patient with the latent HIV reservoir.

Embodiment 73 is a test kit for quantitative detection of cell-associated or viral particle RNA in a test sample comprising the probes of the fluorogenic nucleic acid composition or kit of any one of embodiments 1 to 51 and at least one buffer.

Embodiment 74 is the test kit of embodiment 73, wherein the at least one buffer is a reaction buffer.

Embodiment 75 is the test kit of embodiment 74, wherein the reaction buffer comprises phosphate-buffered saline (PBS) or other buffered salt solution with a concentration of about 0.05×to about 20×, or about 0.05×to about 10×, or about 0.05×to 5×, or about 1×for the composition of PBS.

Embodiment 76 is the test kit of embodiment 75, wherein the kit comprises lyophilized probes of the fluorogenic nucleic acid composition, buffer, and reducing agent.

Embodiment 77 is a profluorophore reagent of Formula A, B, C, or D:

(A)

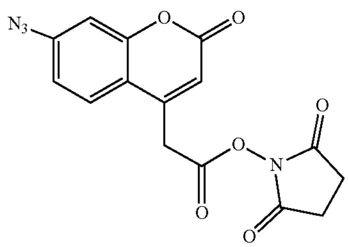

-continued (B)

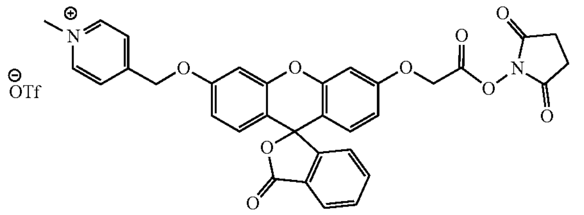

(C)

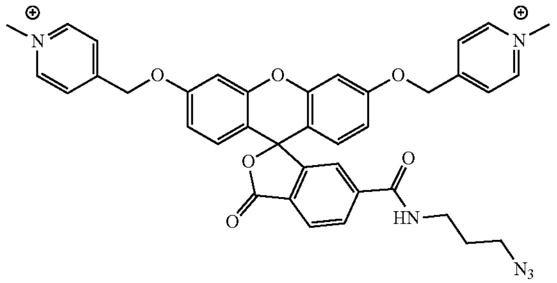

(D)

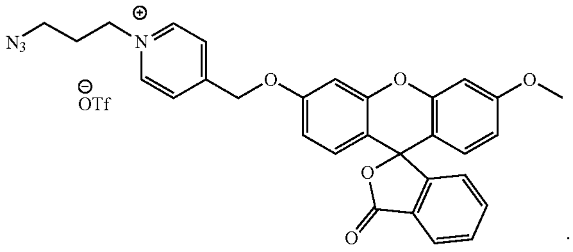

.

Embodiment 78 is a photocatalyst reagent of Formula F or G:

(F)

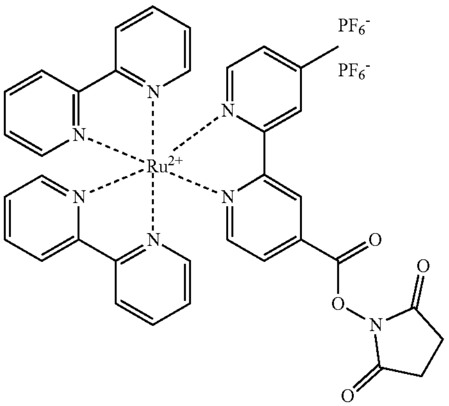

-continued (G)

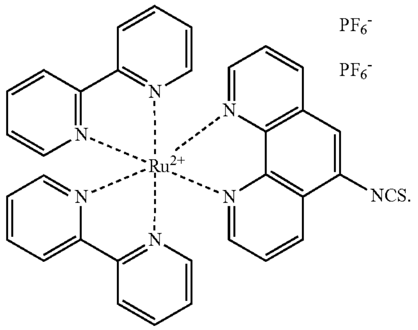

Additional objects and advantages will be set forth in part in the description which follows, and in part will be obvious from the description, or may be learned by practice. The objects and advantages will be realized and attained by means of the elements and combinations particularly pointed out in the appended claims.

BRIEF DESCRIPTION OF THE DRAWINGS

The accompanying drawings, which are incorporated in and constitute a part of this specification, illustrate one (several) embodiment(s) and together with the description, serve to explain the principles described herein.

FIGS. 1A-1B are graphs of the percent conversion of the profluorophore to the corresponding fluorophore with respect to time, for a range of concentrations (in nM) of synthetic target HIV-1 Pol/Int RNA (FIG. 1A) or HIV-1 TAR RNA (FIG. 1B), using the corresponding DNA-DNA OTP probe pairs for each target RNA, demonstrating quantitative detection of synthetic RNA target sequences, as described in Example 1.

FIG. 2 is a graph of the percent conversion of the profluorophore to the corresponding fluorophore with respect to time, for a range of concentrations (in nM) of synthetic target HIV-1 TAR RNA, in the presence of a PNA opener and heat in the photocatalyst probe hybridization step, using the same HIV-1 TAR DNA-DNA OTP probe pair in Example 1, demonstrating improved detection of an RNA secondary structure through the use of a PNA opener and an initial heating step, as described in Example 2.

FIGS. 3A and 3B are graphs of the percent conversion of the profluorophore to the corresponding fluorophore with respect to time, for HIV-negative human cell total RNA spiked with a range of concentrations of synthetic target HIV-1 Pol/Int RNA (FIG. 3A) or HIV-1 shortened TAR RNA (FIG. 3B), demonstrating the same quantitative detection of synthetic RNA spiked into HIV-negative cell total RNA as seen for the synthetic RNAs alone, with no detection in non-spiked HIV-negative cell total RNA using DNA-DNA OTP probes (FIG. 3A), but non-specific reaction detected in non-spiked HIV-negative cell total RNA using PNA-PNA OTP probes (FIG. 3B), as described in Example 3.

FIGS. 4A-4B are graphs of the percent conversion of the profluorophore to the corresponding fluorophore with respect to time, for HIV-positive human cell total RNA after HIV-1 virus transcriptional induction by PMA and ionomycin for 0, 24, 48, and 72 h using HIV-1 Pol/Int DNA-DNA OTP probes (FIG. 4A) (0 and 24 h induction times) or HIV-1 TAR DNA-DNA OTP probes with a PNA opener and an initial heating step (FIG. 4B) (0, 24, 48, and 72 h cell induction times), demonstrating quantitative detection of native HIV-1 RNAs known to increase with induction time, as described in Example 4.

FIGS. 5A-5B are graphs of the percent conversion of the profluorophore to the corresponding fluorophore with respect to time, for different concentrations of in vitro-transcribed negative control RNAs, demonstrating the specificity of the reaction through no detection of negative control RNAs by either the HIV-1 Pol/Int DNA-DNA OTP probe set (FIG. 5A) or the HIV-1 TAR DNA-PNA OTP probe set (FIG. 5B), as described in Example 5.

FIGS. 6A-6B are graphs of the percent conversion of the profluorophore to the corresponding fluorophore with respect to time, for a single concentration of different synthetic target HIV-1 Pol/Int RNAs or HIV-1 shortened TAR RNAs, with varying gap distances between the probe target regions, for an HIV-1 Pol/Int DNA-DNA OTP probe set (FIG. 6A) and an HIV-1 PNA-PNA TAR OTP probe set (FIG. 6B), demonstrating the different, nonobvious effect of gap distance for DNA-DNA vs. PNA-PNA probe sets, as described in Example 6.

FIG. 7 is a graph of the percent conversion of the profluorophore to the corresponding fluorophore with respect to time, for a single concentration of synthetic target HIV-1 TAR RNA, with a perfect match vs. a single nucleotide mismatch between the target RNA sequence and the HIV-1 TAR photocatalyst probes, for an HIV-1 TAR DNA-DNA OTP probe set, demonstrating the potential to detect single nucleotide polymorphisms (SNPs), as described in Example 7.

FIG. 8 is a graph of the percent conversion of the profluorophore to the corresponding fluorophore with respect to time, for a single concentration of synthetic target HIV-1 Pol/Int RNA, using different length HIV-1 Pol/Int DNA profluorophore probes with the same HIV-1 Pol/Int DNA photocatalyst probe, demonstrating the stringent, nonobvious length requirements of a profluorophore DNA probe for optimal assay sensitivity, as described in Example 8.

FIGS. 9A-9B are graphs of the percent conversion of the profluorophore to the corresponding fluorophore with respect to time, using a HIV-1 TAR DNA-DNA OTP probe set for a range of concentrations of HIV-1 TAR RNA, with 1×PBS (FIG. 9A) or 5×PBS buffer (FIG. 9B). The results show no detection of 1 nM HIV-1 TAR RNA and only very low detection of 10 nM HIV-1 TAR RNA with 1× PBS, while use of a 5×PBS buffer provides optimal detection of both target RNA concentrations, as described in Example 9.

FIGS. 10A-10B are graphs of the percent conversion of the profluorophore to the corresponding fluorophore with respect to time, using a HIV-1 TAR PNA-PNA OTP probe set for a range of concentrations of HIV-1 TAR RNA, with 1× PBS (FIG. 10A) or 0.1×PBS buffer (FIG. 10B). The results show improved detection of HIV-1 TAR RNA with 0.1×PBS, as described in Example 10.

FIGS. 14A-14B are graphs of the percent conversion of the profluorophore to the corresponding fluorophore with respect to time, using a HIV-1 TAR PNA-PNA OTP probe set (FIG. 14A) or a HIV-1 TAR DNA-DNA OTP probe set (FIG. 14B) for a range of concentrations of HIV-1 shortened TAR RNA, with 1× PBS (FIG. 14A) or 5×PBS buffer (FIG. 14B). The results show lower background of HIV-1 TAR RNA using Pyridinium-Fluorescein as the profluorophore, compared to the Azido-Coumarin profluorophore, as described in Example 14.

FIGS. 15A-15B are graphs of the percent conversion of the profluorophore to the corresponding fluorophore with respect to time, using an HIV-1 TAR DNA-DNA OTP probe set for a range of concentrations of HIV-1 shortened TAR RNA, with 5× PBS buffer and 0.1% Digitonin (FIG. 15A) or 0.05% polysorbate-20 detergent additive. The results show lower background and improved detection using Digitonin with a Pyridinium-Fluorescein profluorophore, compared to polysorbate-20 with the same profluorophore, as described in Example 15.

FIGS. 16A-16B are graphs of the percent conversion of the profluorophore to the corresponding fluorophore with respect to time, for a range of concentrations (in nM) of synthetic target SARS-COV-2 Spike RNA (FIG. 16A) or SARS-COV-2 ORF8 RNA (FIG. 16B), using the corresponding DNA-DNA OTP probe pairs for each target RNA, demonstrating quantitative detection of synthetic RNA target sequences, as described in Example 16.

SEQUENCES

Figure 1A:
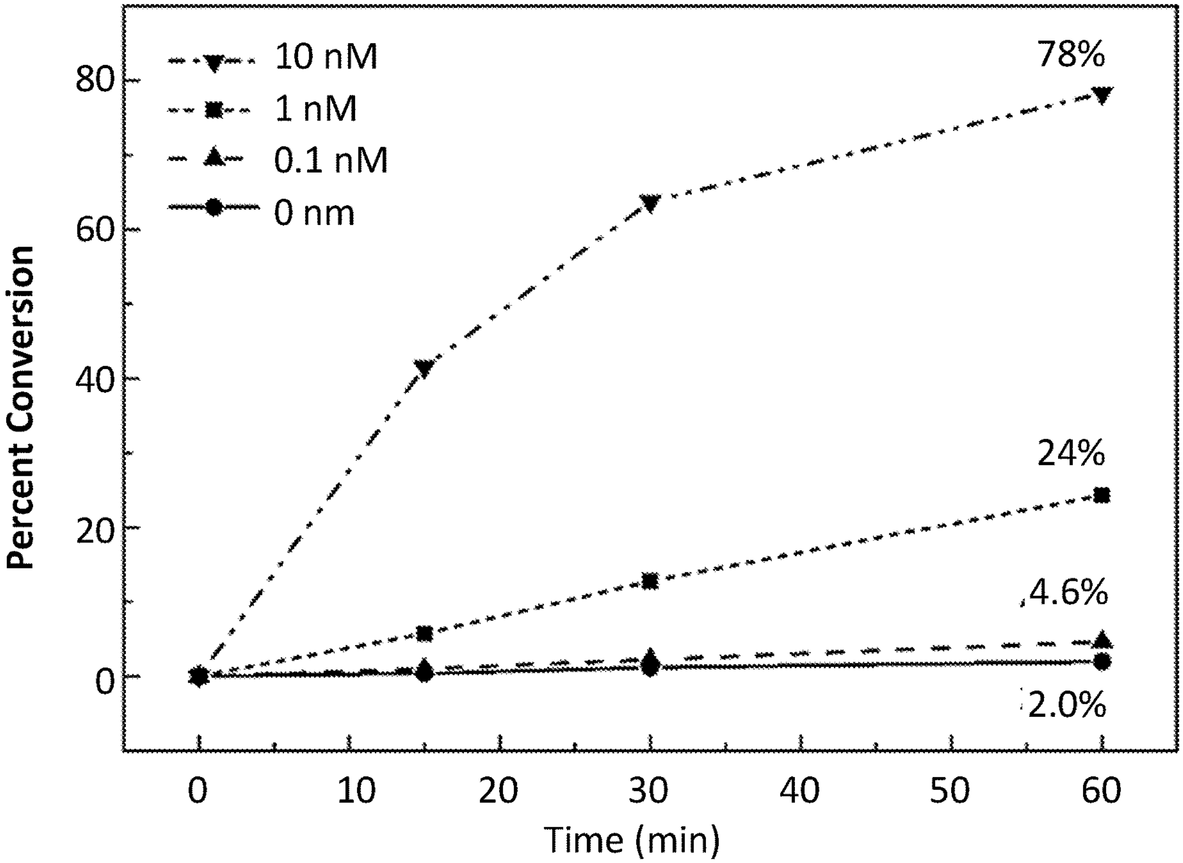
FIGS. 1A-1B show quantitative detection by OTP reaction of HIV-1 Pol/Int RNA (FIG. 1A) or HIV-1 TAR RNA (FIG. 1B).

The following sequences are disclosed herein.

TABLE 1

Sequences.

| SEQ ID NO. | SEQUENCE | DESCRIPTION |
|---|---|---|
| 1 | 5'-GCACTGACTAATTTATCTACT-3' | HIV-1 Pol/Int DNA Probe |
| 2 | 5'-TTCATTTCCT-3' | HIV-1 Pol/Int DNA Probe |
| 3 | 5'-TTCATTTCCTCCAAT-3' | HIV-1 Pol/Int DNA Probe |
| 4 | 5'-TTCATTTCCTCCAATTCC-3' | HIV-1 Pol/Int DNA Probe |
| 5 | 5'-Acetyl-O-TTTATCTACT-Lys-3' | HIV-1 Pol/Int PNA Probe |
| 6 | 5'-TTCATTTC-O-3' | HIV-1 Pol/Int PNA Probe |
| 7 | 5'-TTCATTT-O-3' | HIV-1 Pol/Int PNA Probe |
| 8 | 5'-TTCATT-O-3' | HIV-1 Pol/Int PNA Probe |
| 9 | 5'-Acetyl-O-GA*GCT*CCC*AG-Lys-3' | HIV-1 TAR PNA Probe |
| 10 | 5'-TAGCCAGAGAGCTCCCAG-3' | HIV-1 TAR DNA Probe |
| 11 | 5'-TCA*GAT*CT-O-3' | HIV-1 TAR PNA Probe |
| 12 | 5'-TCAGATCT-3' | HIV-1 TAR DNA Probe |
| 13 | 5'-TCAGATCTGGT-3' | HIV-1 TAR DNA Probe |
| 14 | 5'-GAAUUGGAGGAAAUGAACAAGUAGAUAAA UUAGUCAGUGCUGGAA-3' | HIV-1 Pol/Int Target RNA Sequence |
| 15 | 5'-GCACTGACTAATTTATCTACT-Ru-3' | HIV-1 Pol/Int DNA Probe |
| 16 | 5'-Azido-Coumarin-TTCATTTCCT-3' | HIV-1 Pol/Int DNA Probe |
| 17 | 5'-Azido-Coumarin-TTCATTTCCTCCAAT-3' | HIV-1 Pol/Int DNA Probe |
| 18 | 5'-Azido-Coumarin-TTCATTTCCTCCAATTCC-3' | HIV-1 Pol/Int DNA Probe |
| 19 | 5'-Acetyl-O-TTTATCTACT-Lys-Ru-3' | HIV-1 Pol/Int PNA Probe |
| 20 | 5'-Azido-Coumarin-TTCATTTC-O-3' | HIV-1 Pol/Int PNA Probe |
| 21 | 5'-Azido-Coumarin-TTCATTT-O-3' | HIV-1 Pol/Int PNA Probe |
| 22 | 5'-Azido-Coumarin-TTCATT-O-3' | HIV-1 Pol/Int PNA Probe |
| 23 | 5'-UGGGUCUCUCUGGUUAGACCAGAUCUGAG CCUGGGAGCUCUCUGGCUAACUAGGGAACCCA-3' | HIV-1 TAR Target RNA Sequence |

TABLE 1-continued

Sequences.

| SEQ ID NO. | SEQUENCE | DESCRIPTION |
|---|---|---|
| 24 | 5'-Acetyl-O-GA*GCT*CCC*AG-Lys-Ru-3' | HIV-1 TAR PNA Probe |
| 25 | 5'-Azido-Coumarin-TCA*GAT*CT-O-3' | HIV-1 TAR PNA Probe |
| 26 | 5'-Azido-Coumarin-TCAGATCT-3' | HIV-1 TAR DNA Probe |
| 27 | 5'-TAGCCAGAGAGCTCCCAG-Ru-3' | HIV-1 TAR DNA Probe |
| 28 | 5'-TAGCCAGAGAACTCCCAG-Ru-3' | HIV-1 TAR DNA Probe |
| 29 | 5'-Azido-Coumarin-TCAGATCTGGT-3' | HIV-1 TAR DNA Probe |
| 30 | 5'-GGTCTAACCAGAGAGACCCA-3' | HIV-1 TAR DNA Opener |
| 31 | 5'-GGT*CTA*ACC*AGA*GAG*ACC*CA-3' | HIV-1 TAR PNA Opener |
| 32 | 5'-CAGAUCUGAG CCUGGGAGCUCU-3' | HIV-1 Shortened TAR Target RNA Sequence |
| 33 | 5'-Pyridinium-Fluorescein-TC*AGA*TCT*-O-3' | HIV-1 TAR PNA Probe |
| 34 | 5'-Pyridinium-Fluorescein-O-TC*AGA*TCT*-O-3' | HIV-1 TAR PNA Probe |
| 35 | 5'-Pyridinium-Fluorescein-TCAGATCT-3' | HIV-1 TAR DNA Probe |
| 36 | 5'-ACCCAUUGGUGCAGGUAUAUGCGCUAGUUAUCAG-3' | SARS-CoV-2 Spike (S) Target RNA Sequence |
| 37 | 5'-TGATAACTAGCGCATATACCTG-Ru-3' | SARS-CoV-2 Spike DNA Probe |
| 38 | 5'-Azido-Coumarin-CCAATGGG-3' | SARS-CoV-2 Spike DNA Probe |
| 39 | 5'-GAGCUAGAAAAUCAGCACCUUUAAUUGAAUUGUGC-3' | SARS-CoV-2 ORF8 Target RNA Sequence |
| 40 | 5'-CACAATTCAATTAAAGGTGCT-Ru-3' | SARS-CoV-2 ORF8 DNA Probe |
| 41 | 5'-Azido-Coumarin-TTTTCTAGCT-3' | SARS-CoV-2 ORF8 DNA Probe |
| 42 | 5'-TGATAACTAGCGCATATACCTG-3' | SARS-CoV-2 Spike DNA Probe |
| 43 | 5'-CCAATGGG-3' | SARS-CoV-2 Spike DNA Probe |
| 44 | 5'-CACAATTCAATTAAAGGTGCT-3' | SARS-CoV-2 ORF8 DNA Probe |
| 45 | 5'-TTTTCTAGCT-3' | SARS-CoV-2 ORF8 DNA Probe |

DETAILED DESCRIPTION

It is to be understood that both the foregoing general description and the following detailed description are exemplary and explanatory only and are not restrictive of the claims.

This application provides probe compositions, kits, and methods for quantitative RNA target sequence detection. The compositions, kits, and methods employ tagged, probe-set pairs of sequences that hybridize specifically to proximal regions in a target RNA sequence and provide precise and accurate quantitation of the levels of a nucleic acid target sequence present in a test sample.

In accordance with the description is a fluorogenic nucleic acid composition or kit for quantitative detection of a target ribonucleic acid (RNA) sequence in a test sample comprising at least one pair of oligonucleotide probes comprising a photocatalyst probe and a profluorophore probe,

- wherein one of the photocatalyst probe and the profluorophore probe is complementary to and capable of specifically binding an upstream portion of the target RNA sequence, and the other probe is complementary to and capable of specifically binding to a downstream portion of the target RNA sequence,
- the photocatalyst probe comprises a first oligonucleotide covalently bound to a photocatalyst,
- the profluorophore probe comprises a second oligonucleotide covalently bound to a profluorophore, optionally through a self-immolative linker, and
- the photocatalyst is activatable by exposure to light and a reducing agent to form a reduced, activated photocatalyst that, when both probes of the pair are hybridized to the target RNA sequence, is capable of reducing the profluorophore to form a detectable fluorophore, optionally also releasing the fluorophore from its oligonucleotide probe through rupture of the self-immolative linker.

I. Oligonucleotide-Templated Photoreduction (OTP) Mechanisms

Shown in Scheme 1 below is a chemical mechanism for a representative oligonucleotide-templated photoreduction (OTP) catalytic cycle.

A photocatalyst probe includes a photocatalyst (inactive catalyst) and a profluorophore probe includes a profluorophore. The inactive catalyst is exposed to a suitable wavelength of light (hv) to form a photoactivated catalyst, that can then be reduced by a reducing agent such as ascorbate (HASc"), to form a reduced, photoactivated catalyst still covalently bound to the oligonucleotide of the probe. The reduced, photoactivated catalyst, in close proximity with the profluorophore on the second probe when both probes are bound in close proximity to a target RNA sequence, reduces the profluorophore to form a fluorophore on the second probe, and, at the same time, regenerates the inactive photocatalyst. Quantitative detection of the target RNA sequence may be performed by detecting the fluorescent signal generated by the fluorophore.

In some instances the photocatalyst probe may be referred to as a photocatalyst precursor probe because it is in an inactive state (i.e., precursor) state before it is photoactivated and subsequently reduced. Only after the photocatalyst probe (or photocatalyst precursor probe) is photoactivated and reduced does it become capable of reducing the profluorophore to form a fluorophore on the second probe.

In an exemplary embodiment, as shown in Scheme 1 above, the reduced, photoactivated catalyst reduces an azide profluorophore moiety, such as an aryl azide. As shown in Scheme 1, and in detail in Scheme 2 below, an aryl azide (A) is reduced to form an azide radical anion (B), which decomposes to lose N2 to form a nitrene radical anion (C) that may be protonated to give an aminyl radical (D) or abstract a hydrogen to form an amide anion (E). The reduction of the aminyl radical (D) also yields the amide anion (E), which is protonated to provide an amino derivative as the fluorophore (F).

Scheme 1. Mechanism of Oligonucleotide-templated Photoreduction (OTP) of a Pro-Fluorophore

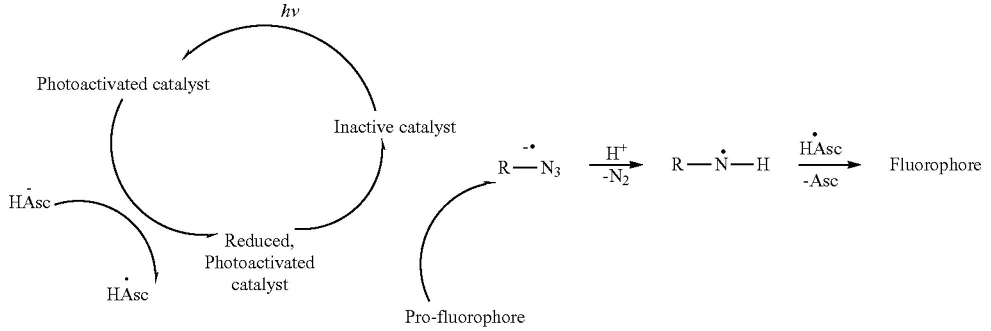

Scheme 2. Aryl Azide Photoreduction.

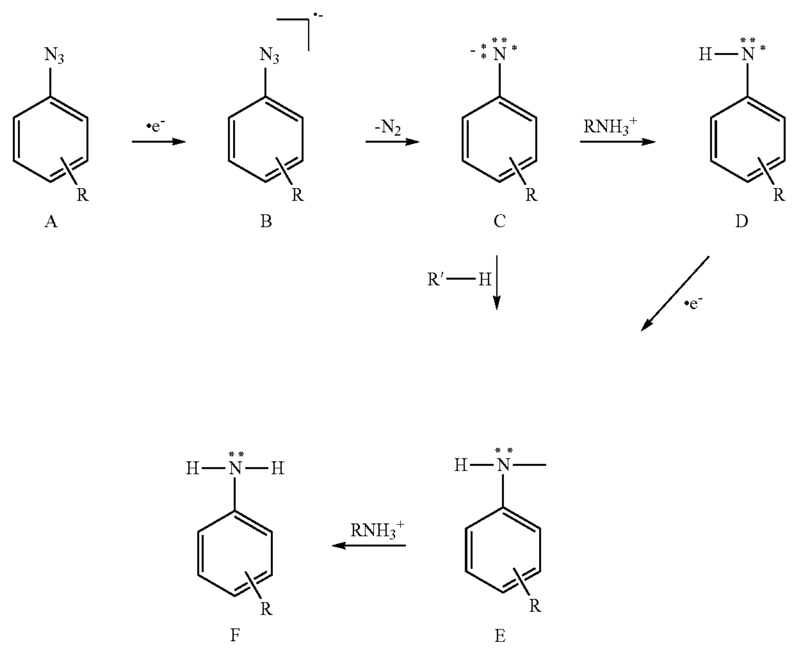

Scheme 3 below shows the catalytic cycle in which the probes hybridize to the target sequence and participate in the OTP reaction. As shown, in a particular embodiment, an RNA target nucleic acid (RNA Template) is hybridized to a photocatalyst probe (Probe 1) that includes a covalently bound ruthenium-based catalyst in its inactive form. A profluorophore probe (Probe 2), which includes a covalently bound profluorophore (such as an aryl azide moiety), hybridizes on the target RNA sequence proximally to Probe 1. The inactive ruthenium catalyst (also referred to as the photocatalyst or photocatalyst precursor) is activated by exposure to light (e.g., at hv=455 nm) in the presence of a reducing agent such as ascorbate, and the reduced, activated photocatalyst reduces the azide to a fluorogenic aryl amino group. Amino-derivatized Probe 2 then denatures from the target nucleic acid, while Probe 1 remains hybridized, allowing for hybridization of a second molecule of the profluorophore probe (Probe 2) and further turnover of the catalytic cycle.

Scheme 3. Isothermal Signal Amplification for Detection of an RNA Target Sequence by Oligonucleotide-Templated Photoreduction (OTP).

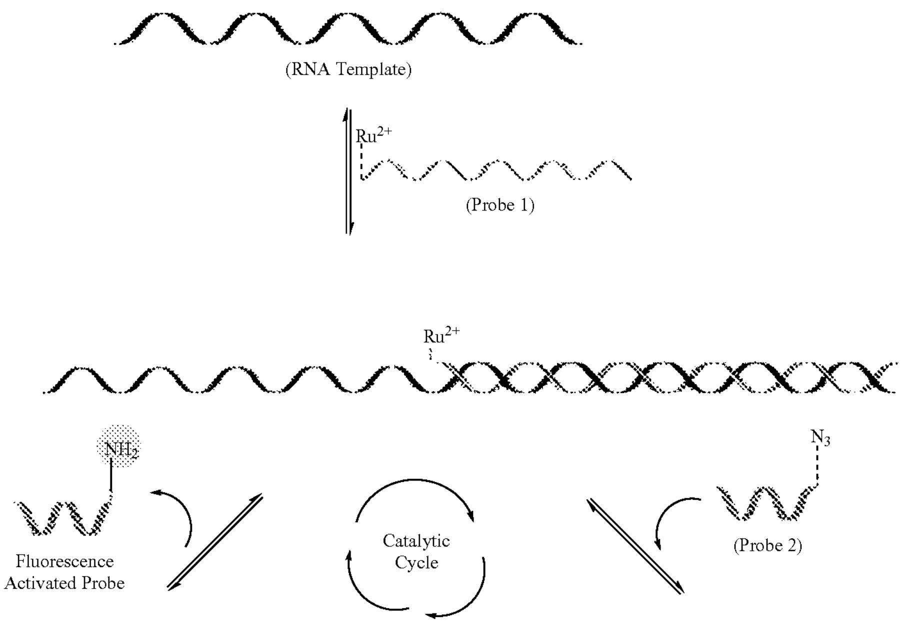

-continued

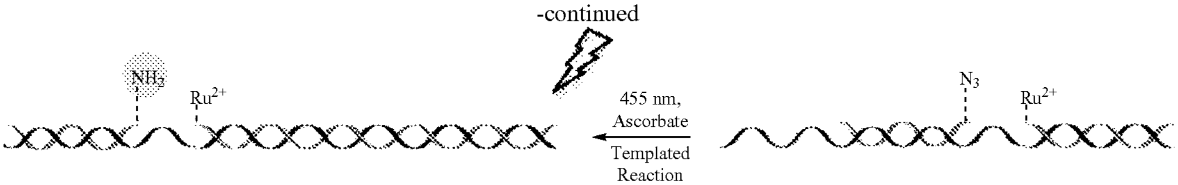

II. Fluorogenic Nucleic Acid Compositions or Kits

A fluorogenic nucleic acid composition or kit for quantitative detection of a target RNA sequence in a test sample includes at least one pair of oligonucleotide probes comprising a photocatalyst probe and a profluorophore probe. In some embodiments, one of the photocatalyst probe and the profluorophore probe is complementary to and capable of specifically binding an upstream portion of the target RNA sequence, and the other probe is complementary to and capable of specifically binding to a downstream portion of the target RNA sequence. In some embodiments, the photocatalyst probe comprises a first oligonucleotide covalently bound to a photocatalyst, the profluorophore probe comprises a second oligonucleotide covalently bound to a profluorophore, optionally through a self-immolative linker, and the photocatalyst is activatable by exposure to light and a reducing agent to form a reduced, activated photocatalyst. The activated photocatalyst, when both probes of the pair are hybridized to the target RNA sequence, is capable of reducing the profluorophore to form a detectable fluorophore, optionally also releasing the fluorophore from its oligonucleotide probe by rupture of a self-immolative linker.

Thus, the composition employs at least one pair of oligonucleotide probes where one probe in the pair comprises a photocatalyst and the other probe comprises a profluorophore. When the photocatalyst is photoactivated and reduced, and the probes come sufficiently close to one another, the reduced, activated photocatalyst reduces the profluorophore to form a fluorophore covalently bound to or released from the second probe.

A. Oligonucleotide Probes

The fluorogenic nucleic acid composition or kit comprises at least one pair of oligonucleotide probes. In some embodiments, the composition or kit comprises more than one pair of oligonucleotide probes. In some embodiments, the composition or kit comprises two or more pairs of oligonucleotide probes that each bind to a different target RNA sequence. In some embodiments, the composition or kit comprises two or more oligonucleotide probes capable of distinguishing between one or more single nucleotide polymorphisms (SNP) in the same RNA sequence. In such embodiments, the fluorophores are selected to be independently detectable.

Each pair of probes constitutes a "probe pair" comprised of two probes: an upstream, first probe having a 5' and a 3' end; and a downstream, second probe having a 5' and a 3' end, which are complementary to upstream and downstream portions, respectively, of the target RNA sequence. A photocatalyst is attached to one end of one probe and a profluorophore is attached to one end of the other probe. The upstream and downstream portions of the target sequence may be selected with a gap of, for example, 0 to 8 nucleotides between them on a linear RNA or a gap consisting of the RNA sequence within a nonlinear structure that brings together the two probe binding sites in the RNA target sequence into close proximity.

1. Types of Oligonucleotide Probes

The probe oligonucleotide sequences can be composed of nucleotides selected from natural nucleotides (such as DNA or RNA) and modified nucleotide structures, such as monomers with modified nucleotide backbones. Modified nucleotide structures include peptide nucleic acids (PNA), bridged nucleic acids (BNA), locked nucleic acids (LNA), guanidine-modified PNA (GPNA), and other modifications. In some embodiments, one probe in a pair comprises modified-backbone oligonucleotides. In some embodiments, some of the nucleotides in a probe are modified-backbone nucleotides and others are unmodified. In some embodiments, at least one of the oligonucleotide probes in a pair comprises at least one modified-backbone nucleotide. In some embodiments, an individual probe is homogeneous, and includes nucleotides of a single type, such as DNA, PNA, BNA, LNA, or GPNA. In some embodiments, an individual probe is heterogenous, and includes a mixture of nucleotide types selected from natural nucleotides and modified backbone nucleotides. In some embodiments, both probes in a pair comprise modified-backbone nucleotides. In some embodiments, the two probes in a pair comprise different types of modified-backbone nucleotides. In some embodiments, one probe in a pair comprises modified-backbone nucleotides. In some embodiments, both probes in a pair comprise solely natural oligonucleotides (e.g., DNA). In some embodiments, probe pairs are homogeneous, comprising the same type of nucleotides in each probe. In some embodiments, probe pairs are heterologous, wherein one member comprises one type of nucleotide and the other member comprises a different type of nucleotide. In some embodiments, the two probes in the pair are DNA probes, the two probes in the pair are PNA probes, or one probe in the pair is a DNA probe and the other probe is a PNA probe.

In some embodiments, one or both probes in a probe pair comprises a peptide nucleic acid (PNA) backbone. A PNA is a synthetic mimic of DNA in which the deoxyribose phosphate backbone of DNA is replaced by a pseudo-peptide polymer to which the nucleobases are attached. A PNA backbone comprises monomers of the following structure:

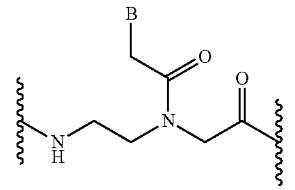

wherein each B is independently a DNA nucleobase (adenine, guanine, cytosine, thymine, or uracil). PNAs hybridize with complementary RNAs with high affinity and specificity due to their uncharged and flexible amide backbone. Thus, a PNA sequence can be shorter than its cognate oligonucleotide sequence, yet retain the same binding affinity. A shorter complementary sequence improves specificity over a longer sequence.

In some embodiments, the PNA probe comprises one or more hydrophilic monomers, such as a lysine, a glutamine, or other polar or charged amino acid, a 5'-terminal acetyl cap, or a monomer with a gamma-position modification, such as shown in the following structure:

(A)

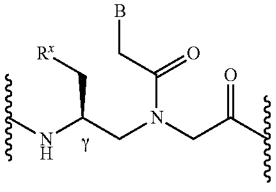

where $R^x$ is $-(OCH_2CH_2)_p-OH$ or $-(OCH_2CH_2)_p-OCH_3$, wherein p is 0, 1, 2, 3, 4, or 5. In some embodiments, a PNA probe comprises at least one monomer of one of the following monomer structures, where p is 0 ($R^x$ is $-OH$ or $-OCH_3$), or p is 2 as in structure (B), also known as diethylene glycol or miniPEG, or structure (C), also known as diethylene glycol monomethyl ether:

(B)

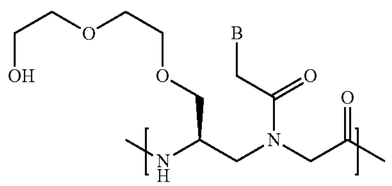

(C)

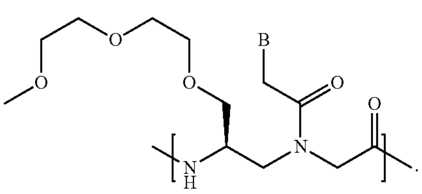

In some embodiments, a PNA probe comprises 1, 2, 3, or more monomers of these hydrophilic structures (A), (B), and/or (C). In PNA sequence provided herein, a B* in the oligonucleotide refers to a modified PNA, such as structure (A), (B), or (C). In some embodiments, one probe has modified monomers of structure (B) and the other probe has modified monomers of structure (C). In some embodiments, the photocatalyst probe comprises 1, 2, 3, or more monomers of structure (B). In some embodiments, the profluorophore probe comprises 1, 2, 3, or more monomers of structure (C). Where a probe has a PNA monomer as a terminal residue, the structure will terminate with a $NH_2$— (5' end, also called H—) or a —$CONH_2$ (3' end, also called-$NH_2$) group. In some embodiments, the PNA includes a monomer that is a capped terminal residue, such as an N-acetyl group (in place of the 5' end $NH_2$—).

In some embodiments, PNA probes with one or more gamma positions modified with miniPEG or glycol ether have increased solubility in water (hydrophilicity), which helps prevent PNA strand aggregation, reduce the amount of PNA required for the assay reaction, and reduce background signal. Such modified structures bind with a higher Tm to RNA targets than PNA probes without such modifications, adopt a more linear structure, with less aggregation within each probe, and thus can invade secondary structures in RNA and form triplex structures with RNA double-stranded target sequences. Using such modified PNA probes optionally reduces or eliminates the need for an initial, pre-reaction heating step and/or use of a DNA or PNA opener, to help probes access stem-loop and other RNA secondary structures.

In some embodiments, modifying a PNA at the gamma position drives the structure to a right-handed helix, which improves hybridization to RNA, thus increasing affinity of the PNA to RNA by increasing the Tm of the PNA by about 5 to 8° C. per gamma-PEG modification. The higher $T_m$ allows the use of a shorter PNA probe and thus more specific binding to RNA.

In some embodiments, either the photocatalyst or the profluorophore moiety is attached to the PNA oligonucleotide via a spacer or linker, such as O-(AEEA, AEEEA, or egl), E-, X-, C3-, C4-, C6-, C6A-, or C12-linkers. These linkers can be attached to the end of the oligonucleotide probe that is not attached to the photocatalyst or profluorophore moiety to improve hydrophilicity and water-solubility, but can also be added between the oligonucleotide and photocatalyst or profluorophore moiety. Further hydrophilic groups can also be attached to the linkers to improve aqueous solubility.

Figure 3A:
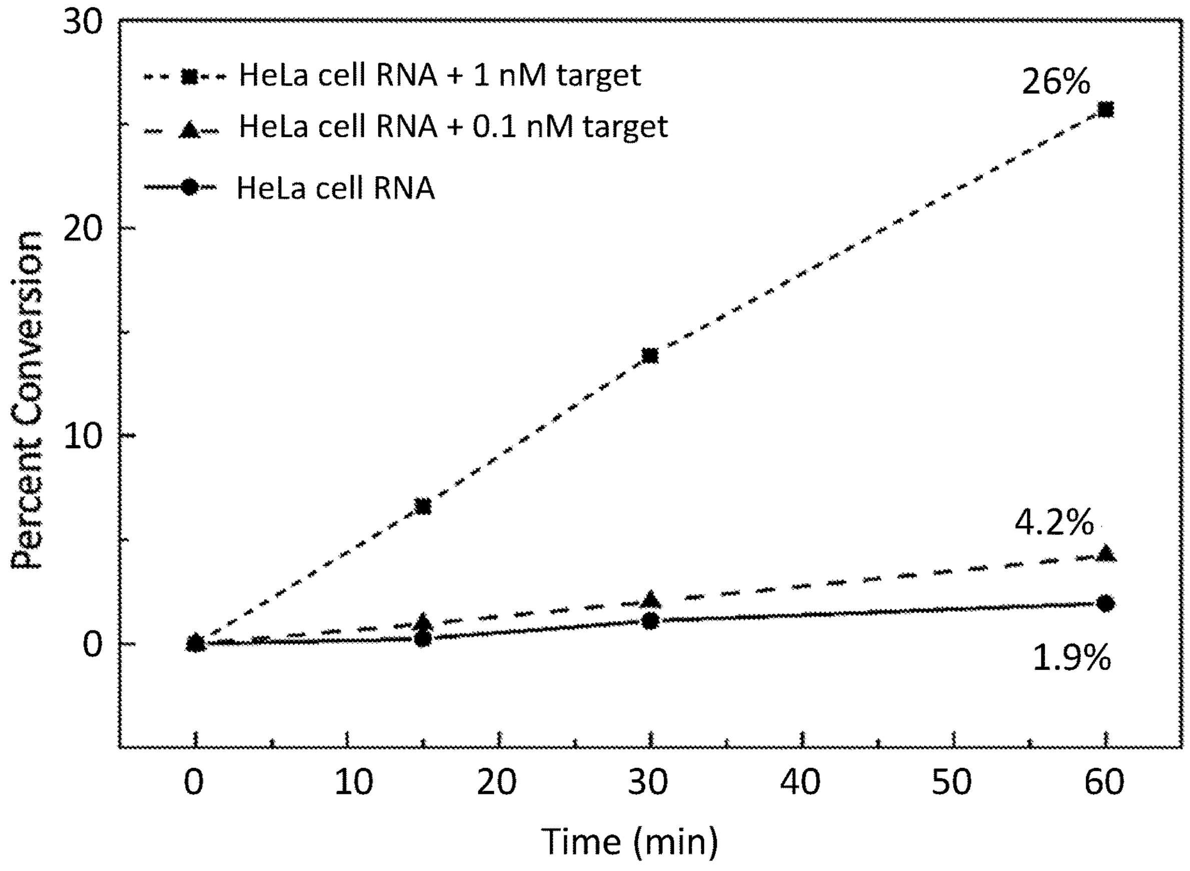
FIGS. 3A-3B show quantitative OTP detection of target sequence spiked into HIV-negative human cell total RNA.
Figure 3B:
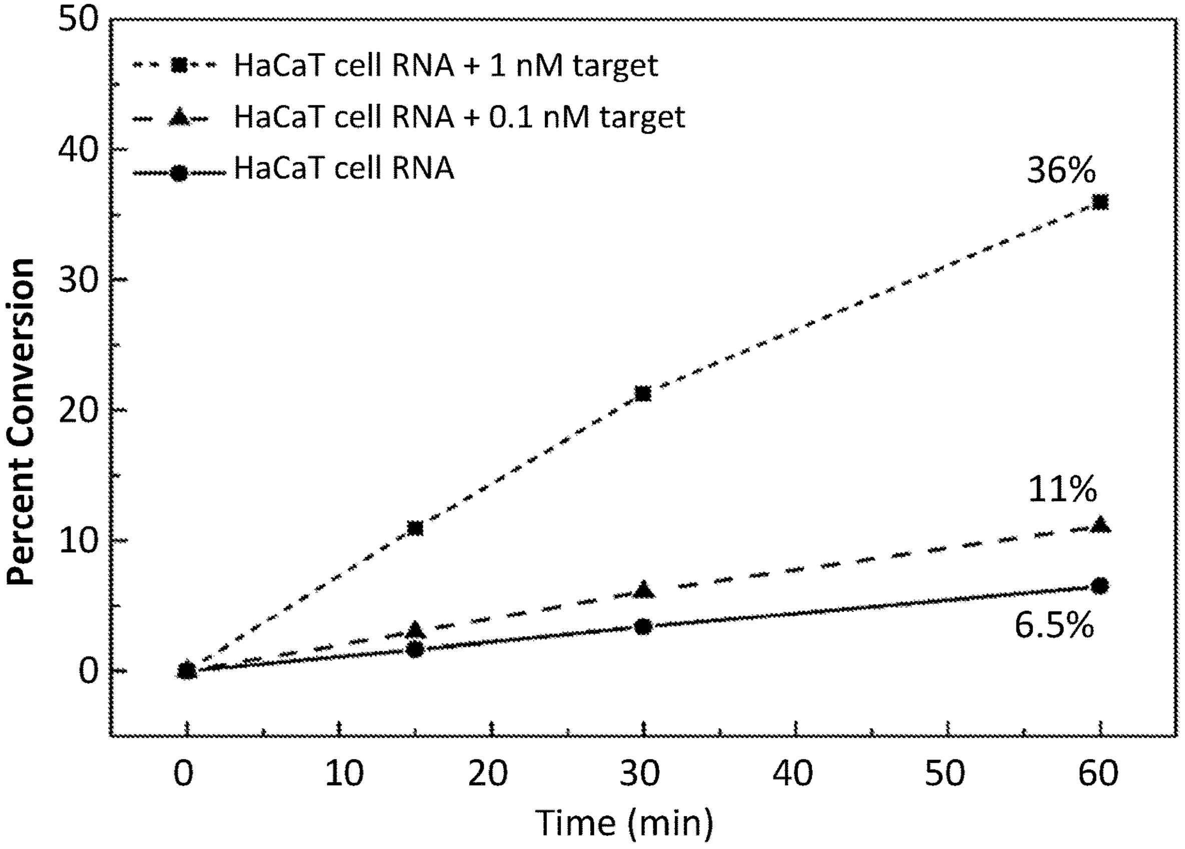

In some embodiments, the probe pair comprises PNA probes (such as a PNA HIV-1 Pol/Int probe pair or PNA HIV-1 TAR probe pair) to detect a target RNA sequence. PNA probe pairs have been reported in the literature for OTP detection of DNA templates (non-HIV-1 sequences) (Röthlingshöfer et al., *Organic Lett.* 2012, 14 (2), 482-485). PNA probes were shown to demonstrate specificity toward short DNA sequences, but showed nonspecific interactions with long DNA negative controls (both in vitro transcribed in FIG. 13A and cell-extracted DNAs not containing the target sequence in FIG. 3B), especially in the case of unmodified PNA probes. Thus, the PNA-PNA probe sets likely require significant modifications to facilitate detection of RNA target sequences in complex RNA. PNA-PNA probes with hydrophilic modifications significantly reduced but did not eliminate nonspecific DNA interactions. In developing the compositions, kits, and assays described herein, a range of reaction conditions were studied, including different buffer concentrations and types, detergent concentrations and types, and additives such as DMSO, formamide, betaine, spermidine, and detergents, as well as changes to PNA probe sequences and lengths, and certain, non-obvious adjustments significantly improved the sensitivity of the reaction and/or reduced the background signal of the reaction. These changes were found to be required for sensitive detection of the target RNA sequence in a complex RNA solution isolated from cells.

Figure 13A:
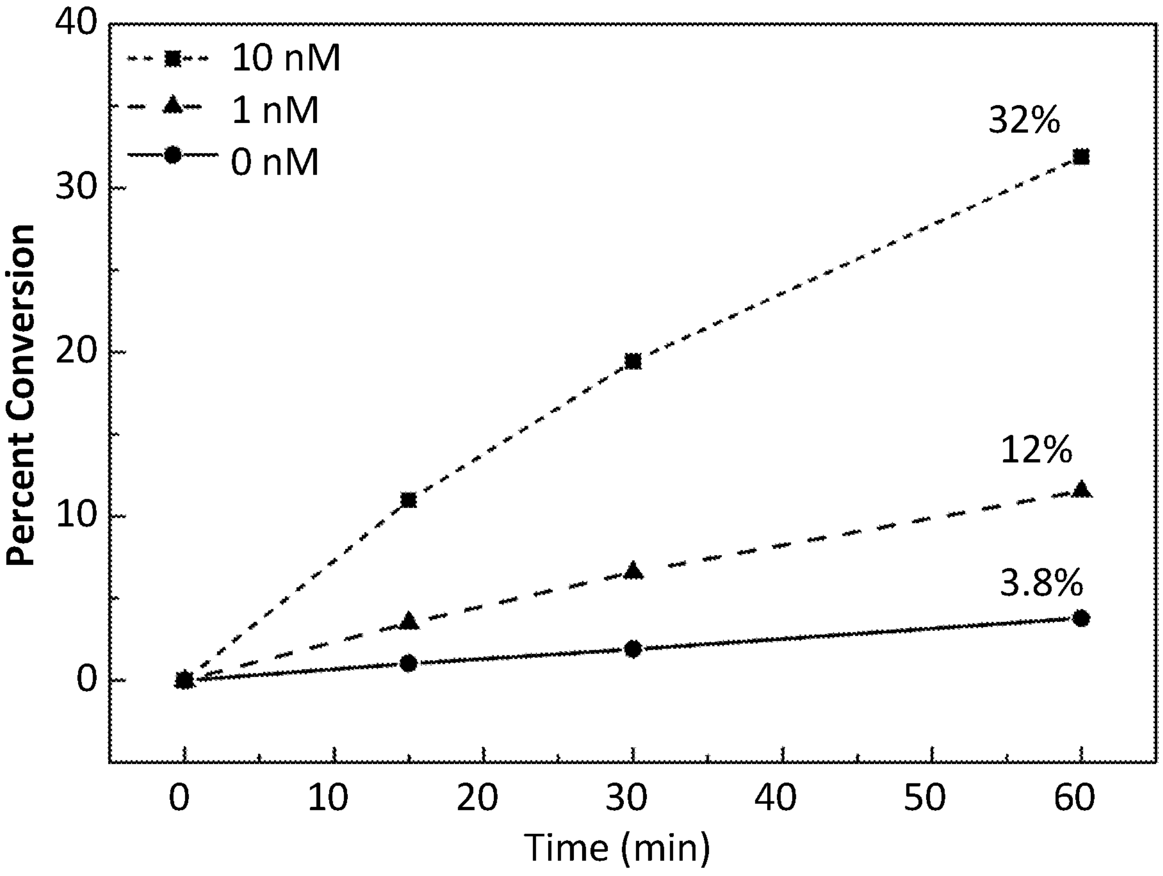
FIGS. 13A-13B show the difference in specificity between PNA-PNA and DNA-DNA probe sets for negative control in vitro-transcribed RNA, as described in 11-1. The PNA-PNA OTP probe set detected false positives (FIG. 13A) while the DNA-DNA OTP probe sets did not (FIG. 13B).
Figure 13B:
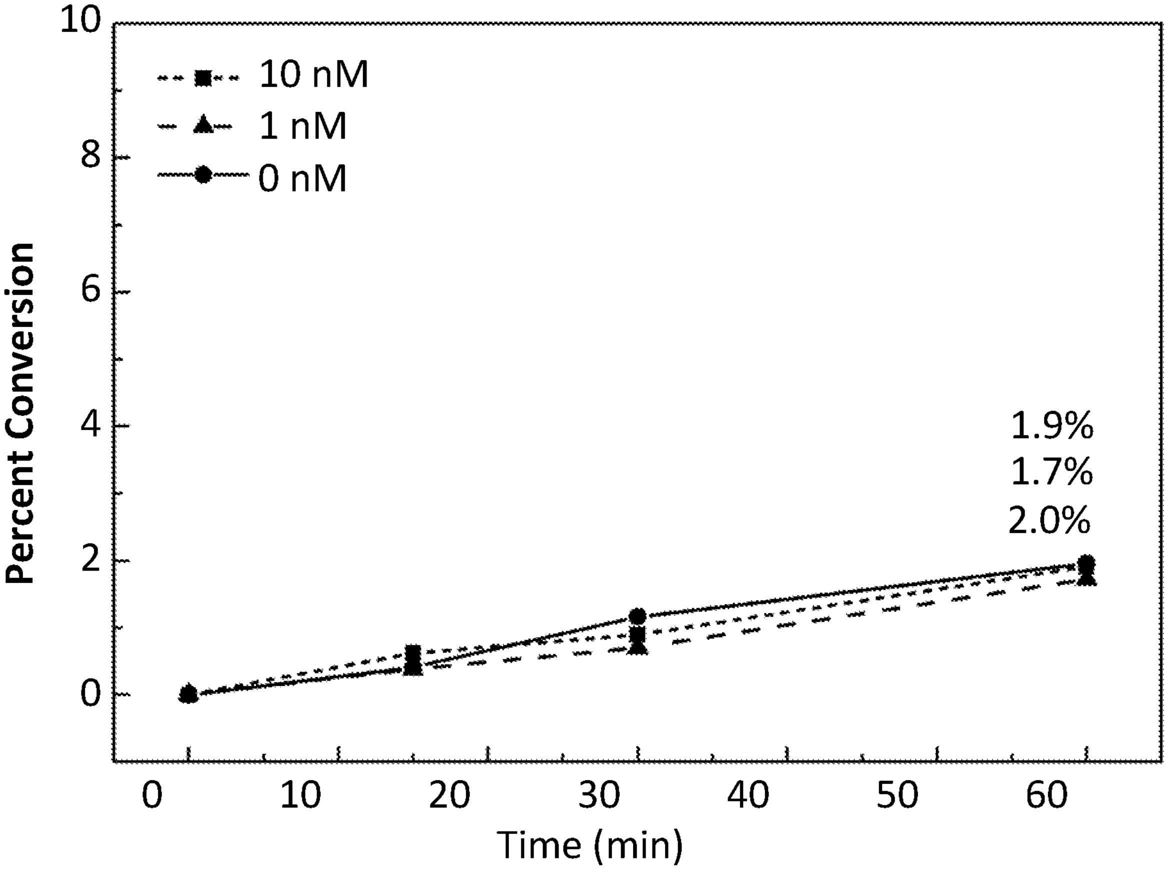

To further reduce background and improve reaction sensitivity, DNA-DNA and PNA-DNA probe pairs were developed, which are less likely to form nonspecific interactions with RNA. Thus, in some embodiments, the probe pairs comprise two DNA probes, or one PNA probe and one DNA probe. In the examples presented, the use of DNA-DNA vs. DNA-PNA vs. PNA-PNA probe sets were experimentally tested. For RNA detection, as shown in FIGS. 13A and 13B, DNA-DNA probe pairs generally provided much better specificity, compared to PNA-PNA probe pairs targeting the same RNA sequence.

A PNA or DNA "opener" as used herein is a PNA or DNA sequence that is complementary to a target RNA sequence region that has secondary structure, particularly a tightly-ordered secondary structure, such as a hairpin, stem portion of a stem-loop, or pseudoknot. The opener invades and competes with inter-strand hydrogen-bonds to open or partially open the RNA secondary structure to allow for probe hybridization to a nearby target RNA sequence. The opener sequences are not complementary to either the photocatalyst probe or the profluorophore probe. In some embodiments, a PNA opener is functionalized at one or more gamma peptide backbone positions with a relatively bulky hydrophilic moiety, such as diethylene glycol (miniPEG) (e.g., as in structure (A), (B), or (C) herein), which increases solubility in aqueous solution and hybridization to the target RNA sequences. PNA openers can be more effective than DNA openers, as the PNA binds with a higher $T_m$ to the target RNA sequence, given equal number of nucleotides in the opener. Additionally, either a DNA or a PNA opener can bind to the RNA complementary sequence within an RNA hairpin, stem-loop, or other RNA secondary structure with a higher $T_m$ than the RNA secondary structure, because often there are natural mismatches within such secondary structures and the opener is designed for perfect complementarity. A PNA opener may also be shorter in length compared to a DNA opener, which can be an important consideration for both possible sequence conservation limitations and for the length of the RNA sequence itself. In the case of HIV-1 TAR RNA, the sequence is only 59-61 nucleotides in length, which constrains the length of any opener employed, to prevent overlap with either of the OTP probes used. Further, as RNA secondary structures are often estimates and may be changed into different secondary structures by denaturation or partial denaturation, experimental testing to identify effective openers is essential. Examples of openers include SEQ ID NO: 30 (a DNA opener) and 31 (a PNA opener) (Table 1). Figures in Examples 1 and 2 show the remarkable effect of a PNA opener, when combined with an initial denaturation and annealing step to allow opening of the RNA secondary structure and annealing of the PNA opener to the structure, which promoted a one-to three-fold increase in reaction efficiency.

Figure 6A:
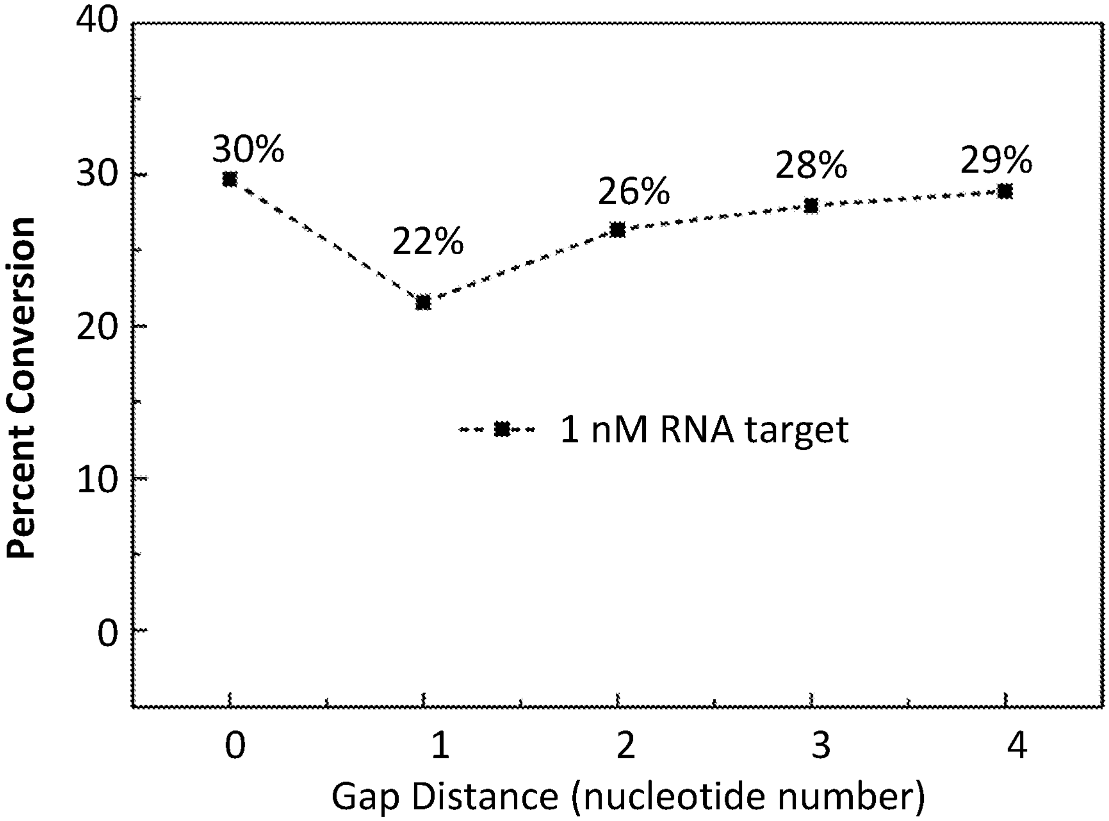
FIGS. 6A-6B show that template gap did not change the reaction outcome significantly for DNA-DNA OTP probe pairs targeting HIV-1 Pol/Int RNA (FIG. 6A), but did make a large difference in reaction outcome for PNA-PNA OTP probe pairs targeting HIV-1 TAR RNA (FIG. 6B).
Figure 6B:
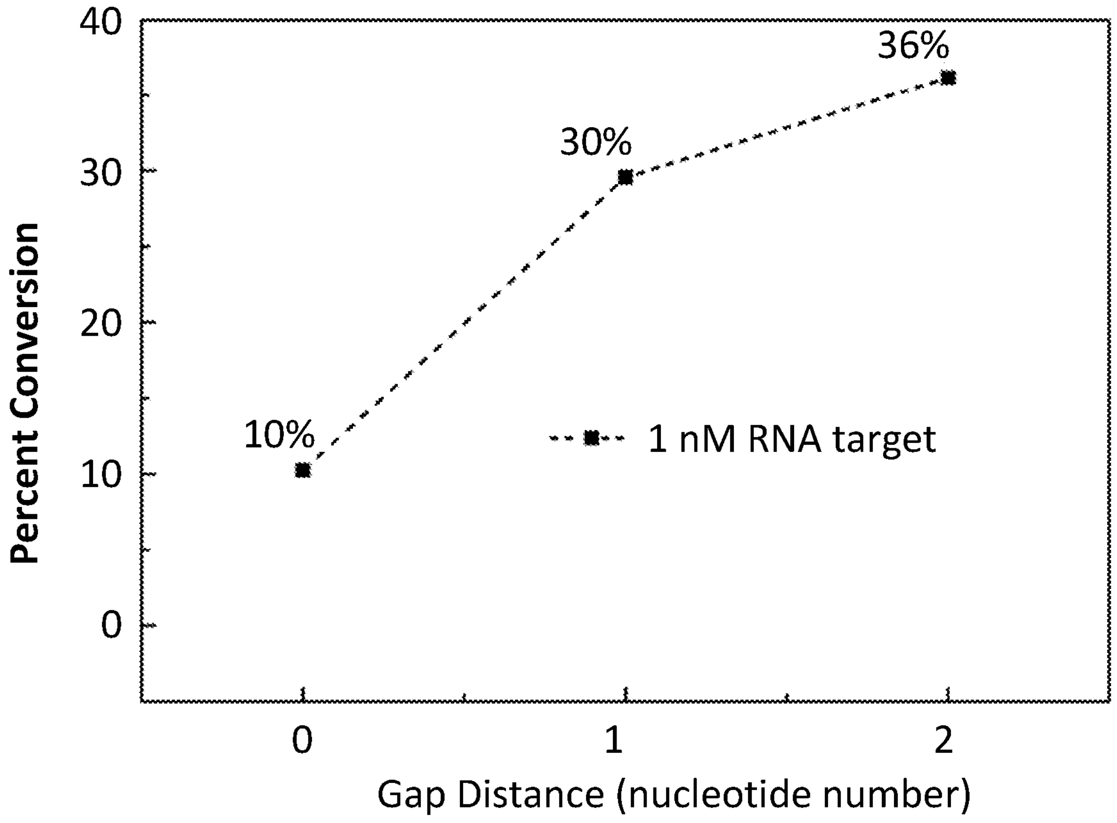
Figure 8:
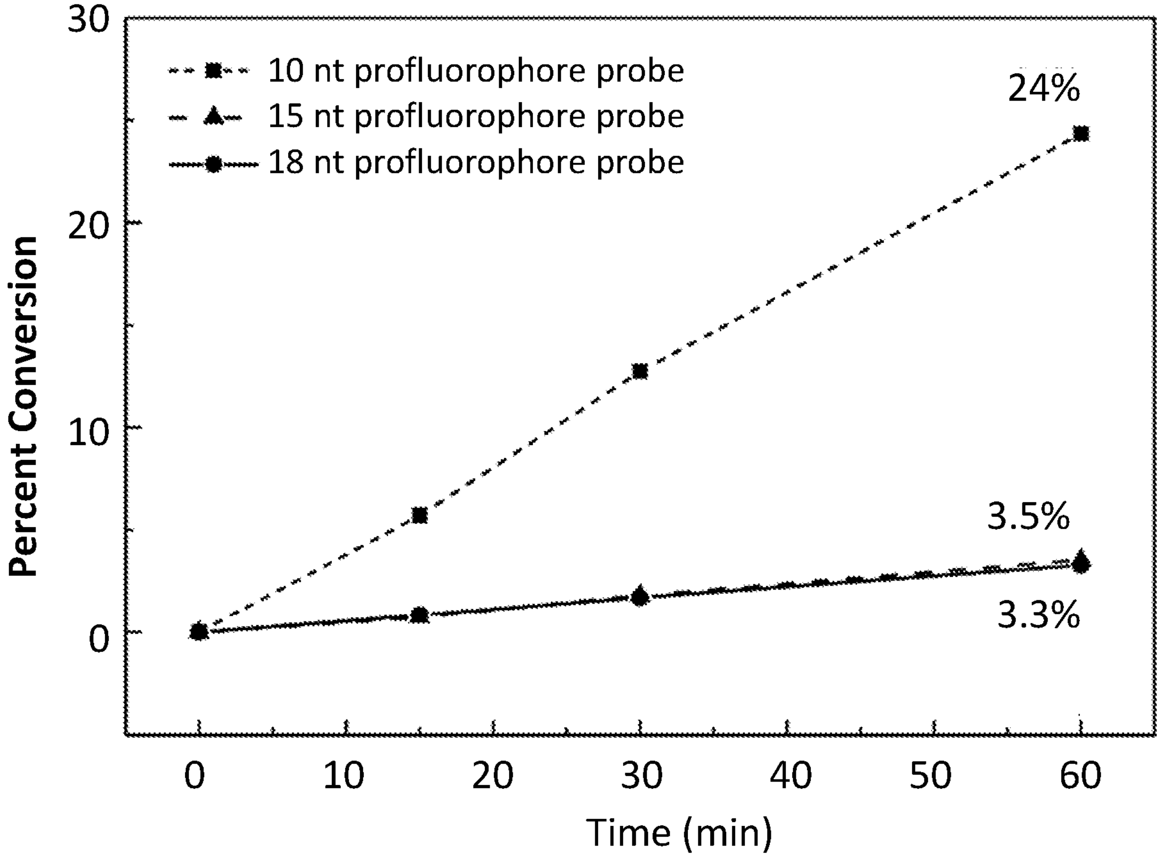
FIG. 8 shows the effect of profluorophore probe length on OTP reaction yield.
Figure 9A:
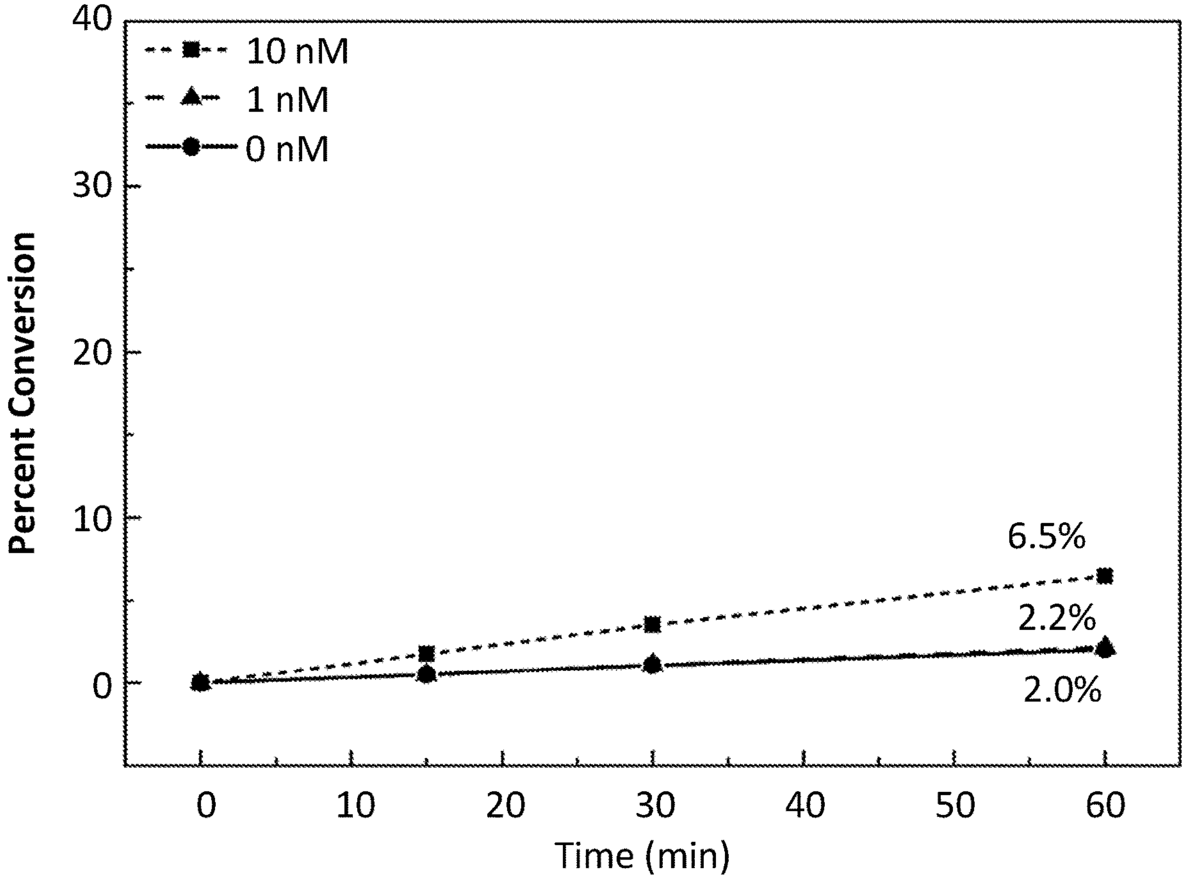
FIG. 9A-9B show 1×PBS buffer does not support DNA-DNA OTP probe set detection of 1 nM HIV-1 TAR RNA (FIG. 9A) while 5×PBS buffer does support DNA-DNA OTP probe set detection of 1 nM HIV-1 TAR RNA (FIG. 9B).
Figure 9B:
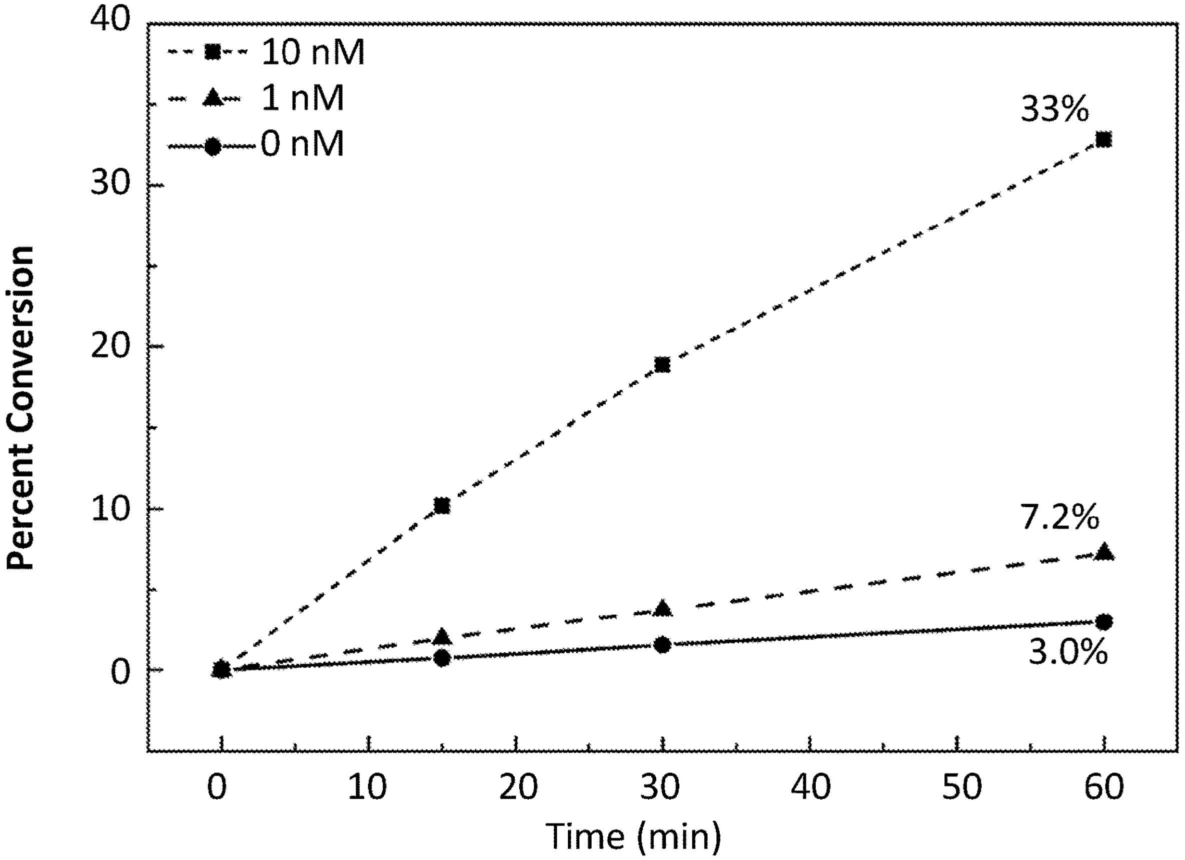
Figure 10A:
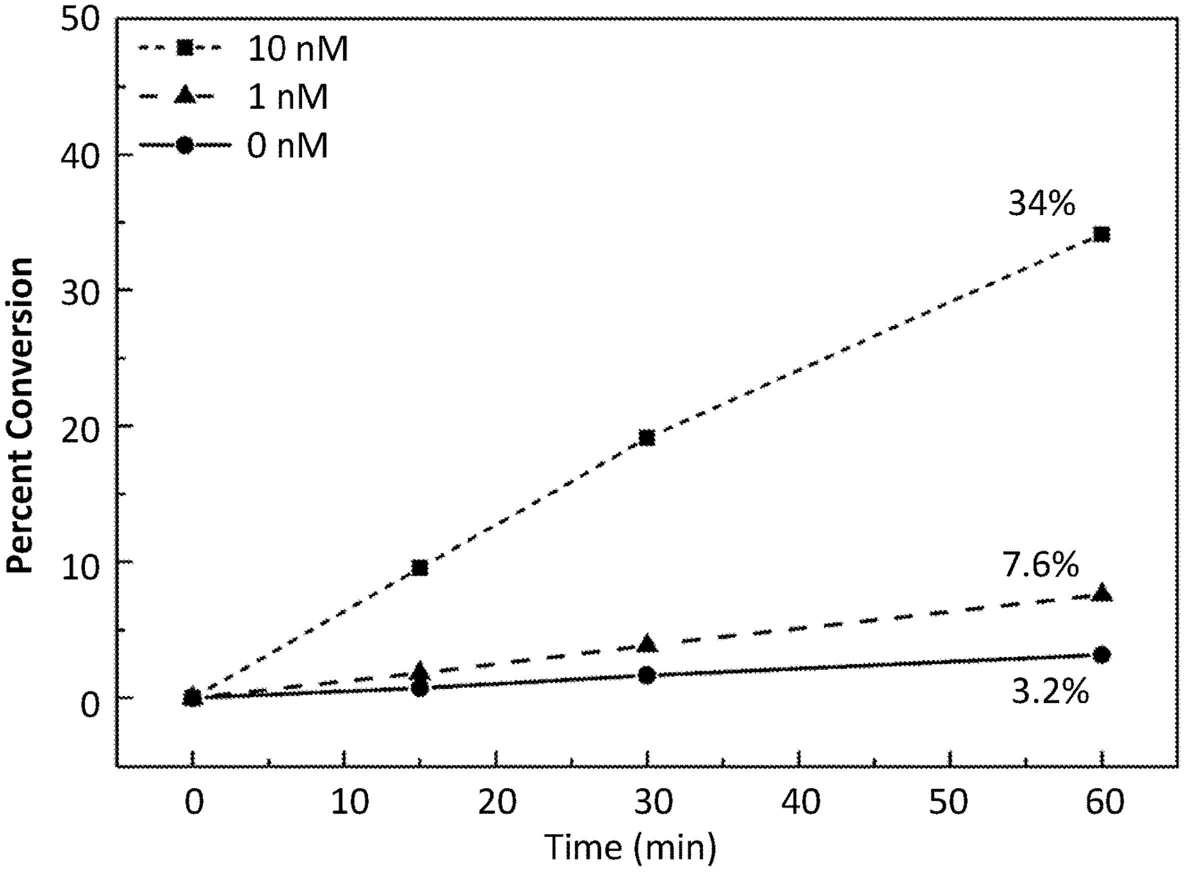
FIGS. 10A-10B show 1×PBS buffer with PNA-PNA OTP probe set does not provide optimal detection of HIV-1 TAR RNA (FIG. 10A) while 0.1×PBS buffer with PNA-PNA OTP probe set does provide improved detection of HIV-1 TAR RNA (FIG. 10B).
Figure 10B:
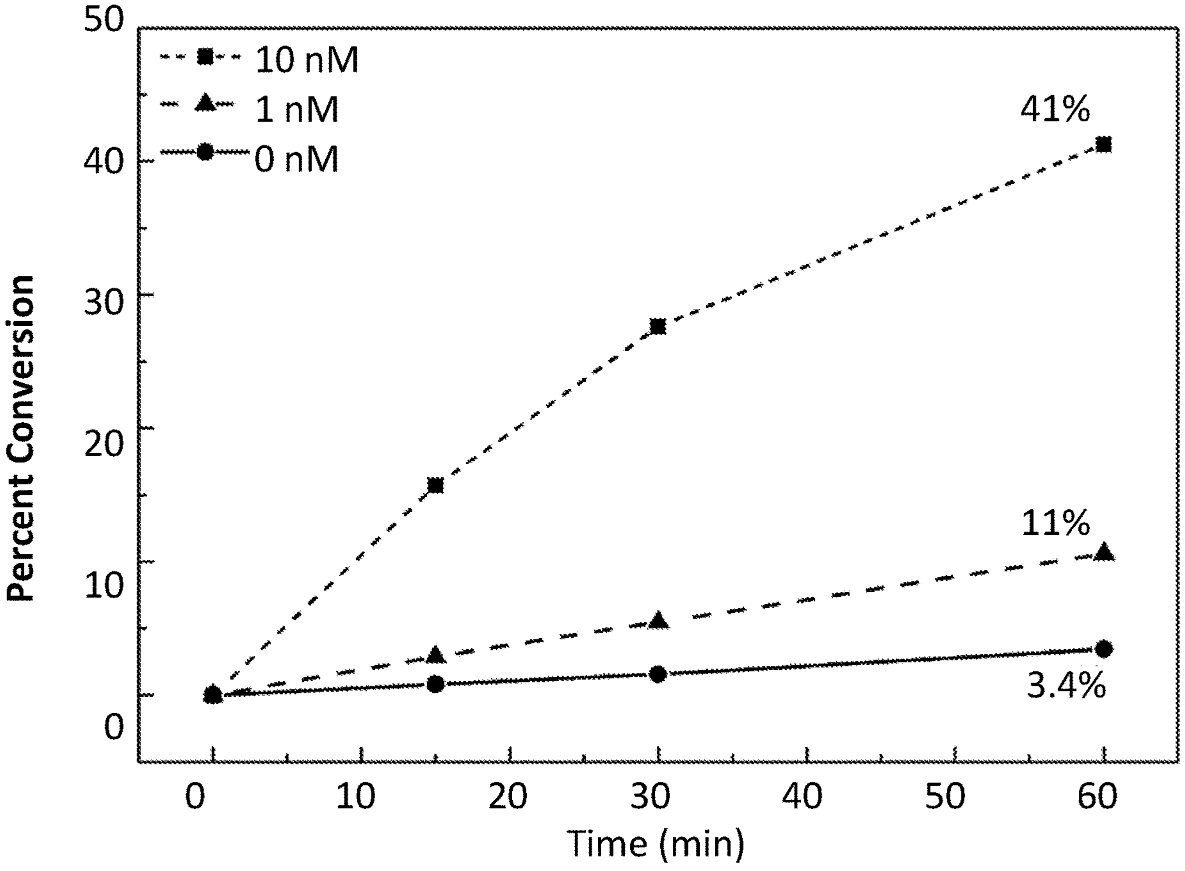

In some embodiments, the probe pair comprises PNA probes, and (1) the photocatalyst PNA concentration is about 25 nM or 50 nM, (2) the profluorophore probe concentration is about 100 nM, and (3) the assay background reaction is detected at about 3% to 4%. Assay conditions were tested, including buffer concentration, additives, probe gap on the template, RNA target sequence, and length of the probes (e.g., HIV-1 Pol/Int profluorophore PNA probe was tested at 6, 7, and 8 nucleotides) on the rate of the reaction. Buffer concentration was found to have a large effect, with the optimal buffer concentration significantly different between PNA-PNA, PNA-DNA and DNA-DNA probe pairs, and also significantly different depending on the RNA target sequence. For a PNA-PNA probe pair targeting HIV-1 Pol/Int RNA, the best buffer concentration was 0.05×PBS, while the best buffer concentration for a DNA-DNA probe pair targeting the same sequence was 1×PBS. For a PNA-PNA probe pair targeting HIV-1 TAR RNA, the best buffer concentration was 0.1×PBS (FIG. 10), while the best buffer concentration for both PNA-DNA and DNA-DNA probe pairs targeting the same HIV-1 TAR RNA sequence was 5×PBS (FIG. 9). Template gap did not change the reaction outcome significantly for DNA-DNA probe pairs targeting HIV-1 Pol/Int (FIG. 6A), but did make a big difference in reaction outcome for PNA-PNA probe pairs targeting HIV-1 TAR (FIG. 6B). We did not find most of the obvious additives, including those typically used in DNA templated enzymatic reactions, to improve the reaction outcome, with the exception of a detergent, polysorbate 20 (polyoxyethylene-20-sorbitan monolaurate), at a concentration of 0.05%. The length of the profluorophore, whether PNA or DNA, made a large difference in turnover number and thus in reaction signal (FIG. 8). The photocatalyst probe optimal length was 10-12 nucleotides for PNA and 18-21 nucleotides for DNA to allow for stable binding to the target (template) sequence. The profluorophore probe optimal length in most cases was 8 nucleotides for PNA and 10 nucleotides for DNA, after testing 18, 15, 13, 11, 10, 8, 7, and 6 nucleotides, for both a high turnover at a 25° C. isothermal reaction temperature and for binding specificity to the target RNA sequence.

In some embodiments, the probe pair comprises DNA probes. In DNA probes, the sequence was the same as for the PNA probe, but the backbone of the probe was phosphate-2-deoxyribose, and the length of the probe was increased by up to 10 nucleotide bases to compensate for the lower binding affinity of DNA to RNA compared to PNA to RNA. In some embodiments, the probe pair comprises DNA probes and the target sequence is HIV-1 Pol/Int. In some embodiments, the DNA probe pair (such as the DNA Pol/Int Probe Pair described herein) provided a lower background reaction (1.5-2%), 5-fold less non-specific reaction (higher selectivity), and lower template detection limit (higher sensitivity) compared to the corresponding PNA-PNA probe pair targeting the same Pol/Int HIV-1 RNA sequence.

In some embodiments, the probe pair is a PNA probe pair, a DNA probe pair, or a PNA-DNA probe pair, and the target sequence is HIV-1 TAR. In some embodiments, the probe pair is a PNA-DNA probe pair or a PNA-PNA probe pair. In some embodiments, the profluorophore probe is DNA- or PNA-Azido-Coumarin. In some embodiments, the profluorophore probe is DNA- or PNA-Pyridinium-Fluorescein. In some embodiments, the photocatalyst probe is DNA or PNA Ru.

Figure 12A:
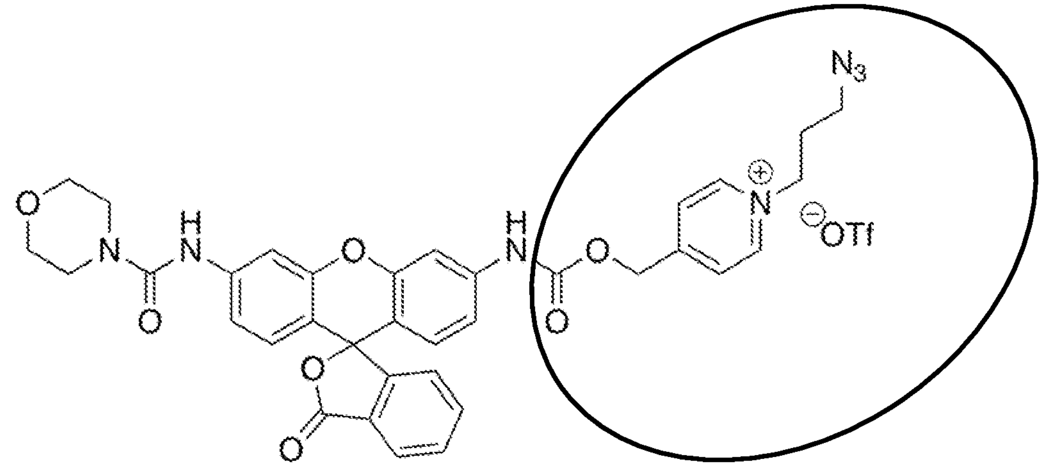
FIGS. 12A-12B show two profluorophores incorporating self-immolative linkers, with FIG. 12A showing structure (M) and FIG. 12B showing structure (N). The self-immolative linkers are shown circled in the profluorophore structures, as described in Example 12. For FIG. 12A, the resulting fluorophore ends with an amine (—$NH_2$), after release of carbon dioxide (CO2) and the remainder of the linker. For FIG. 12B, the resulting fluorophore ends with a hydroxyl (—OH), after release of the linker.
Figure 12B:
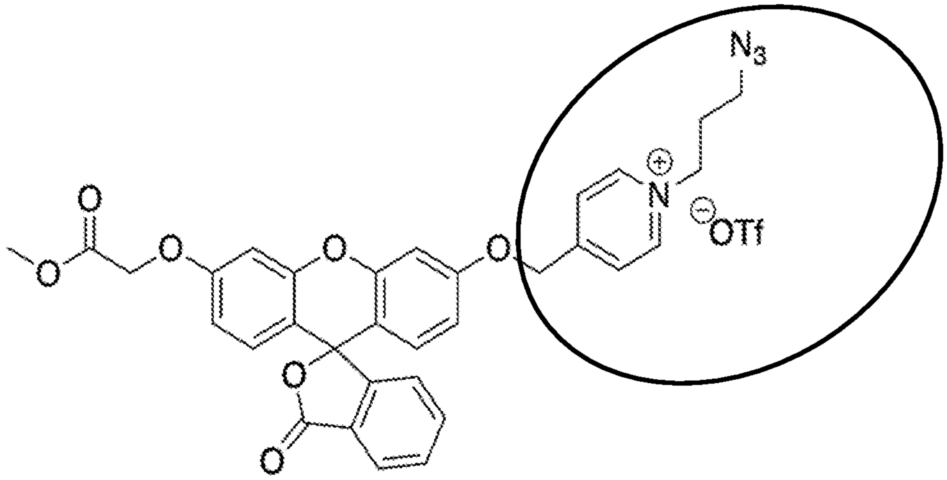

A single probe may comprise a DNA or PNA oligonucleotide covalently bound to a photocatalyst or a profluorophore at either the 5' or 3' end. In some embodiments, the DNA or PNA oligonucleotide is covalently bound to a profluorophore through a self-immolative linker that releases the resulting fluorophore from the profluorophore probe during the reduction reaction catalyzed by the activated photocatalyst on the second DNA or PNA oligonucleotide. FIGS. 12A and 12B show profluorophores incorporating a self-immolative linker (with the linker shown in a circle).

2. Sequence Design of Oligonucleotide Probes

The sequence design of oligonucleotide probes may be based on the sequence of the target of interest. To design sequences for probes for detection of nonlinear RNA sequences, the following protocol may be employed.

First, if the RNA sequence is known to contain stable secondary structures, such as a hairpin or pseudoknot, complementary sequences may be chosen to the 5' and 3' regions on either side of the secondary structure (one probe on the 5' side and the other probe on the 3' side). Alternatively, one or both of the probe sequences may be complementary to sequences within a hairpin, including within any bulge or loop elements and/or within the stem of the hairpin. It is helpful if at least one of the probes binds to a relatively single-stranded portion of an RNA sequence containing a stable secondary structure, but in every case, complementary sequences between the two probe sequences is to be avoided, particularly 3 or greater complementary bases between PNA probes. If PNA-based probes are used, the PNA may be able to enter into stable triplex interactions within the stem of a hairpin, a process that may be facilitated by partial denaturation at a temperature above the annealing temperature of the hairpin or other secondary structure containing a double-stranded RNA, followed by return to a temperature below the annealing temperature of the PNA to its complementary sequence within the RNA target sequence structure.

Second, if nonlinear structures of an RNA sequence have not previously been identified, thermodynamically stable nonlinear structures of the RNA sequence may be mapped using online software programs using a dynamic programming algorithm based on free energy calculations that are widely used to search for RNA nonlinear structures. In some instances, the most thermodynamically stable structure may be chosen. These programs can be augmented by additional calculations based on experimental determinations. After mapping of the likely secondary structures, probe sequences may be chosen as described in the immediately preceding paragraph for hairpins (stem-loops), pseudoknots, and other RNA secondary structures, or to target single-stranded (linear) RNA sequence regions.

In some embodiments, the base sequence of each probe in a probe pair may be perfectly complementary or partially complementary to a target sequence of the template, and may include degenerate sequence to allow for template sequence variation. In some embodiments, allowable sequence variation is 5-25%.

In some embodiments, the sequence variation tolerated depends on the sequence length and probe backbone, with greater variation tolerated for longer sequences and DNA probe backbones and less variation tolerated for shorter sequences and PNA or other modified probe backbones. A probe sequence length of 10 nucleotides or less can tolerate a one-to two-nucleotide variation while a sequence length of 11-21 nucleotides can tolerate a one- or four-nucleotide variation. Thus, variation in probe sequences may occur at 1, 2, 3, 4, 5, 6, 7, 8, 9, or 10 nucleotides for a probe sequence of up to 40 nucleotides, as compared to sequences provided herein and as compared to the exact complement in a target sequence.

In some embodiments, the sequence variation in probe target sequence tolerated depends on the location of the sequence variation, such that variation nearer to or at the ends of the probe binding sequence affect probe binding to target sequence greater than variations more central to the probe binding sequence. In some embodiments, longer or alternative (shifted down- or upstream from a particular target sequence location) probe sequences can be employed to prevent loss of binding affinity to a target sequence of known variation. Probes degenerate at particular positions may also be used to enhance binding when more than one sequence variant may be present.

The use of probe sequences from 5 to 30 nucleotides or from 5 to 40 nucleotides may be used in order to maximize efficiency and multiplex detection. Multiple sets of different probes, each complementary to a different target sequence, within one or more of the same or different RNA templates, may be used in the same or tandem reactions for multiplex detection of target sequences. Probes shorter in length than 5 nucleotides or longer in length than 40 nucleotides may not be appropriate in all embodiments.

In some embodiments, the oligonucleotide probes in a pair are each independently from 5 to 50 nucleotides long, or from 5 to 40 nucleotides long, or from 5 to 30 nucleotides long, or from 18 to 21 nucleotides long, or from 8 to 15 nucleotides long, or are independently 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, the photocatalyst probe is a PNA probe and is from 7 to 13, or from 8 to 12, or 8, 9, 10, 11, or 12 nucleotides long. In some embodiments, the photocatalyst probe is a PNA probe and is 10 nucleotides long. In some embodiments, the photocatalyst probe is a DNA probe and is from 15 to 30, or from 16 to 28, or from 16 to 25, or 16, 17, 18, 19, 20, 21, 23, 23, or 24 nucleotides long. In some embodiments, the photocatalyst probe is a DNA probe and is 18 to 21 nucleotides long. In some embodiments, the profluorophore probe is a PNA probe and is from 5 to 15, or from 7 to 13, or 6, 7, 8, 9, 10, 11, or 12 nucleotides long. In some embodiments, the profluorophore probe is a PNA probe and is 8 nucleotides long. In some embodiments, the profluorophore probe is a DNA probe and is from 5 to 25, or from 7 to 13, or from 8 to 12, or 8, 9, 10, 11, or 12 nucleotides long, or is from 8 to 20, or from 9 to 19, or 10, 11, 12, 13, 14, 15, 16, 17, 18, 19, or 20 nucleotides long. In some embodiments, the profluorophore probe is a DNA probe and is 10 nucleotides long.

In some embodiments, the photocatalyst probe comprises an oligonucleotide sequence with a melting temperature (Tm) to the target RNA sequence that allows the photocatalyst probe to remain in place through more than one catalytic cycle at one or more of the OTP reaction temperature/s, i.e., a Tm of at least 5-10° C. above the reaction temperature/s. In some embodiments, the profluorophore probe comprises an oligonucleotide sequence with a Tm to the target RNA sequence that allows for release of the fluorophore probe from the target sequence and binding of an unreacted profluorophore probe after one catalytic cycle, at one or more of the OTP reaction temperature/s, i.e., a Tm of not more than 5° C. above one or more of the reaction temperature/s and ideally a Tm of less than 5° C. above one or more of the reaction temperature/s, including a Tm of the same or below one or both of the reaction temperature/s.

Sequences for the probes may be chosen such that the two probes to bind in sufficient proximity (the gap distance) that the reduced, activated photocatalyst can react with the profluorophore when both probes of the probe pair hybridize to the target RNA sequence.

In some embodiments, sufficient proximity (the gap distance) is from about 2.5 to about 29.6 angstroms, approximately corresponding to 1 to 8 nucleotides between the proximal probe ends, or from about 7.5 to about 18.5 angstroms, approximately corresponding to 3 to 5 nucleotides between the proximal probe ends. One of ordinary skill will understand that numeric assignment of gap distances in terms of angstrom units or number of nucleotides is provided as a general guideline illustrating such gap distances within ranges that are neither so small as to inhibit the photoreduction reaction between the photocatalyst and the profluorophore, nor so large that the photocatalyst and profluorophore are too far apart to effectively interact with each other, when both probes in the probe pair hybridize to the target RNA sequence. Gap distances are not, however, intended as parameters that require actual physical measurement. Further as noted above, the adequacy of a gap distance for particular probe pairs hybridizing to a given target RNA sequence may be ascertained situationally by optimizing fluorescence output and reaction time.

In some embodiments, the probes may hybridize adjacently on the target RNA sequence, leaving no template sequence gap between the probes. In other embodiments, hybridization of the probes to the target RNA leaves a sequence gap of the target RNA between the hybridized probes. In some embodiments, if the target RNA is linear, the upstream and downstream portions of the target RNA sequence are separated by a gap of up to 8 nucleotides of the target RNA sequence corresponding to the gap between the probes. In some embodiments, the binding of the probes of the probe pair to the target RNA sequence leaves a single-stranded gap of 0 to 8 nucleotides of the target RNA sequence between the bound probes. In some embodiments, the gap distance is 0, 1, 2, 3, 4, 5, 6, 7, 8, 9, or 10 nucleotides. In some embodiments, the gap is from 0 to 7 nucleotides, optionally wherein the two probes in the pair are DNA probes or one probe in the pair is a DNA probe and the other probe is a PNA probe, or the gap is 1 to 7 nucleotides, optionally wherein the two probes in the pair are PNA probes. In some embodiments, the gap is 1, 2, 3, or 4 nucleotides. In some embodiments, the gap is 1 or 3 nucleotides. In some embodiments, the gap is 2 nucleotides and the target RNA is HIV-1 TAR. In some embodiments, the gap is 0 to 2 nucleotides and the target RNA is HIV-1 Pol/Int. In some embodiments, the gap is 2 nucleotides and the target RNA is HIV-1 Pol/Int.

3. Targets for Oligonucleotide Probes

Target sequences for the probe pairs described herein include any RNA target sequence, across a range of structure types and biological sources. In some embodiments, the target RNA sequence is single-stranded RNA. In some embodiments, the target RNA sequence is RNA with secondary, tertiary, or quaternary structure, or linear RNA sequence containing neither a spliced site nor RNA secondary structure. In some embodiments, the target RNA sequence is part of a relatively linear RNA secondary structure, such as HIV-1 Pol/Int. In some embodiments, the target RNA sequence is part of a secondary structure, such as HIV-1 TAR. In some embodiments, a target RNA sequence contains a spliced site resulting from a splicing event. In some embodiments, the target RNA is spliced CD4+ RNA. In some embodiments, the method can detect a target sequence so as to identify the presence or absence of a mutation in RNA or an RNA spliced product or splicing product. In some embodiments, a target RNA sequence contains a stem-loop or hairpin secondary structure. In some embodiments, a target RNA sequence contains an RNA pseudoknot. In some embodiments, a target RNA sequence contains neither a spliced site, pseudoknot, hairpin, nor a stem-loop. In some embodiments, the target sequence is in vitro transcribed RNA or cellular RNA. In some embodiments, the target RNA sequence is a spliced RNA or an RNA secondary structure relevant to a broad range of disease, developmental, structural, epidemiological, environmental, and evolutionary contexts. In some embodiments, the method can detect a target sequence with up to 5-25% variation in the target sequence.

In some embodiments, the target RNA sequence is viral, bacterial, mammalian, other animal, plant, fungal, protozoal, or archaebacterial RNA.

In some embodiments, the target RNA sequence is viral RNA. In some embodiments, the viral RNA is from a virus selected from an RNA virus, a retrovirus, a flavivirus, and a coronavirus. In some embodiments the viral RNA is from an RNA virus or a retrovirus. In some embodiments, the viral RNA is from a virus selected from HIV-1, HIV-2, Ebola hemorrhagic fever, SARS, influenza (such as influenza A), hepatitis C, West Nile, polio, measles, CMV, Herpes, Zika, Norwalk, yellow fever, dengue, Lassa, Rift Valley fever, Chikungunya, Hantavirus, Marburg, Ebola hemorrhagic fever, Nipah, Rubella, Canine Influenza, HoBi-like pestivirus, Schmallenberg, Simian immunodeficiency (SIV), Powassan, Hepatitis E, Canine hepacivirus, Colorado tick fever, Theiler's disease associated, Ross River, Barmah Forest, MERS-COV, and SARS-COV-2 (also named Coronavirus 2019-nCOV, which causes COVID-19) viruses. In some embodiments, the viral RNA is from a virus selected from HIV-1, HIV-2, Ebola hemorrhagic fever, SARS, influenza, hepatitis C, West Nile, polio, measles, CMV, Herpes, Zika, Norwalk, yellow fever, dengue, MERS-COV, and SARS-COV-2 (also named Coronavirus 2019-nCOV, which causes COVID-19) viruses.

In some embodiments, the viral RNA is from HIV-1 or HIV-2. In some embodiments, the target RNA sequence is HIV-1 Pol/Int or HIV-1 TAR. In some embodiments, the target RNA sequence is located within full-length (9 kb), 1, 2, 4 kb, or other size spliced HIV-1 RNA.

Figure 11:
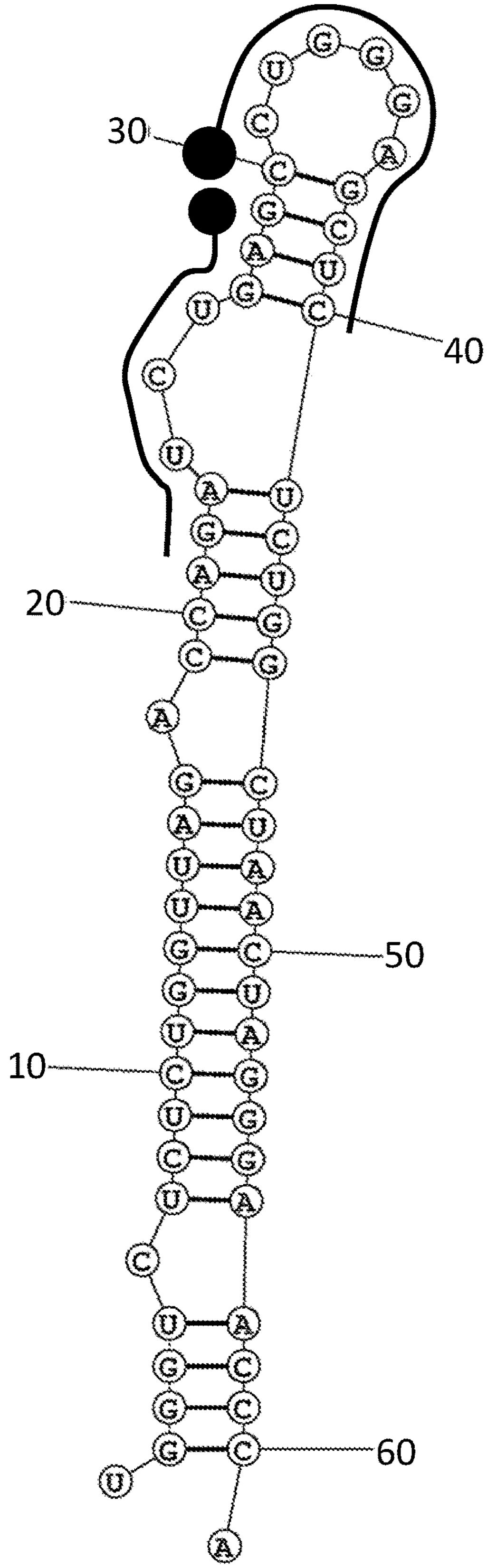
FIG. 11 is a schematic of the secondary structure of HIV-1 TAR RNA (SEQ ID NO: 23) with an OTP probe pair hybridized to the stem loop region, where the lower ball shown is the profluorophore attached to the profluorophore probe and the upper ball shown is the photocatalyst attached to the protocatalyst probe, as described in Example 11.

In an exemplary embodiment, pairs of fluorogenic oligonucleotide probes are engineered to provide superior stability and specific RNA sequence detection for quantifying low levels of target RNA sequences in test samples. In some embodiments, the target RNA is HIV-1 RNA. In some embodiments, the target RNA is RNA in the deep-latent and/or activated HIV-1 LR. In some embodiments, the target RNA sequence is HIV-1 Pol/Int and/or HIV-1 TAR. In some embodiments, at least one PNA probe or DNA or PNA opener is used to facilitate efficient entry into the stable TAR secondary structure. In some embodiments, one or both of the probe pair fully or partially targets the loop or single-stranded regions of the TAR secondary structure (FIG. 11).

RNA targets other than viruses may also be detected. RNA levels in cells that are of interest may also be targeted. In some embodiments, the target RNA sequence is from bacteria. In some embodiments, the bacterium is *Borrelia burgdorferi, Mycobacterium tuberculosis, Coxiella burnetii, Neisseria gonorrhoeae, Chlamydia trachomatis, Mycoplasma genitalium, Trichomonas vaginalis*, Group A streptococci, *Helicobacter pylori, Salmonella typhi, Leptospira* bacteria, *Leptospira interrogans* serovars, *Rickettsia* bacteria, or *Orientia tsutsugamushi* bacteria. In some embodiments, the bacteria is borne by an arthropod vector such as ticks, mites, or other, such as *Borrelia burgdorferi, Rickettsia* bacteria, or *Orientia tsutsugamushi.*

In some embodiments, the target RNA sequence is mammalian RNA. In some embodiments, the mammalian RNA is a spliced RNA variant. Other applications include unspliced RNAs, microRNAs (miRNA), circular RNAs (circRNA), and long noncoding RNAs (lncRNA), some of which are indicative of medically important conditions, genetics, or transcriptional states. A nonexhaustive list of examples of spliced sites or RNA level targets implicated in disease is provided in Table 2. Any RNA of interest may be detected using this composition or kit and method.

TABLE 2

RNA spliced sites or change in level implicated in human disease.

| Human Gene | Diseases/Conditions | Relevant Spliced Sites or Level |
|---|---|---|
| CD46 | Immune deficiency, multiple sclerosis, rheumatoid arthritis, asthma, cancer, *Neisseria* bacterial infection, Measles virus | Spliced sites including or excluding Exons 7, 8, 9, 13, 14 |
| Klotho | Premature aging, chronic kidney disease | Transmembrane form with spliced Exons 3-4, 4-5, and lacking intron region following Exon 3 |
| DENND1A | Polycystic ovary syndrome | Variant 2 (V2) |
| BC200 lncRNA | Breast cancer | Higher BC200 lncRNA level |
| DN RBFOX2 | Diabetic cardiomyopathy | Dominant negative (DN) isoform |
| SF3B1 | Myelodysplastic syndromes | Cryptic 3' spliced site usage |
| BRCA1 | Resistance to PARP Inhibition and Cisplatin | BRCA1-Δ11q |
| ITGB4, PYCR1 | Non-Small Cell Lung Cancer | Splice variants of ITGB4, PYCR1 |
| CD44 | Melanoma | CD44v8-10 |

Thus, in some embodiments, the target RNA sequence is selected from CD46 (e.g., spliced sites including or excluding Exons 7, 8, 9, 13, and 14), Klotho (e.g., transmembrane form with spliced Exons 3-4 and 4-5, and lacking intron region following Exon 3), DENNDIA (e.g., Variant 2 (V2)), BC200-lncRNA, Dominant negative (DN)-RBFOX2 isoform, SF3B1 (e.g., cryptic 3' spliced site usage), BRCA1 (e.g., BRCA1-Allq), ITGB4, PYCR1, and CD44 (e.g., CD44v8-10). In some embodiments, the mammalian RNA contains RNA secondary structure.

In some embodiments, the compositions and kits can be used in prostate cancer diagnosis and treatment monitoring. Prostate cancer (PCa) is the leading cancer diagnosis for men in the U.S., with a death rate second only to lung cancer for this demographic. Castration-resistant prostate cancer (CRPC), an aggressive PCa, is the result of a switch to androgen-independence, mediated by alternative splicing or other genetic change that removes the androgen-binding domain of the androgen receptor (AR) in prostate cells. With an average life expectancy of 19 months after CRPC diagnosis, there is a critical need for sensitive assays to detect the alternatively spliced versions of the androgen receptor RNA for early diagnosis. PCa drugs in development target AR splice variants or its transcriptional targets, highlighting a great need for companion diagnostics to identify the production of AR splice variants. The developments described herein can meet this need and can be used to directly detect the RNA spliced sites of the two most commonly arising CRPC AR splice variants, ARv7 and ARv567es, which result in deletions of the AR ligand binding domain. This can provide highly sensitive and specific detection in biopsy, circulating tumor cells (CTCs), blood, or urine.

In some embodiments, the target RNA sequence contains an RNA spliced site, and the upstream and downstream portions of the target RNA sequence, to which the probes are designed, span an RNA spliced site, with a distance between the probes of 0 to 8 nucleotides on a linear RNA or a gap consisting of the RNA sequence within a nonlinear structure. In some embodiments, the target RNA sequence contains an RNA hairpin or stem-loop and the upstream and downstream portions of the target RNA sequence, to which the probes are designed, are on either side of (span) or within a hairpin or stem-loop, with a gap between the probes consisting of the RNA sequence within the nonlinear structure. In some embodiments, the target RNA sequence contains another RNA secondary structure, such as a quadruplex structure, including pseudoknots or similar structures, and the upstream and downstream portions of the target RNA sequence, to which the probes are designed, are within or on either side of (span) such a structure, with a gap between the probes consisting of the RNA sequence within the nonlinear structure.

4. HIV-1 Probes

Particular HIV-1 probes and probe pairs are included herein. In some embodiments, the composition or kit quantitatively detects 1 or 2 kb spliced HIV-1 RNA. In some embodiments, the composition or kit quantitatively detects 4 kb spliced and 9 kb full length HIV-1 RNA. In some embodiments, the composition or kit quantitatively detects 9 kb full-length HIV-1 RNA. In some embodiments, the composition or kit quantitatively detects spliced CD4+, CCR5, CXCR4, RPS17, UBE2D2, or other constitutively expressed control RNAs. In some embodiments, the composition or kit quantitatively detects HIV-1 Pol/Int. In some embodiments, the composition or kit quantitatively detects HIV-1 TAR.

Currently available assays for research-only purposes can detect from about 1-30 latent HIV-1-infected cells per 106 white blood cells in peripheral blood, but only after lengthy and repeated activation over a period of 1 to 3 weeks. Further, statistical analysis shows that these assays are highly inaccurate at the high and low ends of this limited range. In contrast, in experimental testing, OTP probe pairs as described herein, which target HIV-1 sites conserved across HIV-1 types, provided direct detection of cellular HIV-1 RNAs, within 24 h of HIV activation. Detection of HIV-1 RNA target sequences using OTP provided the same, quantitative detection when the RNA target sequences were in isolation or when the same RNA target sequences were tested at the same concentration within a complex cell RNA mixture (FIG. 3). This highly repeatable, quantitative, and precise assay has the potential to allow a detection level of latent HIV-1 infection at the same scale as or better than available assays, but with a much shorter activation period and with correspondingly fewer reagents and personnel time. The OTP assay further has the potential to detect latent HIV-1-infected cells in 20-50 mL of whole blood from HIV-1 infected individuals under anti-retroviral treatment, which would provide critical support to clinical trials evaluating new HIV-1 treatments. In some embodiments, the compositions or kits provide for direct detection of HIV-1 RNA at a limit of detection (LoD) of 5-100 pM (corresponding to 1-20 RNA copies in a cell with a representative cellular volume of 1 pL). Thus, the fluorogenic compositions or kits described herein offer a significant improvement in reliability, without sacrificing sensitivity, over other latent HIV-1 assays. In addition, the present disclosure provides compositions, kits, and methods capable of producing an independent standard for RT-PCR and similar RNA assays, as the present disclosure is based on direct RNA detection, independent of the conversion of RNA to DNA through an RT (reverse transcriptase) step.

In some embodiments, the target RNA sequence is HIV-1 Pol/Int. In some embodiments, the target RNA sequence is HIV-1 Pol/Int and the photocatalyst probe is a DNA probe with the sequence: 5'-GCACTGACTAATTTATCTACT-3' (SEQ ID NO: 1). In some embodiments, the target RNA sequence is HIV-1 Pol/Int and the profluorophore probe is a DNA probe with a sequence selected from: (a) 5'-TTCAT- TTCCT-3' (SEQ ID NO: 2); (b) 5'-TTCATTTCCTCCAAT-3' (SEQ ID NO: 3); and (c) 5'-TTCATTTCCTCCAATTCC-3' (SEQ ID NO: 4). In some embodiments, the photocatalyst probe is a DNA probe with the sequence of SEQ ID NO: 1 and the profluorophore probe is a DNA probe with the sequence of SEQ ID NO: 2.

In some embodiments, the target RNA sequence is HIV-1 Pol/Int and the photocatalyst probe is a PNA probe with the sequence: 5'-Acetyl-O-TTTATCTACT-Lys-3' (SEQ ID NO: 5). In some embodiments, the target RNA sequence is HIV-1 Pol/Int and the profluorophore probe is a PNA probe with a sequence selected from: (a) 5'-TTCATTTC-O-3' (SEQ ID NO: 6); (b) 5'-TTCATTT-0-3' (SEQ ID NO: 7); and (c) 5'-TTCATT-O-3' (SEQ ID NO: 8). In some embodiments, the target RNA sequence is HIV-1 Pol/Int, the photocatalyst probe is a PNA probe with the sequence of SEQ ID NO: 5, and the profluorophore probe is a PNA probe with the sequence of SEQ ID NO: 6.

In some embodiments, the target RNA sequence is HIV-1 TAR and the photocatalyst probe is a PNA probe with the sequence: 5'-Acetyl-O-GA*GCT*CCC*AG-Lys-3' (SEQ ID NO: 9) or a DNA probe with the sequence: 5'-TAGCCAGAGAGCTCCCAG-3' (SEQ ID NO: 10). In some embodiments, the target RNA sequence is HIV-1 TAR and the profluorophore probe is a PNA probe with the sequence: 5'-TCA*GAT*CT-O-3' (SEQ ID NO: 11) or a DNA probe with the sequence: 5'-TCAGATCT-3' (SEQ ID NO: 12) or 5'-TCAGATCTGGT-3' (SEQ ID NO: 13). In some embodiments, the photocatalyst probe is a PNA probe with the sequence of SEQ ID NO: 9 and the profluorophore probe is a PNA probe with the sequence of SEQ ID NO: 11 or is a DNA probe with the sequence of SEQ ID NO: 12. In some embodiments, the photocatalyst probe is a DNA probe with the sequence of SEQ ID NO: 10 and the profluorophore probe is a DNA probe with the sequence of SEQ ID NO: 12 or 13.

In some embodiments, the probe pair comprises SEQ ID NOs: 1-13 in the combinations disclosed above or any pair of oligonucleotide probes that vary by one, two, or more nucleotides per probe from any of the recited combinations. The B* bases shown in the structures above are modified PNA monomers of structure (A), (B), or (C). In some embodiments, the B* bases shown in the structures of photocatalyst probes are modified PNA monomers of structure (B). In some embodiments, the B* bases shown in the structures of profluorophore probes are modified PNA monomers of structure (C).

In some embodiments, the probe pairs comprise sequences as shown in one or more of the probe pairs listed below. As examples, Probe Pair 1 and Probe Pair 7 show the probe sequence in italics that targets the italicized portion of the corresponding target sequence, and the probe sequence in bold that targets the bolded portion of the corresponding target sequence. The "Azido-Coumarin" or "Pyridinium-Fluorescein" in a given probe is the profluorophore and is on the profluorophore probe, and the "Ru" in a given probe is the inactive photocatalyst and is on the photocatalyst probe. Nucleotides are abbreviated as "nt."

(1) Probe Pair 1 (DNA Probe Pair for HIV-1 Pol/Int):

a) Target Sequences within HIV-1 Pol/Int RNA (shown in italics or bold as an example):

(SEQ ID NO: 14)
5'-GAAUUGG*AGGAAAUGAA*CAAGUAGAUAAAUUAGUCAGUGCUGGAA-3'
(HIV-1 Pol/Int Target RNA Sequence within HIV-1 Pol/Int transcript)

b) Probes (shown in italics or bold as an example):

(SEQ ID NO: 15)
5'-GCACTGACTAATTTATCTACT-Ru-3' (21 nt)

(SEQ ID NO: 16)
5'-Azido-Coumarin-*TTCATTTCCT*-3' (10 nt)

(2) Probe Pair 2 (DNA Probe Pair for HIV-1 Pol/Int):

SEQ ID NO: 15
(21 nt)

(SEQ ID NO: 17)
5'-Azido-Coumarin-TTCATTTCCTCCAAT-3' (15 nt)

(3) Probe Pair 3 (DNA Probe Pair for HIV-1 Pol/Int):

SEQ ID NO: 15
(21 nt)

(SEQ ID NO: 18)
5'-Azido-Coumarin-TTCATTTCCTCCAATTCC-3' (18 nt)

(4) Probe Pair 4 (PNA Probe Pair for HIV-1 Pol/Int):

(SEQ ID NO: 19)
5'-Acetyl-O-TTTATCTACT-Lys-Ru-3' (10 nt)

(SEQ ID NO: 20)
5'-Azido-Coumarin-TTCATTTC-O-3' (8 nt)

(5) Probe Pair 5 (PNA Probe Pair for HIV-1 Pol/Int):

SEQ ID NO: 19
(10 nt)

(SEQ ID NO: 21)
5'-Azido-Coumarin-TTCATTT-O-3' (7 nt)

-continued (6) Probe Pair 6 (PNA Probe Pair for HIV-1 Pol/Int):

SEQ ID NO: 19

(10 nt)

(SEQ ID NO: 22)

5'-Azido-Coumarin-TTCATT-O-3' (6 nt)

(7) Probe Pair 7 (PNA Probe Pair for HIV-1 TAR):

a) Target Sequences within HIV-1 TAR RNA (shown in italics or bold as an example):

(SEQ ID NO: 23)

5'-UGGGUCUCUCUGGUUAGACC*AGAUCUGA*CGCUGGGAGCUCUCUGGCUA ACUAGGGAACCC A-3' (HIV-1 TAR RNA, complete transcript)

b) Probes (shown in italics or bold as an example), wherein the modified bases B* discussed in paragraph [0178] above are miniPEGs according to either structures (B) or (C) in paragraph [0140] above:

(SEQ ID NO: 24)

5'-Acetyl-O-**GA*GCT*CCC*AG**-Lys-Ru-3' (10 nt)

(SEQ ID NO: 25)

5'-Azido-Coumarin-*TCA*GAT*CT*-O-3' (8 nt)

(8) Probe Pair 8 (PNA-DNA Probe Pair for HIV-1 TAR):

SEQ ID NO: 24

(10 nt)

5'-Azido-Coumarin-TCAGATCT-3' (8 nt)(SEQ ID NO: 26), wherein optionally a 1X or greater PBS solution is used for Probe Pair 8

(9) Probe Pair 9 (DNA-DNA Probe Pair for HIV-1 TAR):

(SEQ ID NO: 27)

5'-TAGCCAGAGAGCTCCCAG-Ru-3' (18 nt)

SEQ ID NO: 26

(8 nt)

(10) Probe Pair 10 (DNA-DNA Probe Pair for HIV-1 TAR):

SEQ ID NO: 27

(18 nt)

(SEQ ID NO: 29)

5'-Azido-Coumarin-TCAGATCTGGT-3' (11 nt)

(11) Probe Pair 11 (DNA-DNA Probe Pair for HIV-1 TAR) (underlined base is single base mismatch with HIV-1 TAR RNA template SEQ ID NO: 23):

(SEQ ID NO: 28)

5'-TAGCCAGAGA<u>A</u>CTCCCAG-Ru-3' (18 nt)

SEQ ID NO: 29

(11 nt)

(12) Probe Pair 12 (PNA-PNA Probe Pair for HIV-1 TAR):

SEQ ID NO: 24

(SEQ ID NO: 33)

5'-Pyridinium-Fluorescein-TC*AGA*TCT*O-3'

(13) Probe Pair 13 (PNA-PNA Probe Pair for HIV-1 TAR):

SEQ ID NO: 24

(SEQ ID NO: 34)

5'-Pyridinium-Fluorescein-O-TC*AGA*TCT*O-3'

(14) Probe Pair 14 (PNA-DNA Probe Pair for HIV-1 TAR):

SEQ ID NO: 24

(SEQ ID NO: 35)

5'-Pyridinium-Fluorescein-TCAGATCT-3'

(15) Probe Pair 15 (DNA-DNA Probe Pair for HIV-1 TAR):

SEQ ID NO: 27

(18 nt)

(SEQ ID NO: 35)

5'-Pyridinium-Fluorescein-TCAGATCT-3'

-continued

(16) Probe Pair 16 (DNA-DNA Probe Pair for SARS-CoV-2 Spike RNA):

a) Target Sequences within SARS-CoV-2 Spike RNA (shown in italics or bold as an example):

(SEQ ID NO: 36)
5'-A*CCCAUUGG*UGCAGGUAUAUGCGCUAGUUAUCAG-3' SARS-CoV-2 Spike (S) Target RNA Sequence b) Probes (shown in italics or bold as an example):

(SEQ ID NO: 37)
5'-TGATAACTAGCGCATATACCTG-Ru-Ru-3'

(SEQ ID NO: 38)
5'-Azido-Coumarin-*CCAATGGG*-3'

(17) Probe Pair 17 (DNA-DNA Probe Pair for SARS-CoV-2 ORF8 RNA):

a) Target Sequences within SARS-CoV-2 ORF8 RNA (shown in italics or bold as an example):

(SEQ ID NO: 39)
5'-G*AGCUAGAAAAU*CAGCACCUUUAAUUGAAUUGUGC-3' SARS-CoV-2 ORF8 Target RNA Sequence b) Probes (shown in italics or bold as an example):

(SEQ ID NO: 40)
5'-CACAATTCAATTAAAGGTGCT-Ru-3'

(SEQ ID NO: 41)
5'-Azido-Coumarin-*TTTTCTAGCT*-3'

In the HIV-1 TAR PNA probe pairs shown in Probe Pairs 7 and 8, the B* units are PNA monomers of structure (B) for the photocatalyst probes and are PNA monomers of structure (C) for profluorophore probes.

5. Additional Embodiments

In some embodiments, a fluorogenic nucleic acid composition or kit for quantitative detection of a target RNA sequence in a test sample comprises:

(a) at least one pair of oligonucleotide or modified-backbone oligonucleotide probes comprising an upstream, first probe having a 5' end and a 3' end, and a downstream, second probe having a 5' end and a 3' end, forming a probe pair of two probes;

(b) wherein the first probe and the second probe are complementary to an upstream and a downstream portion, respectively, of the target RNA sequence, and further wherein the upstream and downstream portions of the target RNA sequence to which the probes bind have a gap of 0 to 8 nucleotides on a linear RNA or a gap consisting of the RNA sequence within a nonlinear structure that brings the probe binding sites into close proximity; and (c) wherein the first probe is covalently bound at its 3' end to a photocatalyst or a profluorophore, and the second probe is covalently bound at is 5' end to a profluorophore or a photocatalyst, wherein the photocatalyst is capable of being activated by exposure to visible light and a reducing agent to form an activated, reduced photocatalyst, which is capable of reducing the profluorophore to a fluorophore when and only when both probes of the probe pair hybridize to the target RNA sequence and the 3' end of the first probe and the 5' end of the second probe are separated by 0 to 8 nucleotides on a linear RNA or a gap consisting of the RNA sequence within a nonlinear structure which brings the probe binding sites on the target RNA sequence into close proximity, and wherein the fluorophore produces fluorescence emissions that are quantitatively detectable over a background signal.

B. Photocatalysts and Photocatalyst Probes

In some embodiments, the photocatalyst is bound to the downstream end of the upstream probe and the profluorophore is bound to the upstream end of the downstream probe. In some embodiments, the photocatalyst is bound to the upstream end of the downstream probe and the profluorophore is bound to the downstream end of the upstream probe.

In some embodiments, the photocatalyst is bound to the probe oligonucleotide through a non-oligonucleotide linker. The linkers can attach the photocatalyst to the oligonucleotide to prevent oligonucleotide interference with the light activation and/or reduction of the photocatalyst or to improve the reaction by adjusting the spatial position of photocatalyst relative to the profluorophore position. In some embodiments, one or more of the linkers are functionalized on either or both ends for attachment between the probe and photocatalyst or between the probe and a hydrophilic group. In some embodiments, the linker comprises an O-linker or lysine. In some embodiments, the linker comprises an O-linker (AEEA) (A), AEEEA (B), lysine (C), X-linker (D), E-linker (E), C6A (F), C3A (G), C4A (H), or C12A (I):

(A)

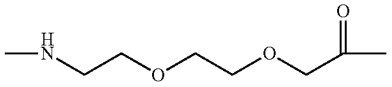

(B)

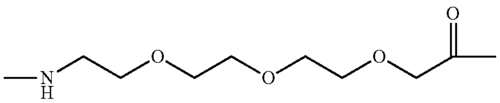

(C)

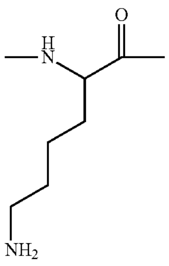

-continued (D)

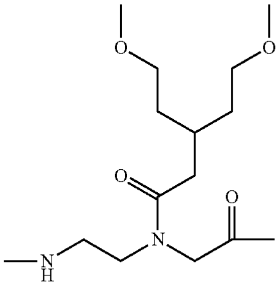

(E)

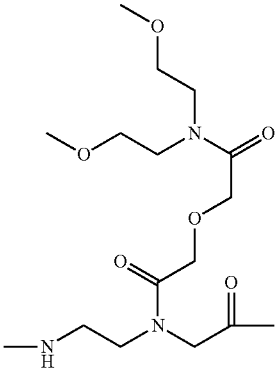

(F)

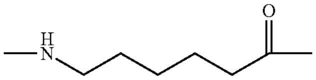

(G)

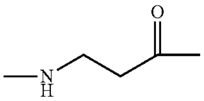

(H)

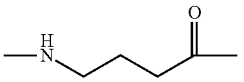

, or (I)

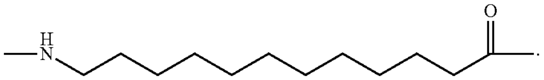

In some embodiments, the linker comprises an O-linker (A) or lysine (C).

In some embodiments, a hydrophilic group is attached to one or more of the linkers shown, to the free 5' or 3' oligonucleotide probe end, or to the gamma or alpha carbon on the pseudo-peptide backbone to improve hydrophilicity of the probe. Hydrophilic groups include diethylene glycol (miniPEG), polar or charged amino acids such as lysine, asparagine, glutamine, tyrosine, threonine, serine, aspartate, or glutamate. Hydrophilic groups also include azide, amine, alkyne, maleimide, thiol, or acetyl groups. In some embodiments, the hydrophilic group is miniPEG attached to one or more of the gamma carbons on the photocatalyst probe pseudo-peptide backbone.

In some embodiments, one or more of the nucleotide bases in the oligonucleotide sequence of the photocatalyst probe are modified to (1) 2,6-diaminopurine, which increases the binding affinity and corresponding Tm of the probe to target by increasing the number of hydrogen bonds formed with uracil or thymine from two (via adenine) to three (via 2,6-diaminopurine); (2) pseudoisocytosine or thiol-pseudoisocytosine, which improve RNA secondary structure infiltration and binding; or (3) inosine, which provides degeneracy to the PNA (or DNA) probe, allowing it to bind an A, C, or U base at a given nucleotide location within the target sequence.

In some embodiments, the photocatalyst comprises a photoactivatable complex of ruthenium (II), iridium (III), rhodium (III), osmium (II), palladium (II), or platinum (II). In some embodiments, the photocatalyst comprises a photoactivatable pyridyl complex of ruthenium (II) or iridium (III). In some embodiments, the photocatalyst comprises tris (2,2'-bipyridine) ruthenium (II) ($Ru(bpy)_3^{2+}$), bis(2,2'-bipyridine)-(phenanthroline) ruthenium (II) ($Ru(bpy)_2(phen)^{2+}$), or tris[2-phenylpyridinato-$C^2$, N]iridium (III) ($Ir(ppy)_3$). In some embodiments, the photocatalyst is:

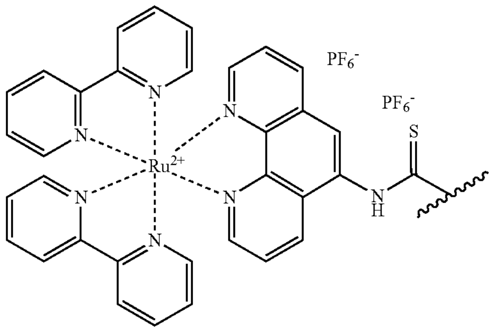

or

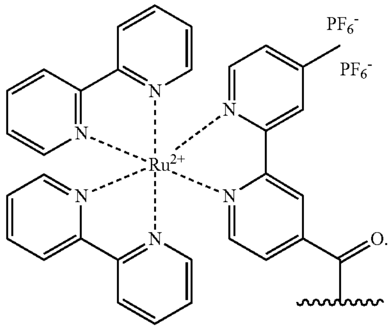

In some embodiments, the photocatalyst probe is prepared by reacting a photocatalyst reagent with an oligonucleotide probe sequence. In some embodiments, the attachment reaction forms an amide or a thiourea group. In some embodiments, an amino group on the oligonucleotide probe sequence, such as an Amino Modifier C6 linker group added to a DNA oligonucleotide during synthesis or the side chain amino group of a Lysine added at one end (usually 3') of a PNA oligonucleotide, is reacted with an isothiocyanate (PC-NCS) or N-hydroxysuccinimide ester (PC-NHS), where PC is the photocatalyst. Exemplary conjugation reactions are shown below for PNA probes (Reaction A or B) or DNA probes (Reaction B). In some embodiments, the photocatalyst is tris (bipyridine) ruthenium (II) ($Ru(bpy)_3^{2+}$), and is coupled to the oligonucleotide sequence by reaction of the oligonucleotide with bis(2,2'-bipyridine)-4'-methyl-4-carboxybipyridine-ruthenium N-succinimidyl ester bis (hexafluorophosphate), or $Ru(bpy)_2$ (mcbpy-O-Su-ester) $(PF_6)_2$, as shown in Reaction B.

(A)

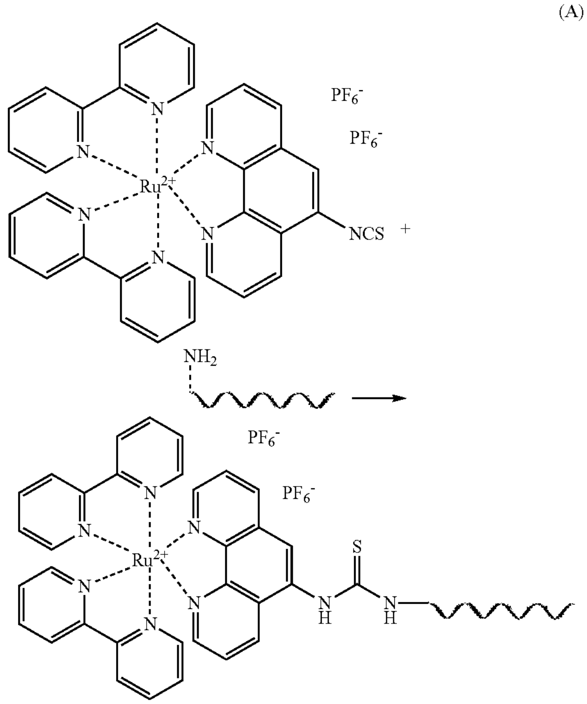

(B)

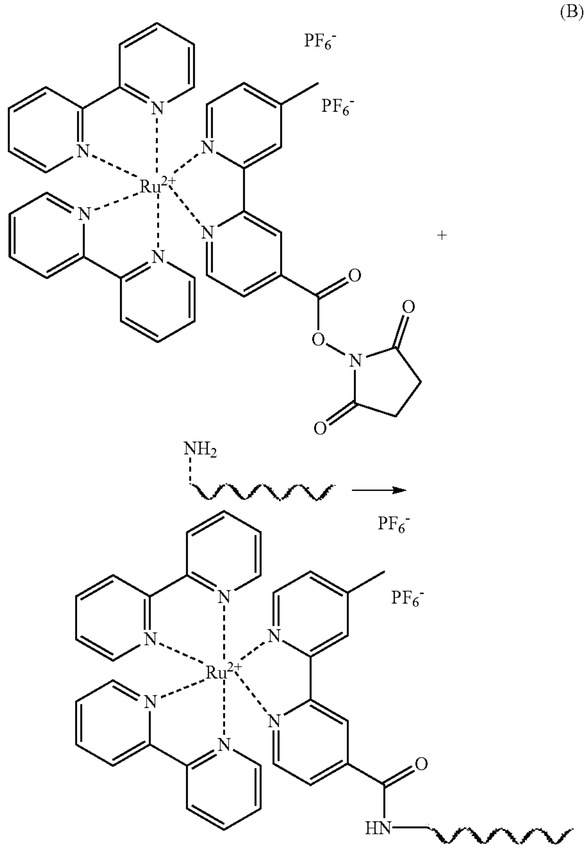

In some embodiments, the photocatalyst is activatable by exposure to visible light. In some embodiments, the light is a wavelength of from about 400 to about 500, about 420 to about 480, about 440 nm to about 460 nm, or 455 nm. In some embodiments, the maximum absorption of the photocatalyst is 455 nm, suggesting use of a wavelength of about 440 nm to about 460 nm. Depending on the photocatalyst, different wavelengths of light may be used. In some embodiments, using a bandpass filter to restrict the wavelength of light to 440 nm or higher prevents non-photocatalyst mediated reduction of the profluorophore (such as a coumarin-azide, which can have reduction with light at 350 nm). If other profluorophores (such as pyridinium-fluorescein) are used, light-induced reduction is not a factor.

C. Profluorophores and Fluorophores

The profluorophore probe comprises a covalently bound profluorophore. When the two probes in a pair are proximally bound to the target RNA sequence, the reduced, activated photocatalyst on the photocatalyst probe, in the presence of a reducing agent, is capable of reducing the profluorophore to produce a detectable fluorophore that emits a fluorescent signal under suitable conditions. In some embodiments, neither the profluorophore nor the fluorophore absorbs light at the wavelength used to activate the photocatalyst in the probe pair.

In some embodiments, the profluorophore is covalently bound to the oligonucleotide sequence of the profluorophore probe through a non-oligonucleotide linker (also known as a spacer). In some embodiments, the linker is an amino acid or an alpha-aminoxy amide. In some embodiments, the linker comprises an O, AEEEA, lysine, E, X, C3A, C4A, C6A, or C12A linker. The linkers can serve to attach the profluorophore to the oligonucleotide to prevent oligonucleotide quenching of the resulting fluorophore or to improve the reaction by adjusting the position of profluorophore relative to the photocatalyst. In some embodiments, the linker comprises an O-linker or lysine.

In some embodiments, the profluorophore is covalently bound to the oligonucleotide sequence of the profluorophore probe through a self-immolative linker, which is disrupted during reduction of the profluorphore by the activated photocatalyst to release the fluorophore from the oligonucleotide sequence of the probe. Release of the fluorophore prevents quenching by the oligonucleotide sequence of the probe. In some embodiments, the profluorophore self-immolative linker is attached through a pyridinium-substituted fluorescein or pyridinium-substituted rhodamine.

In some embodiments, one or more hydrophilic groups are attached to one or more linkers (O, AEEEA, lysine, E, X, C3A, C4A, C6A, or C12A), to the free 5' or 3' probe end, or to the gamma or alpha carbon on the pseudo-peptide backbone to improve hydrophilicity of the probe. Hydrophilic attachment groups include diethylene glycol (miniPEG), polar or charged amino acids including lysine, asparagine, aspartate, glutamine, glutamate, tyrosine, threonine, or serine. Hydrophilic attachment groups also include azide, amine, alkyne, maleimide, thiol, or acetyl groups. In some embodiments, the hydrophilic group is miniPEG attached to one or more gamma carbons on the profluorophore probe pseudo-peptide backbone.

In some embodiments, one or more of the nucleotide bases in the oligonucleotide sequence of the profluorophore probe are modified to 2,6-diaminopurine, a pseudoisocytosine or thiol-pseudoisocytosine, or inosine. These alternative, non-natural nucleotide bases (1) improve probe to template binding affinity and/or RNA secondary structure infiltration, by increasing the $T_m$ of the probe to the template above that of the same probe sequence length consisting of only natural nucleotide bases, for the case of 2,6-diaminopurine, pseudoisocytosine, or thiol-pseudoisocytosine base substitutions; or (2) allow the probe to bind at the same $T_m$ and sequence specificity despite one or more single nucleotide polymorphisms within the target RNA sequence, in the case of one or more inosine base substitutions.

A profluorophore may be conjugated to an oligonucleotide probe using methods known in the art. In some embodiments, an amino, oxyamino, or alkynyl group on the oligonucleotide sequence is reacted with a profluorophore reagent, comprising a reactive group such as a carboxylic acid, an activated carboxylic acid (such as a N-hydroxysuccinimide ester), an aldehyde, or an azide, to form a covalent linkage, such as an amide, an imine, or a triazole bond. In some embodiments, the profluorophore reagent comprises a carboxylic acid or a N-hydroxysuccinimide ester for coupling with an amino-modified oligonucleotide. Exemplary coupling reactions are shown below in Reactions C-F. In some embodiments, a PNA profluorophore probe is prepared as shown in Reactions C and D, and a DNA profluorophore probe is prepared as shown in Reaction D.

(C)

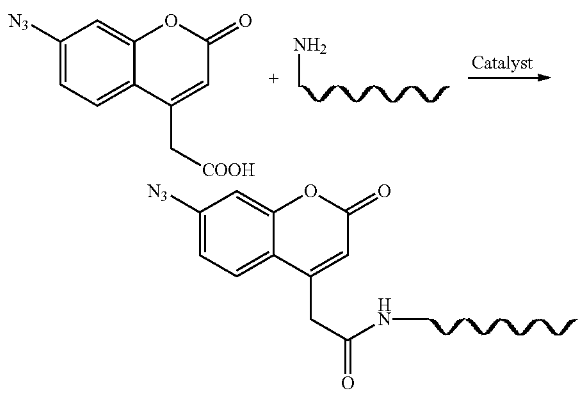

(D)

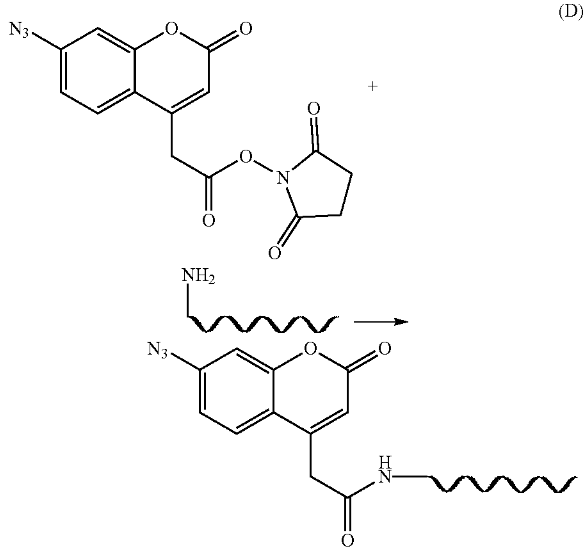

(E)

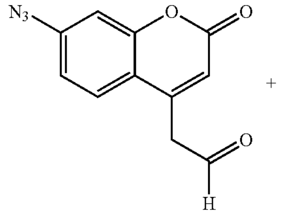

-continued

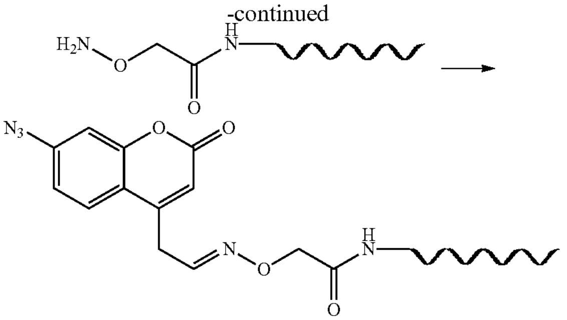

(F)

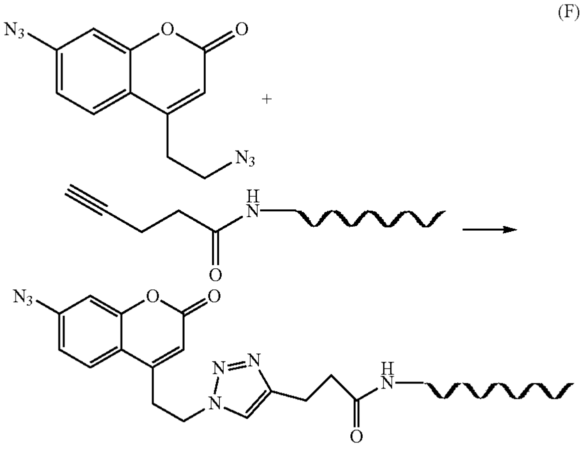

In some embodiments, the profluorophore is coupled to the probe oligonucleotide sequence using a reagent of the following structure:

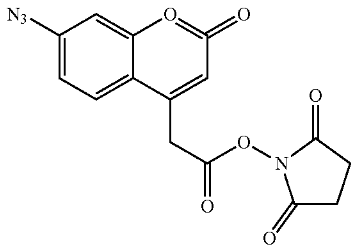

or

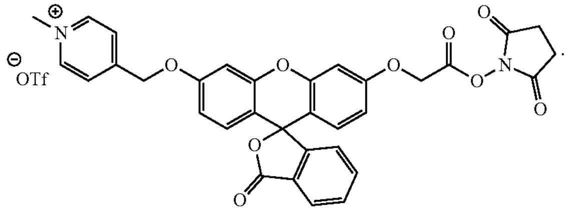

In some embodiments, the profluorophore comprises a reducible aryl azido moiety. In some embodiments, the profluorophore comprises a reducible pyridinium cation. In some embodiments, the profluorophore comprises a reducible self-immolative linker. In some embodiments, the profluorophore comprises (A) azido-coumarin, (B) azido-cresyl violet, (C) azido-rhodamine or (D) double-azido-rhodamine (such as rhodamine or rhodamine 110), (E) azido-fluorescein or (F) double azido-fluorescein, (G) pyridinium-substituted coumarin, or (H) pyridinium-substituted cresyl violet, (I) pyridinium-substituted rhodamine, (J) double-pyridinium-substituted rhodamine, (K) pyridinium-substituted fluorescein, (L) double-pyridinium-substituted fluorescein, (M) pyridinium-substituted rhodamine with a self-immolative linker, (N) (O) (P) pyridinium-substituted fluorescein with a self-immolative linker, or (Q) double-pyridinium-substituted fluorescein with an azide linker. In some embodiments, the profluorophore comprises an azido-coumarin or a pyridinium-substituted fluorescein group. In some embodiments, the profluorophore is:

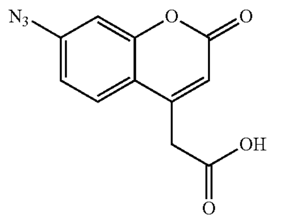

(A)

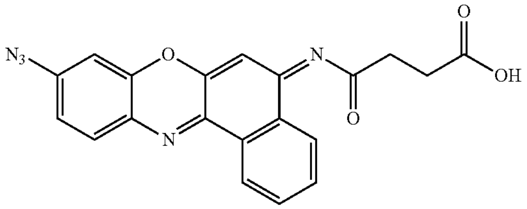

(B)

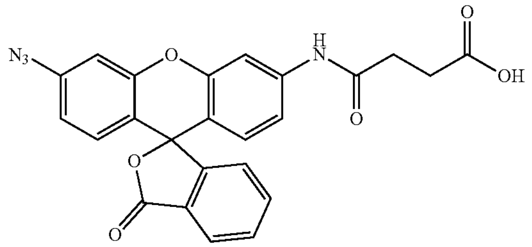

(C)

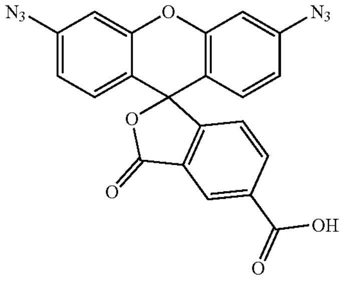

(D)

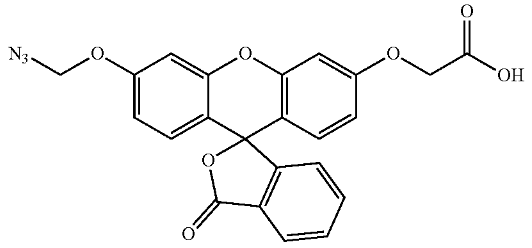

(E)

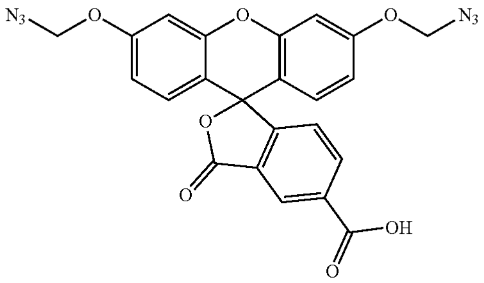

(F)

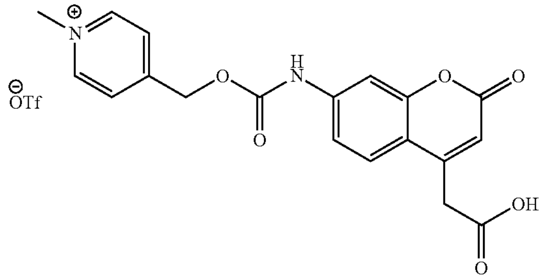

(G)

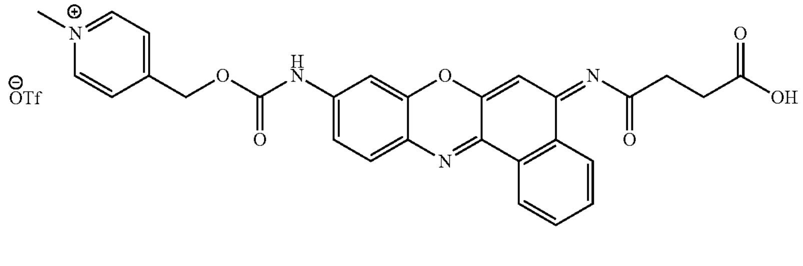

(H)

-continued
(I)
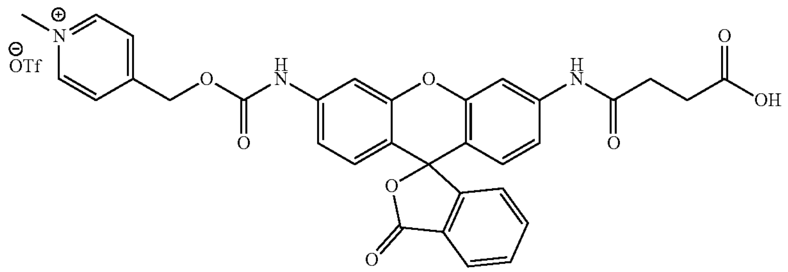
(J)
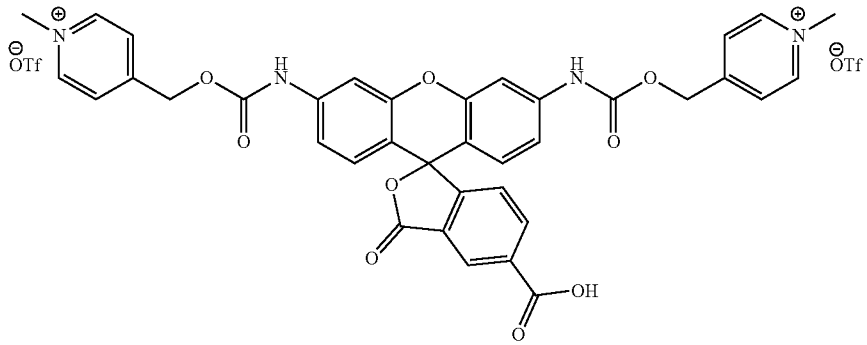
(K)
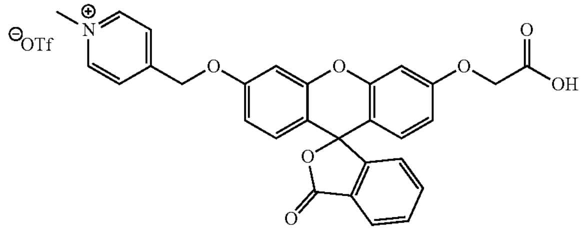
(L)
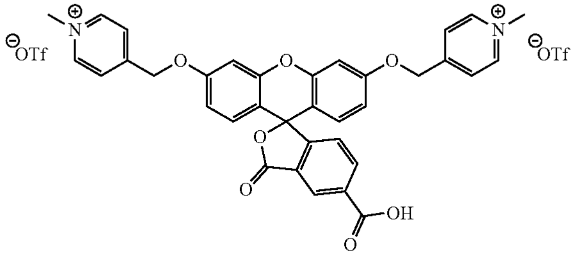
(M)
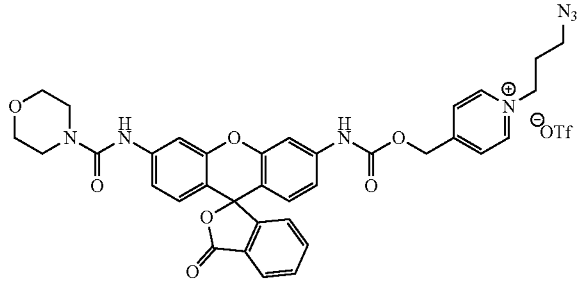
(N)
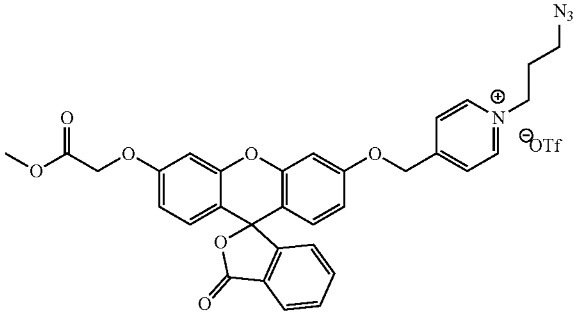
(O)
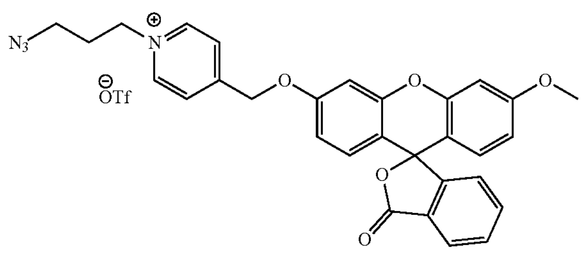
(P)
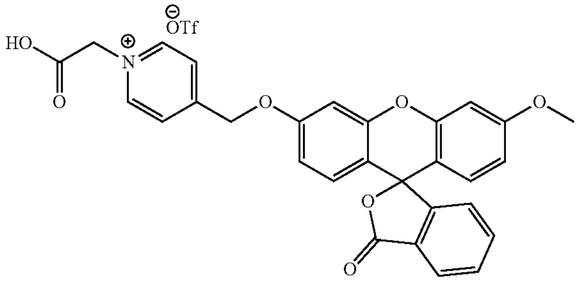

-continued (Q)

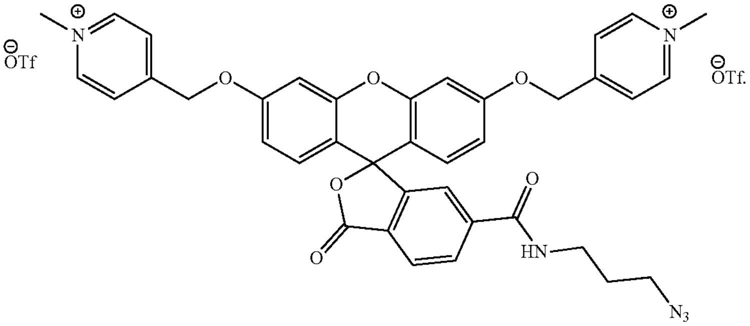

In some embodiments, the profluorophore is:

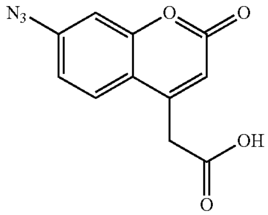

or

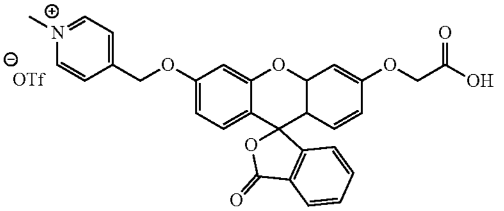

or

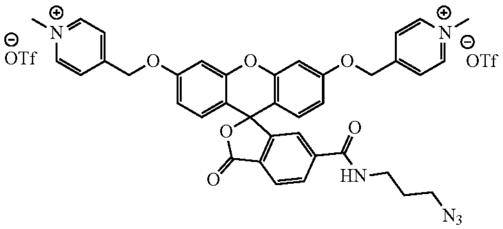

or

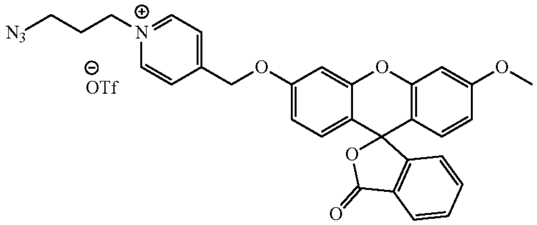

, and the photocatalyst is:

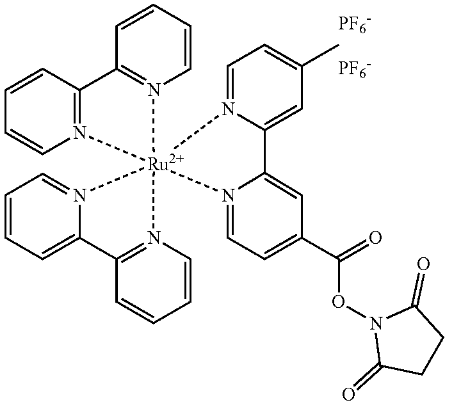

or

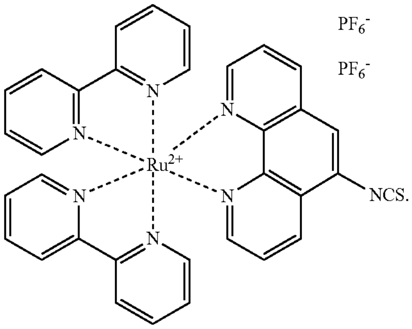

In the case of DNA oligos, the oligo may be modified at one end by an amine attachment, which may then be reacted with the N-hydroxysuccinimide (NHS) ester of a profluorophore or photocatalyst.

In the case of PNA oligos, the attachment for the profluorophore may be through the—$NH_2$ end, while the photocatalyst may be attached through the Lys residue, but could be attached by an O-or other linker.

The probe sequences may be 5'-3' opposite polarity for both DNA and PNA oligos to their complementary RNA target sequence. The attachment chemistry, whether profluorophore or photocatalyst may be at either side of the abutting probe ends to meet up in between the two probe sequences.

III. Fluorogenic Methods for Quantitative Detection of RNA

In another aspect, the disclosure relates to a fluorogenic method for quantitatively detecting a target ribonucleic acid (RNA) sequence in a sample with the fluorogenic nucleic acid composition or kit as described herein, comprising:

a) hybridizing the photocatalyst probe to the target RNA sequence to form a hybridized sample in the reaction buffer in the presence or absence of a reducing agent;
b) optionally hybridizing the photocatalyst probe to the target RNA sequence to form a hybridized sample in the presence of a DNA or PNA opener sequence, in the reaction buffer in the presence or absence of a reducing agent;
c) optionally hybridizing the photocatalyst probe to the target RNA sequence to form a hybridized sample in the presence of a DNA or PNA opener and exposing the mixture to denaturing conditions (optionally 95° C.) followed by a temperature 5° C. below the annealing temperature of the photocatalyst probe and/or opener to its target RNA sequence (optionally 40-70° C.), in the reaction buffer in the presence or absence of a reducing agent;
d) hybridizing the profluorophore probe to the target RNA sequence to form a hybridized profluorophore probe, in the reaction buffer in the presence or absence of a reducing agent;
e) exposing the hybridized sample containing photocatalyst probe, profluorophore probe, and any optional DNA or PNA opener, in reaction buffer to (i) light of a wavelength of about 440 nm to about 460 nm, with a preferred wavelength of 455, and (ii) a reducing agent (if not already in the reaction mixture), thereby activating the photocatalyst to form a reduced, activated photocatalyst, which then spontaneously reduces the profluorophore on the hybridized profluorophore probe to a fluorophore, thereby forming a hybridized fluorophore probe and regenerating the photocatalyst;
f) optionally, through the use of a self-immolative linker, the fluorophore produced in e) is released from the hybridized fluorophore probe;
g) denaturing the hybridized fluorophore probe from the target RNA sequence under conditions whereby the photocatalyst probe remains hybridized to the target RNA sequence;
h) optionally performing g) at temperature isothermal to the OTP reaction temperature;
i) optionally performing g) at a higher temperature than the OTP reaction temperature;
j) repeating d), e), g) for multiple turnover; and
k) detecting the amount of fluorescence emitted by the fluorophore using a standard fluorometer with light source and filters set to allow excitation at the wavelength of the resulting fluorophore and capture of the emission wavelength of the resulting fluorophore. Preferred is a fluorometer with a plate-reader or microfluidics for high-throughput and/or low volume reaction handling capacity.

In another aspect, the disclosure relates to a fluorogenic method for quantitatively detecting a target ribonucleic acid (RNA) sequence in a sample with the fluorogenic nucleic acid composition or kit as described herein, comprising:

a.2) hybridizing the photocatalyst probe to the target RNA sequence to form a hybridized sample in the reaction buffer in the presence or absence of a reducing agent;
b.2) optionally hybridizing the photocatalyst probe to the target RNA sequence to form a hybridized sample in the presence of a DNA or PNA opener in the reaction buffer in the presence or absence of a reducing agent;
c.2) optionally hybridizing the photocatalyst probe to the target RNA sequence to form a hybridized sample in the presence or absence of a DNA or PNA opener and exposing the mixture to denaturing conditions followed by a temperature 5° C. below the annealing temperature of the photocatalyst probe and/or opener to its target RNA sequence, in the reaction buffer in the presence or absence of a reducing agent;
d.2) hybridizing the profluorophore probe to the target RNA sequence to form a hybridized profluorophore probe, in the reaction buffer in the presence or absence of a reducing agent;
e.2) optionally performing steps a) and d) together, containing photocatalyst probe, profluorophore probe, and target RNA sequence, in the reaction buffer in the presence or absence of a reducing agent;
f.2) optionally performing steps b) and d) together, containing photocatalyst probe, profluorophore probe, DNA or PNA opener, and target RNA sequence, in the reaction buffer in the presence or absence of a reducing agent;
g.2) exposing the fully hybridized sample from d), e), or f) containing photocatalyst probe, profluorophore probe, and optional DNA or PNA opener, in reaction buffer to (i) light of a wavelength of about 440 nm to about 460 nm, preferably 455 nm, and (ii) a reducing agent, thereby activating the photocatalyst to form a reduced, activated photocatalyst, which then spontaneously reduces the profluorophore on the hybridized profluorophore probe to a fluorophore, thereby forming a hybridized fluorophore probe and regenerating the photocatalyst;
h.2) denaturing the hybridized fluorophore probe from the target RNA sequence under conditions whereby the photocatalyst probe remains hybridized to the target RNA sequence;
i.2) optionally repeating step d), g) and step h); and
j.2) detecting the amount of fluorescence emitted by the fluorophore using a fluorometer that provides the excitation wavelength for the fluorophore and can measure the emission wavelength of the fluorophore after excitation. Preferred is a spectrofluorometer, plate-reader, or microfluidic fluorometer for high throughput or small volume, integrated fluorimetry, and a stable background for the fluorometer at the emission wavelength used.

In some embodiments, the RNA detection probe pairs and methods described herein provide for direct detection of RNA at a limit of detection (LoD) of 5 pM (corresponding to 1 RNA copy in a cell with representative cellular volume of 1 pL), at a reaction turnover number of 2000 in 12-24 h, yielding 10 nM of activated fluorophore per 5 pM RNA, which is within the detection range of a common plate fluorometer. In some embodiments, using a shorter reaction time (20 min to 1 h) with a turnover number of 100, for applications that require less sensitive detection, the assay has an LoD of 100 pM RNA in a complex RNA preparation. The assay provides for high sensitivity with a higher signal-to-background (S/B) ratio for sensing target RNA than a Förster resonance energy transfer (FRET) assay and can achieve better reliability and quantification in the pM-nM RNA detection range compared to RT-PCR. Unlike RT-PCR, the OTP assay described herein can be efficiently scaled up for high throughput and easily accessible testing in research and clinical environments. The procedure involves simple mixing of sample dilutions and quantitative controls with probes in a suitable buffer containing a reducing agent, preferably in a 96-, 384-, or 1,536-well plate, heat treatment (if needed as an initial step), then isothermal reaction at 20° C. to 40° C. with light exposure for as little as 15 to 20 min, but typically for 1 h, followed by detection in a fluorometer, which requires less than 10 s per sample to obtain each assay result. In some embodiments, the photoreaction and fluorometer detection are combined for real-time detection. The reaction is not inhibited by enzyme inhibitors in RNA preparations, nor is the reaction exhausted or degraded, as an enzyme-based reaction would be, over time, allowing the use of less stringent RNA extraction protocols and flexibility in reaction time, with a reliable (stable) and quantitative result.

In some embodiments, the method does not involve conversion of RNA to DNA or other target sequence amplification, unlike RT-PCR, and thus does not introduce bias or lose representation of RNA present in the reaction, nor does it suffer from the addition of mutations which occurs during RT-PCR.

When and, in some embodiments only when, the photocatalyst probe hybridizes to the target sequence and is converted to the activated, reduced photocatalyst, and the profluorophore probe hybridizes to the target sequence, the activated, reduced photocatalyst reduces the profluorophore to form a fluorophore. The photocatalyst and profluorophore are designed to react with each other, across a distance of approximately 0 to 8 nucleotides on a linear RNA or a distance consisting of the RNA sequence within a nonlinear structure, to convert the profluorophore to a quantitatively-detectable fluorescent compound (a fluorophore). Background fluorescence may occur due to random interactions between the probes in solution or from non-catalyzed conversion of the profluorophore into fluorophore, and such background fluorescence from the interaction of the photocatalyst with the profluorophore or from non-catalyzed conversion of the profluorophore into fluorophore is within the scope of the disclosure. In some embodiments, the photocatalyst is provided at one half to a quarter or less of the quantity of profluorophore, for the purpose of reducing such background fluorescence due to random interactions between the probes in solution. In some embodiments, a set of reactions always includes a negative control which lacks the template RNA and contains both probes at the same concentrations of experimental reactions which contain or may contain the template RNA. Such a templated reaction, in some embodiments and not including background, when and only when it occurs, produces a stable, quantitatively detectable, real-time, fluorescent readout for highly-precise and accurate determinations, for example, of exact sequence and degenerate splice sites in single-stranded RNA or stem-loops or other topological configurations within secondary structure RNA.

A. Reaction Conditions

1. Probe Concentration and Reaction Buffers

In some embodiments, the probes within the pair of probes are each at a concentration of from 10 pM to 500 nM when mixed with the sample and under the reaction conditions. In some embodiments, the concentration of the profluorophore probe is from about 25 to about 500 nM, or about 50 to about 200 nM, or about 100 nM. In some embodiments, the concentration of the photocatalyst probe is from about 1 to about 200 nM, or 25 to about 50 nM. The preferred relative concentrations of profluorophore probe to photocatalyst probe are 4:1 (such as 100 nM: 25 nM) for some PNA-PNA and PNA-DNA probe pairs and 2:1 (such as 100 nM: 50 nM) for some DNA-DNA probe pairs, with the optimal ratio discovered through initial background testing for a given probe pair.

In some embodiments, the probes and reagents of the fluorogenic nucleic acid composition or kit are added to the sample in a buffered salt solution such as phosphate-buffered saline (PBS) at a concentration of about 0.05 to about 20×. A person of ordinary skill in the art can supply reaction buffers for the assay, which includes photoreactions, probe hybridization, and optional denaturing the target RNA and annealing the probes and/or openers. In some embodiments, the reaction buffer at final concentration comprises from 5×to 10×PBS. In some embodiments, the reaction buffer at final concentration comprises from 1 to 5×PBS. In some embodiments, the reaction buffer at final concentration comprises from 0.05 to 5×PBS.

2. Denaturing Conditions

In some embodiments, the sample comprising the target RNA sequence is exposed to denaturing conditions before hybridization of the probes. The denaturing conditions may be selected to denature all secondary structures in the target RNA or it may be selected to be partially denaturing to denature only certain secondary structures in the target RNA. In some circumstances, denaturing conditions comprise temperatures of from about 50 to about 100° C. and/or the use of chemical denaturants, such as urea, formamide, DMSO, or glyoxal. Denaturing conditions may include heating to a temperature ranging from about 50 to about 100° C., or from about 70° C. to 100° C., or from about 90° C. to 100° C., or from about 70° C. to about 95° C., or from about 50° C. to about 80° C., depending on buffer composition and the melting temperature/s of the RNA structures. For most or all RNA secondary structures in 1× PBS, for example, heating to about 95° C. is sufficient to create denaturing conditions. A person of ordinary skill in the art is familiar with denaturing (including fully denaturing and partially denaturing) conditions.

In some embodiments, the sample is exposed to denaturing conditions to remove the fluorophore probe from the target RNA sequence. In some embodiments, the denaturing conditions comprise temperature of from about 30° C. to about 80° C., or from about 50° C. to about 80° C., and/or chemical denaturants such as urea, formamide, DMSO, or glyoxal. In some embodiments, the denaturing comprises heating at a temperature from about 30° C. to about 80° C., or from about 50° C. to about 80° C. In some embodiments, the denaturing is performed under isothermal conditions. In some embodiments, the isothermal conditions comprise a temperature from about 20° C. to about 70° C., or from about 20° C. to about 60° C., or from about 20° C. to about 40° C., depending on any detergent, chemical denaturant, or salt present, and the probe composition (sequence, GC/AT content, length, and any modifications such as PNA modifications). In some embodiments, the isothermal conditions comprise a temperature from about 20° C. to about 40° C.

In some embodiments, steps d) and g) of the method (hybridizing the profluorophore probe and denaturing the fluorophore probe) are performed under thermocycling conditions. In some embodiments, step g) is performed at a temperature from about 30° C. to about 80° C., or in from about 50° C. to about 80° C., and step d) is performed at a temperature from about 40° C. to about 70° C. or from about 20° C. to about 70° C. In some embodiments, the isothermal conditions comprise a temperature from about 20° C. to about 40° C.

In some embodiments the step of denaturing the hybridized fluorophore probe from the target RNA sequence under conditions whereby the photocatalyst precursor probe remains hybridized to the target RNA sequence is performed at a temperature from about 30° C. to about 50° C., or from about 30° C. to about 70° C., or from about 40° C. to about 80° C., or from about 85° C. to about 95° C., or from about 70° C. to about 95° C. And the steps of hybridizing the profluorophore probe to the target RNA sequence to form a hybridized profluorophore probe, optionally including hybridizing the photocatalyst probe to the target RNA sequence to form a hybridized sample is performed at a temperature from about 20° C. to about 40° C., or from about 20° C. to about 50° C., or from about 20° C. to about 60° C., or from about 20° C. to about 70° C., or from about 30° C. to about 70° C., or from about 20° C. to about 50° C.

3. Hybridization Conditions

In some embodiments, the hybridizing of each probe, or both probes simultaneously, occurs at a temperature of from 20° C. to 70° C., or from about 20° C. to 40° C., or from about 20° C. to about 50° C., or from about 20° C. to about 60° C., or from about 30° C. to about 70° C., or from about 20° C. to about 50° C. With respect to both the isothermal and thermocycling embodiments, hybridization temperature and annealing temperature are essentially equivalent. In some embodiments, the hybridizing of one or both probes of a pair occurs under isothermal conditions. In some embodiments, the reaction time at an isothermal annealing temperature is from about 10 sec to 24 h, or from about 1 h to about 24 h or from about 15 min to about 1 h.

In some embodiments, hybridizing of photocatalyst probe and/or the profluorophore probe is performed in the presence of a DNA or PNA opener, optionally at a temperature of about 40° C. to about 80° C., or about 50° C. to about 70° C., or about 55° C. to about 65° C., or about 65° C.

In some embodiments, hybridizing of one or both probes occurs under thermocycling conditions. In some embodiments, for thermocycling reaction conditions, the sample would be repeatedly denatured by heating to about 95° C., then cooling to the annealing temperature of about 40° C. to 70° C., followed by the OTP reaction step at about 20° C. to 40° C. However, the annealing temperature can be combined with the OTP reaction step at a single temperature, for an exemplary thermocycling two-step procedure. In this case, the reaction temperature can match the annealing temperature.

If signal amplification is desired, either isothermal or thermocycling conditions may be used along with an excess of probe concentrations. In this manner, the probes bind to the target RNA, the profluorophore is converted to the fluorophore, the fluorophore probe falls off the target RNA, and a new profluorophore probe binds to the target RNA, and so forth. The photocatalyst probe is designed to remain hybridized while cycling between inactive and active photocatalyst forms. This method allows for the generation of multiple molecules of fluorophore per hybridized photocatalyst and constitutes the turnover number for the reaction, which increases over time.

4. Assay Additives

In some embodiments, the reducing agent is present at a concentration of 1 μM to 10 mM, or at a concentration of 50 μM to 10 mM, which is in large excess (50-200 times or greater than) of the expected concentration of the target RNA sequence in the sample and of the concentrations of photocatalyst and profluorophore probe used in the reaction. In some embodiments, the reducing agent is sodium ascorbate, N-diisopropylethylamine, formic acid, or NADPH. In some embodiments, the reducing agent is sodium ascorbate.

In some embodiments, the hybridizing of the photocatalyst probe and/or the profluorophore probe is performed in the presence of a PNA opener or a DNA opener.

In some embodiments, the hybridizing of the photocatalyst probe and/or the profluorophore probe is performed in the presence of at least one additive selected from DMSO, formamide, betaine, spermidine, and a detergent. In some embodiments, the additive is a detergent. In some embodiments, the additive is polysorbate 20 (also known as polyoxyethylene-20-sorbitan monolaurate) at a concentration of 0.05%.

B. Employing Controls

The fluorogenic method may include positive and/or negative controls. In some embodiments, the method comprises normalizing the amount of fluorescence that is detected in a negative control sample that contains a non-target RNA sequence to the highest possible amount of fluorescence measured from the profluorophore probe. In some embodiments, the method comprises normalizing the amount of fluorescence that is detected in a positive control sample that contains a target RNA sequence of known concentration to the highest possible amount of fluorescence measured from the profluorophore. In some embodiments, the negative and/or positive control RNA of known concentration is used as an internal control by addition to the test sample. In some embodiments, the positive control RNA sequence would differ from the target RNA sequence and additional probes would be used that would detect the positive control RNA.

Using one or more than one control can help to verify the accuracy of the quantification. In some embodiments, the method comprises calculating the amount of each target RNA sequence in the test sample from the normalized amount of fluorescence detected. In some embodiments, the method comprises calculating the number of cells with the potential to produce the target RNA by also measuring the amount of DNA encoding the target RNA sequence and/or by measuring the amount of a housekeeping DNA or RNA of known and consistent cellular content.

C. Sample Description

In some embodiments, the sample is a biological sample. In some embodiments, the biological sample is from a mammal, such as human, dog, cat, cow, pig, sheep, or horse. In some embodiments, the mammal is a patient, such as a human patient. In some embodiments, the patient is a human patient diagnosed with HIV-1. In some embodiments, the sample is an environmental sample, e.g., a waste sample, a water sample, a soil sample, or an air sample. In some embodiments, the sample is from any eukaryote, including a non-mammal animal, plant, fungus, or protozoan, or from a prokaryote, including a bacterium or archaebacterium. In some embodiments, the sample is from a mixed organism population, such as from a biofilm or microbiome.

In some embodiments, the sample comprises mixed RNA species from cells. In some embodiments, the sample is chosen from peripheral blood, lymph node, oral mucosa, gingival crevicular fluid (GCF), gut-associated lymphatic tissue (GALT), central nervous system (CNS) tissue, including brain tissue, cerebrospinal fluid (CSF), a mixed oral sample comprising oral mucosa, GCF, and saliva, or urine.

In some embodiments, total, active, or resting CD4+ T cells may be isolated from the peripheral blood mononuclear cell (PBMC) fraction of patient blood samples. These cells may be cultured and activated or untouched prior to OTP testing. Latent and resting T cell lines may be activated using PMA and ionomycin or PHA or any other activator of T cells or latent HIV genomes for OTP testing with probe pairs over a time course of 0 to 14 days. Total cellular mRNA may be extracted or released from cell samples consisting of about $1\times10^6$ to about $5\times10^6$ or more cells and tested for purity and concentration by UV spectroscopy. RNA may be extracted or released directly from oral mucosa and GCF samples, as a much lower number of cells, with higher activation level, compared to blood may be present.

D. Additional Embodiments

In some embodiments, the method comprises:

(1) lysing cells with lysis buffer containing detergent and/or protein denaturant;
(2) column purifying RNA with column that retains small RNAs (≥17nt) or no column purification;
(3) treating the RNA with DNase I during column purification;
(3) checking RNA quantity and purity by spectrophotometry;
(4) mixing the RNA sample with photocatalyst probe, profluorophore probe, and reducing reagent in buffer solution (for detection of HIV-1 TAR, PNA/DNA opener may also be added and an initial heating treatment performed in this step);
(5) exposing the mixed solution to an LED light;
(6) measuring solution fluorescence as a function of time.

In some embodiments, the method comprises one or more of:

(1) lysing the cells using TRIzol/TRI reagent, RIPA buffer, phenol-chloroform, osmotic shock, sonication, microwave, chemical, detergent, freeze-thaw or mechanical disruption treatment, or a combination of these methods, prior to the addition of probes;
(2) treating the lysed cells with DNase I and protease prior to the addition of the probes, to remove genomic DNA and proteins that may be bound to the RNA targets;
(3) passing the lysed cells through an initial filter to remove genomic DNA;
(4) purifying RNA from the lysed cells via column method, alcohol and salt precipitation, or other purification method prior to the addition of probes;
(5) calibrating the RNA level detected to the number of starting cells via cell count or PCR or ddPCR or qPCR or RT-qPCR of DNA or RNA endogenous or exogenous or encapsulated, spiked in or not spiked in, multiplexed or side-by-side; and
(6) adding one or more DNA or PNA openers, complementary to one or more regions that immediately flank a target RNA sequence, to the reaction to optimize probe binding or the reaction by mitigating the effect of RNA secondary or higher order (tertiary or quaternary) structures on target accessibility to the fluorogenic probes or the proximity or orientation of one reactive probe end to the other reactive probe end.

E. Use of OTP Assays to Provide a Reference Standard

The present methods, kits, and compositions, in some nonlimiting embodiments, may be used to provide a reference standard.

The fluorogenic nucleic acid compositions, kits, and methods may be employed to provide a quantitative reference standard for calibrating levels of particular target RNA sequences, which represents an acute need, especially, for example, in monitoring cell-based HIV-1 RNA levels in HAART patients, for which no such quantitative RNA standard exists in the prior art. This may be accomplished using the methods described herein, for example, to calibrate RT-qPCR, RT-ddPCR, RT-LAMP, or another RNA detection assay, as the present methods detect RNA directly, without the need for a DNA intermediary, or for nucleic acid amplification.

F. Use of OTP Assays in Quantitative Detection of HIV-1 Levels

In some embodiments, the methods described herein are used to detect and quantify HIV-1 levels in a sample. In some embodiments, the methods are used to determine HIV-1 positive cell number in a sample by use of limiting dilution and/or by normalization to signal from an internal control probe for CD4 RNA (expressed in CD4+ T cells) and RPS17 or UBE2D2 RNA (uniformly expressed in human peripheral blood mononuclear cells, PBMC). In some embodiments, the methods described herein are used to quantitatively detect HIV-1 levels in latent and/or activated reservoirs.

In some embodiments, HIV-1 TAR is detected by adding a PNA or DNA photocatalyst probe and a PNA or DNA opener to the sample, with an initial heating step of about 1 min to about 2 min to a temperature of about 60° C. to 100° C., or about 90° C. to 100° C., or about 95° C., then cooling to the annealing temperature of about 40 to 70° C., or about 65° C., for about 1 min to about 5 min, followed by cooling the reaction mixture to about 15° C. to 40° C., or about 20° C. to about 25° C., and then adding a profluorophore probe, prior to the OTP reaction.

In some embodiments, quantitative detection of HIV-1 RNAs is achieved through a stable background level of 1-3% through optimization of buffer concentration, probe backbone, profluorophore and photocatalyst type, an optional initial heating step, and/or use of an optional DNA or PNA opener. This level of background can be achieved with DNA-DNA or PNA-DNA probe pairs, which showed similar efficiency and were both more efficient than PNA-PNA probe pairs targeting the same RNA sequences. In some and only some embodiments, better detection is achieved for RNA targets using DNA-DNA and PNA-DNA than PNA-PNA probe sets. Important considerations driving the choice of probe type include target RNA structure, length of sequence conservation, profluorophore probe backbone and length suited for isothermal reaction cycling, and the need to prevent inter- and intra-probe complementarity, a particular concern for RNA targets containing stem-loop or other secondary structures. DNA-DNA probes were found to tolerate more than three (3)-base complementarity between probes, but PNA-PNA probes did not tolerate more than a 3-base complementarity between probes. DNA probes have a greater length requirement, due to a lower $T_m$ for the same sequence length of a PNA probe, which can reduce the usefulness of DNA-DNA probes or DNA-PNA probe sets in RNA secondary structures. DNA probes are much less expensive and need no modifications for hydrophilicity, so are preferable where sufficient target RNA sequence conservation and less RNA secondary structure are present. Since DNA oligos are naturally very water soluble, the background reaction was found to be significantly lower when one or more DNA oligonucleotide was used.

In some embodiments, at least one PNA probe in a probe set may be used for RNA targets containing extensive secondary structure such as stem-loops that are more resistant to heat-denaturation (greater than 70° C.), as PNA probes can infiltrate nucleic acid secondary structures more efficiently than DNA probes. In some embodiments, OTP detection of RNA stem regions may additionally use an initial denaturing heating step and/or a DNA or PNA opener to improve accessibility to the OTP probes in order to provide the same level of RNA target detection sensitivity as for a linear RNA target. In some embodiments, PNA openers are preferable to DNA openers, due to better sequence infiltration by PNA openers and a higher $T_m$ per base pair with the target RNA.

In some embodiments, detection of RNA using OTP probes yielded findings in contrast to the buffer conditions reported in the literature for PNA-PNA probe pairs targeting DNA sequences in vitro. The use of DNA-DNA or PNA-DNA probe sets for the detection of DNA or RNA targets has not been reported. Literature use of buffer conditions of 0.5M Tris with 0.05% polysorbate 20, with or without 0.1% formamide, yielded a 3-10% fluorescence background (Röthlingshöfer M, Gorska K, Winssinger N. Nucleic acid templated uncaging of fluorophores using Ru-catalyzed photoreduction with visible light. Org Lett. 2012. 14:482-5; Sadhu KK, Winssinger N. Detection of miRNA in live cells by using templated RuII-catalyzed unmasking of a fluorophore. Chem. Eur. J. 2013. 19:8182-9). Literature use of buffer conditions of 1× PBS with 0.05% polysorbate 20 yielded a 1-5% fluorescence background (Chang D, Kim KT, Lindberg E, Winssinger N. Accelerating Turnover Frequency in Nucleic Acid Templated Reactions. Bioconjug Chem. 2018. 29:158-163). In contrast, buffer concentration for RNA detection using PNA-PNA, PNA-DNA, and DNA-DNA probe pairs was found to require significant optimization to yield a stable 1-3% fluorescence background. For example, a 0.05×PBS buffer was optimal for a PNA-PNA probe pair targeting HIV-1 Pol/Int, which is within a relatively linear structure, while a 0.1×PBS buffer was better for a PNA-PNA probe pair targeting HIV-1 TAR, within a very stable stem-loop structure. While 1×PBS was optimal for a DNA-DNA probe pair targeting HIV-1 Pol/Int, 5×PBS was much better for DNA-DNA or PNA-DNA probe pairs targeting HIV-1 TAR. Example results demonstrating the different detection levels as a function of PBS buffer concentration are shown in FIGS. 9A-9B and 10A-10B. In some cases, detection of RNA targets by the OTP reaction using PNA-PNA probes was found to require one-to two-fold lower buffer concentration compared to DNA-DNA or PNA-DNA probes. Further, optimal buffer concentration was found to be highly dependent upon RNA secondary structure and/or sequence. The use of PNA-DNA and DNA-DNA probe pairs, an optional initial heating step, and a DNA or PNA opener provides the greater flexibility required for successfully targeting different types of RNA secondary structures, which often present sequence complementarity constraints.

Quantitative detection of target RNA sequences may be performed on a broad range of test samples, including peripheral blood, lymph node, oral mucosa, gingival crevicular fluid (GCF), and saliva, as well as a mixed oral sample comprising oral mucosa, GCF, and saliva. Suitable test samples further include CD4+ enriched peripheral blood mononuclear cells (PBMC), lymph nodes containing B cell follicles, gut-associated lymphatic tissue (GALT), central nervous system (CNS) tissue, including brain tissue, cerebrospinal fluid (CSF), seminal fluid, ocular fluid, sebaceous fluid, and urine. OTP may be performed on the three types of samples, individually or in combination, as well as in comparative testing with RT-PCR or quantitative viral outgrowth assay (QVOA) or other measure of the HIV-1 latent reservoir, using the same samples.

1. Multiplex Detection of Cell-based HIV-1 RNA by OTP Assay

In some embodiments, the methods disclosed herein are used in multiplex detection of cell-based HIV-1 RNA from the samples described above (for example, CD4+-enriched PBMC from peripheral blood or mixed gingival crevicular fluid (GCF) and oral mucosa) to provide multiplexed or side-by-side quantitation of multiple, distinct HIV-1 RNA transcripts and cellular or positive control RNAs and/or DNAs. Such multiplex or multiple reaction simultaneous testing may be used to better estimate the number of latent HIV-1 infected cells in a sample to provide a measure of the latent reservoir or the level of activation of the latent reservoir. For multiplex detection, each probe pair is complementary to a different RNA target sequence, the photocatalyst moiety is the same for each probe pair, such that the OTP reaction occurs at the same photoactivation wavelength of light and reducing agent, and the profluorophore and resulting fluorophore is different for each probe pair, such that the different fluorophores are excited at different wavelengths. After completion of the OTP reaction, the sample is queried at the different excitation and emission wavelengths for the two or more different fluorophores resulting from the two or more different probe pairs utilized in the OTP reaction.

The OTP assay may be used to detect a latent HIV reservoir through collection of PBMCs with or without enrichment for CD4+ PBMC, or extraction of RNA. The results are then correlated to a particular level of latent HIV reservoir through a statistical calculation.

2. HIV-1 Spliced Site Targets for OTP Probes

For quantitative detection of HIV-1 in RNA from patient blood, oral mucosa, or GCF, a probe length of between 5 and 40 bases complementary to HIV-1 RNA may be used. In some embodiments, a probe between 8 and 30 bases may be used. HIV-1 target sequence regions suitable for HIV-1 OTP probes are described herein, and include HIV-1 Pol/Int, TAR, Gag, Env, Nef, Rev, Tat, Vif, Vpr, Vpu, 5'LTR, or 3'LTR, and in particular HIV-1 Pol/Int or HIV-1 TAR, as well as rearrangements of these sequences and any resulting junctions that occur through mutation, splicing, or selection from natural or artificial events, and any intervening or flanking sequences of HIV-1 Pol/Int, TAR, Gag, Env, Nef, Rev, Tat, Vif, Vpr, Vpu, 5'LTR, or 3'LTR.

HIV-1 RNA is spliced into different sizes as part of the protein expression process of HIV-1 virus production in an infected cell. The unspliced HIV-1 RNA transcript is about 9 kb (kilobases), with spliced forms including about 4 kb, 2 kb, and 1 kb transcripts. Cells actively infected by HIV generally produce at least the about 2 and 4 kb spliced transcripts in addition to unspliced (full-length) HIV-1 RNA transcripts during HIV-1 activation and virus production. Cells with a latent infection may not produce all spliced and full-length transcripts, but may produce at least the about 2 kb spliced transcripts.

HIV-1 RNA spliced or intact splice sites for OTP detection include:

(A) About 2 kb HIV-1 RNA transcripts spliced at donor site 1 (D1) to acceptor site 1 (A1), and possibly also at sites D2 to A2, and possibly also at sites D3 to A3, A4 (a, b, or c) or A5, but always spliced at sites D4 to A7.

(B) About 4 kb HIV-1 RNA transcripts spliced DI to A1, and possibly also D2 to A2, and possibly also D3 to A3, A4 (a, b, or c) or A5, but never spliced at D4 or A7 sites.

(C) About 9 kb full-length HIV-1 RNA transcripts contain all intact D and A splice sites and all introns.

Optimization of the length and composition of probes complementary to HIV-1 spliced (with splice sites and exons joined and intron sequences removed) and unspliced sequences (with splice sites and introns intact and exons not joined) to maximize the efficiency of OTP detection may be achieved by comparison of test results from probes targeting the sequence differences described above for the about 2, 4, and 9 kb HIV-1 RNA transcripts.

About 2 kb HIV-1 spliced RNAs, via the D4-A7 spliced site, encode HIV-1 Tat (transactivator) and Rev (regulator of expression of virion proteins) proteins. Tat protein binds to HIV-1 TAR RNA to allow high processivity of host RNA polymerase to produce longer HIV-1 transcripts. Rev protein facilitates transport of partially and unspliced HIV-1 RNA transcripts from the nucleus into the cytoplasm for translation. About 2 kb HIV-1 RNA transcripts are produced at a low level in latent HIV-1 infected cells, and the Tat-Rev D4-A7 spliced site (spanning nucleotides 6045-8379) is conserved across HIV-1 subtypes. Detection of spliced Tat-Rev HIV-1 RNA may facilitate accurate quantification of the latent pool, due both to its low copy number and because it may be indicative of transcriptional competence in latent HIV-1 infected cells.

About 4 kb HIV-1 spliced RNA transcripts are not spliced at the D4 and A7 sites, which allows expression of the viral envelope protein. Thus, the about 4 kb HIV-1 RNAs contain the intron between D4 and A7 sites and intact D4 and A7 splice sequences. However, the about 4 kb HIV-1 RNAs are all spliced between DI and A1 sites and thus lack the intron encoding HIV-1 Gag and Pol/Int.

About 9 kb full-length, fully unspliced HIV-1 RNA transcripts are expressed at later stages of virus replication from activated latent cells. The DI and A1 unspliced sites and the intron between the D1 and A1 unspliced sites are only found in the about 9 kb full-length HIV-1 RNA transcript, expected to be present at high levels only during later activation time points as well as in viral particles released into the plasma, GCF, or extracellular within the oral mucosa. Subtraction of the amount of DI unspliced site or Gag/Pol region (found only in the about 9 kb HIV-1 RNA transcripts) from the amount of D4 or A7 unspliced sites or Env region (found in both the about 9 and 4 kb HIV-1 RNA transcripts) measured in cellular RNA yields the amount of 4 kb HIV-1 RNA in cells.

OTP can be used to differentially quantify the three HIV-1 RNA transcript sizes expressed in a cell: (1) Measuring the level of the D4-A7 spliced site measures the level of the about 2 kb HIV-1 RNAs. Measuring the level of either the D4 or the A7 unspliced site, or the intron region (Env) between the D4 and A7 splice sites, will quantify the about 4 kb HIV-1 RNA (expressing the Env protein) plus the about 9 kb HIV-1 RNA (full-length HIV-1 genome, expressing Gag, Pol, and Env proteins). Measuring the level of the DI unspliced site or intron (Gag/Pol) will quantify only the about 9 kb full-length HIV-1 genome. Subtracting (3) from (2) will yield the level of only the about 4 kb RNAs.

OTP assay controls comprised of in vitro-transcribed HIV-1 RNAs cloned into an expression vector lacking the HIV-1 TAR region to allow for efficient in vitro transcription may include: (A) HIV-1 sequence containing spliced DI-A1, and possibly also D2-A2, D3-A3, A4a,b,c or —A5, and/or D4-A7 (introns removed in each case); (B) HIV-1 sequence containing either or both the D1 and D4 unspliced sites or portions of the intronic regions between DI and A1 (Gag/Pol) or D4 and A7 (Env). OTP control target sequences within these regions can be mutated so as to provide a unique signal for these controls when hybridizing control OTP probes are used. These three RNA transcripts permit in vitro testing and optimization of the ability to accurately quantify and differentiate between the levels of transcripts containing each of the spliced or unspliced sites, joined or separated exons, and presence or absence of introns. These sequences can also serve as negative controls for OTP probes that bind to sequences not present (i.e., removed between spliced sites) in the transcript. Other in vitro-transcribed RNA negative controls can contain non-HIV-1 RNA sequences.

Quantitative measurements for the HIV-1 latent reservoir can be made using the fluorogenic compositions, kits, and methods described herein. Test kits for quantitative detection of cell-associated HIV-1 RNA in a test sample may be fashioned to include, for example, (a) one or more probe pairs to detect about 2 kb spliced HIV-1 RNA; (b) one or more probe pairs to detect the about 4 kb spliced and about 9 kb full-length HIV-1 RNAs; (c) one or more probe pairs to detect the about 9 kb full-length HIV-1 RNA; (d) one or more each of positive and negative probe pairs; and (e) a concentrated reaction buffer comprising, after final dilution, a concentration of NaCl from 5 mM to 3 M and 0.1 mM to 60 mM KCl, in a NazHPO4/KH2PO4 buffer at a pH between 6 and 8, preferably at 7.4.

Probe pairs to spliced or unspliced CD4 or other cellular RNA or DNA may be included in the test kit or included as a separate, control kit. Probe pairs may contain (1) one or more probe pairs to detect spliced or unspliced CD4 RNA or other cellular RNA or DNA for determining infected cell number and (2) one or more positive control reference target RNA sequences comprising each of the HIV-1 target RNA sequences in (a) through (c) of the test kit. In some embodiments, such an integrated or separate control kit also includes (3) a control reference material comprising one or more control probe pairs and corresponding RNA sequence/s. Any separate control kit, like the test kit, also contains a concentrated reaction buffer as described for the test kit. The control reference material may additionally be used as a spike-in internal control. The separate control kit may also contain positive controls comprised of one or more probe pairs to detect one or more cellular RNAs and the corresponding synthetic or in vitro-transcribed cellular RNA sequences.

G. Methods of Treatment

The methods described herein may be combined with treating a condition or disease identified through the testing method. For instance, this may include a method of treating HIV-1, another pathogen infection (as described herein), cancer, etc., depending on the RNA target of the testing. Thus, methods of treatment further include administering a known medication to a patient identified as having the target RNA or methods may include assessing the effectiveness of candidate treatments.

A method of treatment may include (a) using a method as described herein to test a sample from a patient and (b) administering an anti-HIV medication to a patient. A method of treatment may include performing the test method on samples obtained from the patient (i) before, (ii) after, or (iii) before and after the medication was administered. In some embodiments, the method further comprises administering an anti-HIV medication to a patient and performing the test method on samples obtained from the patient before and after the medication was administered. In some instances, the anti-HIV medication is undergoing clinical trials. In some circumstances, the method is conducted to determine if the patient's HIV-1 strain(s) are susceptible to the anti-HIV-1 medication. It is also important clinically to identify patients with a latent HIV-1 reservoir. Thus, a method can include obtaining a sample from the patient and administering an anti-HIV medication to the patient if the patient is found to have a latent HIV reservoir.

In some embodiments, a first sample is obtained from a patient before administration of an anti-HIV-1 medication. In some embodiments, a second sample is obtained from the patient after administration of the anti-HIV-1 medication. In some embodiments, the detected fluorescence for the first sample is compared to the detected fluorescence for the second sample. In some embodiments, the sample is obtained from a patient and the detected fluorescence indicates the patient has a latent HIV-1 reservoir. In some embodiments, the method comprises administering an anti-HIV medication to the patient with the detected latent HIV-1 reservoir.

IV. Test Kits

Test kits may be employed for quantitative detection of a target RNA sequence in a test sample comprising the probes of any of the fluorogenic nucleic acid compositions or kits described herein and at least one buffer.

In some embodiments, the at least one buffer is a reaction buffer. A person of ordinary skill in the art can design appropriate reaction buffers. In some embodiments, the reaction buffer comprises sodium chloride (NaCl) and potassium chloride (KCl). The reaction buffer at final concentration once mixed with the sample, probes, reducing agent, and any additives, may comprise from 5 mM to 3 M and 0.1 mM to 60 mM KCl, in a $Na_2HPO_4/KH_2PO_4$ buffer at a pH between 6 and 8, preferably at 7.4. In some situations, the reaction buffer at final concentration comprises 137 mM NaCl and 2.7 mM KCl, is buffered using 10 mM $Na_2HPO_4$ and 1.8 mM $KH_2PO_4$, and has a pH of 7.4.

In some circumstances, the test kit comprises at least one pair of oligonucleotide probes to quantitatively detect spliced or unspliced CD4 RNA.

In some embodiments, the test kit comprises a positive control and/or a negative control. The negative control may comprise a non-target RNA sequence.

In some embodiments, a test kit for quantitative detection of cell-associated HIV-1 RNA in a test sample comprises a fluorogenic nucleic acid composition or kit described herein and at least one buffer. In some embodiments, the at least one buffer is a reaction buffer. In some embodiments, the reaction buffer comprises sodium chloride (NaCl) and potassium chloride (KCl) and is buffered by $Na_2HPO_4$ and $KH_2PO_4$. In some embodiments, the reaction buffer at final concentration comprises from 5 mM to 3 M and 0.1 mM to 60 mM KCl. In some embodiments, the reaction buffer at final concentration comprises 137 mM NaCl and 2.7 mM KCl, in a $Na_2HPO_4/KH_2PO_4$ buffer at pH 7.4. In some embodiments, the test kit comprises at least one pair of fluorogenic probes to quantitatively detect spliced CD4+ RNA. In some embodiments, the test kit comprises a positive control. In some embodiments, the test kit comprises a negative control. In some embodiments, the negative control comprises a non-target RNA sequence.

EXAMPLES

Example 1: In Vitro Detection of HIV-1 Target RNA Sequences

Example 1A: Quantitative detection by OTP of HIV-1 Pol/Int RNA. This assay utilized photocatalyst probe SEQ ID NO. 15 at 50 nM; profluorophore probe SEQ ID NO. 16 at 100 nM; and HIV-1 Pol/Int RNA template SEQ ID NO. 14, at 0, 100 pM, 1 nM, and 10 nM. The reducing agent was ascorbate at 5 mM; the buffer was 1×PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using the maximum change in relative fluorescence unit (ΔRFUmax) of 245. The ΔRFUmax value is the measured full conversion of the same amount of the profluorophore probe reduced to fluorophore with a strong reducing agent (TCEP). The results (FIG. 1A) show an OTP detection threshold of 100 pM for the HIV-1 Pol/Int target sequence in vitro.

Example 1B: Quantitative detection of HIV-1 TAR RNA without heat and without PNA opener. This assay utilized photocatalyst probe SEQ ID NO. 27 at 50 nM; profluorophore probe SEQ ID NO. 26 at 100 nM; and HIV-1 TAR RNA template SEQ ID NO. 23 at 0, 100 pM, 1 nM, and 10 nM. The reducing agent was ascorbate at 5 mM; the buffer was 5×PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 290. The ΔRFUmax value is the measured full conversion of the same amount of the profluorophore probe reduced to fluorophore with a strong reducing agent (TCEP). There was a significant change in the buffer concentration (5×PBS) required for maximum HIV-1 TAR RNA detection, compared to that required for HIV-1 Pol RNA detection (1×PBS) (Example 1A). The results (FIG. 1B) show an OTP detection threshold of 100 pM for the stable stem-loop HIV-1 TAR RNA target sequence in vitro.

Example 2: Effect of Added PNA Opener and Heat on Detection of HIV-1 TAR

Figure 1B:
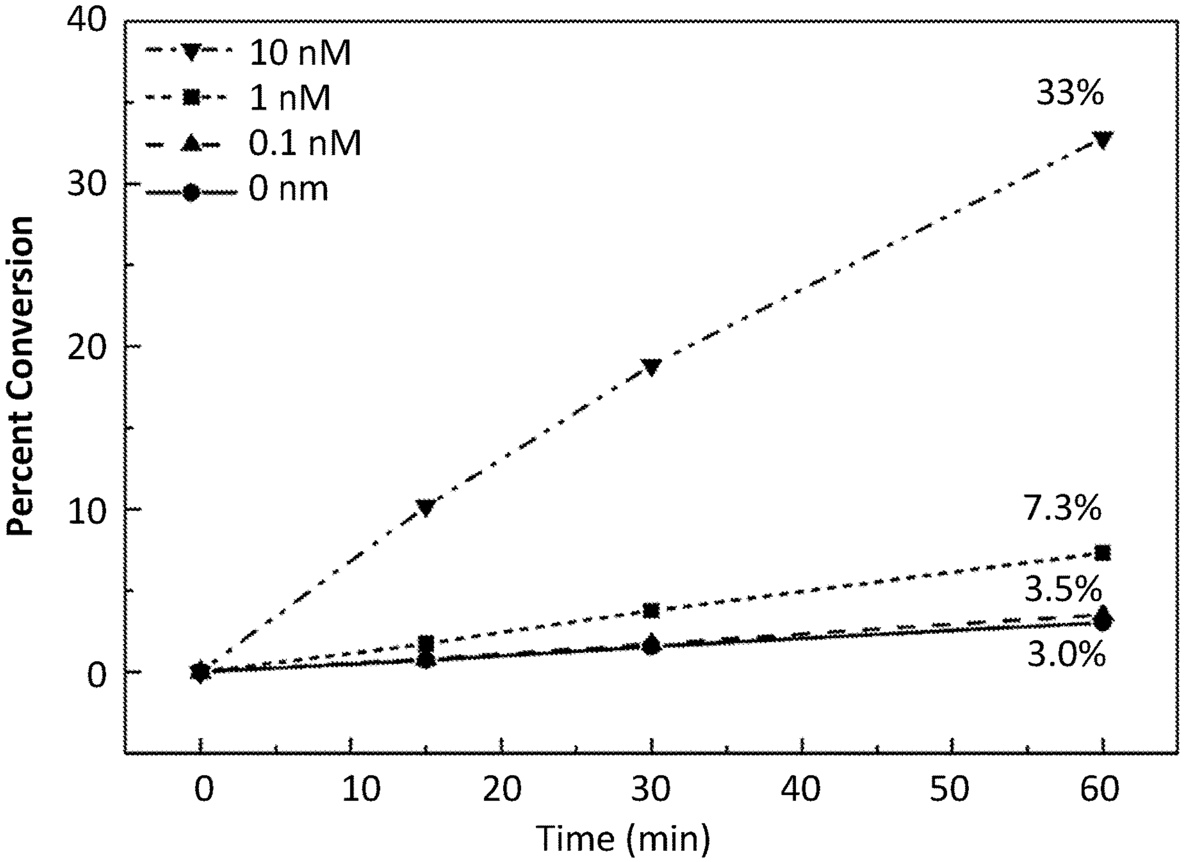
Figure 2:
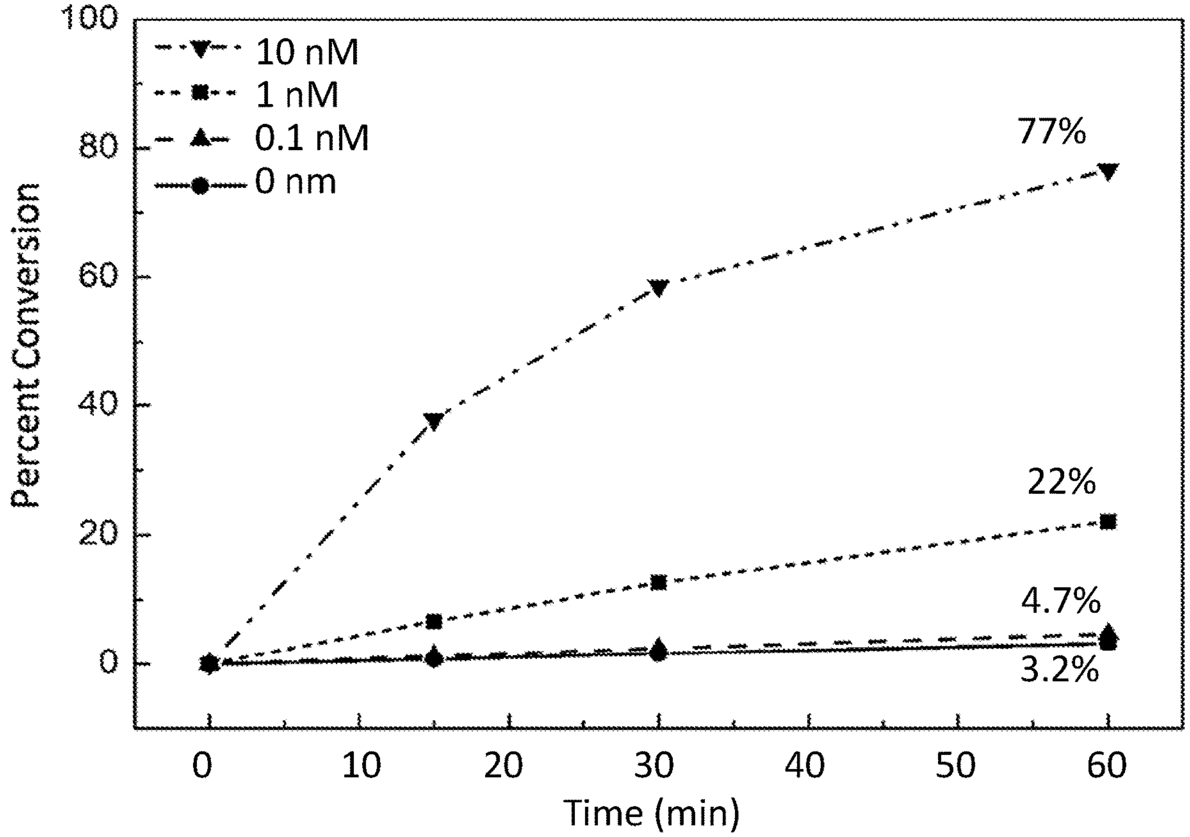
FIG. 2 shows quantitative detection by OTP reaction of HIV-1 TAR RNA.

Example 2: Quantitative detection of HIV-1 TAR RNA with heat and PNA opener. This assay utilized photocatalyst probe SEQ ID NO. 27 at 50 nM; profluorophore probe SEQ ID NO. 26 at 100 nM; HIV-1 TAR PNA opener SEQ ID NO. 31 at 100 nM; and HIV-1 TAR RNA template SEQ ID NO. 23 at 0, 100 pM, 1 nM, and 10 nM. The reducing agent was ascorbate at 5 mM; the buffer was 5×PBS, pH 7.4, with 0.05% polysorbate 20. An initial heating step was performed (95° C. for 2 min, 65° C. for 5 min) with the following reaction components: photocatalyst probe, PNA opener, template, and buffer. The reaction was placed at 4° C. and the profluorophore probe and reducing agent were added. The photoreduction reaction was then performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 290. The ΔRFUmax value is the measured full conversion of the same amount of the profluorophore probe reduced to fluorophore with a strong reducing agent (TCEP). The results (FIG. 2) demonstrate improved detection level for the HIV-1 TAR RNA template (compared to FIG. 1B) with the use of pre-reaction heat and a PNA opener that binds to the HIV-1 TAR RNA template.

Example 3: Detection of synthetic HIV-1 Target RNA Sequences in HIV-Negative Human Cell Total RNA Example 3A: Quantitative detection of HIV-1 Pol/Int spiked into HIV-negative human cell total RNA. This assay utilized photocatalyst probe SEQ ID NO. 15 at 50 nM; profluorophore probe SEQ ID NO. 16 at 100 nM; HIV-1 Pol/Int RNA template SEQ ID NO. 14, at 0, 100 pM, and 1 nM; and HeLa cell RNA extracted from $3\times10^6$ cells and diluted 1/10 (88 ng/μL). The reducing agent was ascorbate at 5 mM; the buffer was 1×PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 245. The ΔRFUmax value is the measured full conversion of the same amount of the profluorophore probe reduced to fluorophore with a strong reducing agent (TCEP). The results (FIG. 3A) show that the assay provides the same level detection of the HIV-1 Pol/Int target sequence when present in a great excess of non-HIV-1 RNA compared to HIV-1 Pol/Int alone (FIG. 1A). Thus, the OTP reaction was not inhibited by the large excess of non-HIV RNA, nor was non-specific detection observed.

Example 3B: Quantitative detection of HIV-1 TAR DNA spiked into HIV-negative human cell total RNA. This assay utilized photocatalyst probe SEQ ID NO. 24 at 25 nM; profluorophore probe SEQ ID NO. 25 at 100 nM; HIV-1 shortened TAR DNA template SEQ ID NO. 32 at 0, 100 pM, and 1 nM; and HaCaT cell RNA extracted from $3\times10^6$ cells and diluted 1/10(45 ng/μL). The reducing agent was ascorbate at 5 mM; the buffer was 1×PBS, pH 7.4, with 0.05% polysorbate 20.

The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 250. The ΔRFUmax value is the measured full conversion of the same amount of the profluorophore probe reduced to fluorophore with a strong reducing agent (TCEP). The results (FIG. 3B) show that the assay provides the same level detection of the HIV-1 TAR target sequence when present in a great excess of non-HIV-1 RNA compared to HIV-1 TAR alone (data not shown). Thus, the OTP reaction was not inhibited by the large excess of non-HIV RNA. However, non-specific detection was observed for non-spiked HIV-negative cell total RNA (6.5% is higher than the background of 3.4%).

Figure 4A:
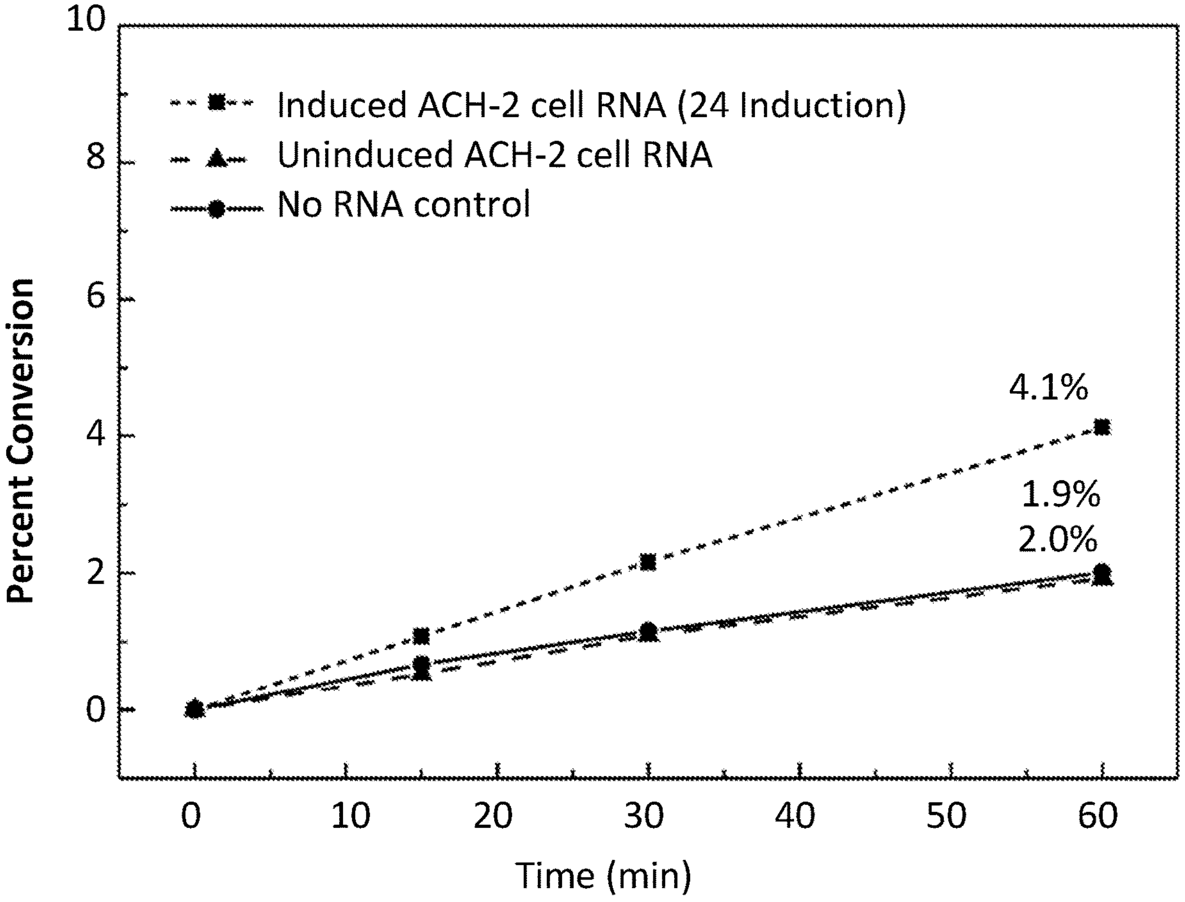
FIGS. 4A-4B show quantitative detection of native HIV-1 RNAs in HIV-1 infected cell total RNA.

Example 4: Detection of Native Target RNA Sequences in HIV-1 Positive Human Cell Total RNA Example 4A: Quantitative detection of native HIV-1 Pol/Int RNA in HIV-positive human cell total RNA. This assay utilized photocatalyst probe SEQ ID NO. 15 at 50 nM; profluorophore probe SEQ ID NO. 16 at 100 nM; uninduced ACH-2 cell RNA extracted from $3\times10^6$ cells and diluted 1/10(120 ng/μL); and ACH-2 cell RNA extracted from $3\times10^6$ cells induced for 24 h with PMA and ionomycin and diluted 1/10 (72 ng/μL). The reducing agent was ascorbate at 5 mM; the buffer was 1×PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 245. The ΔRFUmax value is the measured full conversion of the same amount of the profluorophore probe reduced to fluorophore with a strong reducing agent (TCEP). The results (FIG. 4A) show that the OTP provides HIV-1 Pol/Int detection in induced ACH-2 cell total RNA but not in uninduced ACH-2 cell total RNA. HIV-1 Pol/Int RNA is expected to be present in induced but not in uninduced ACH-2 cells.

Figure 4B:
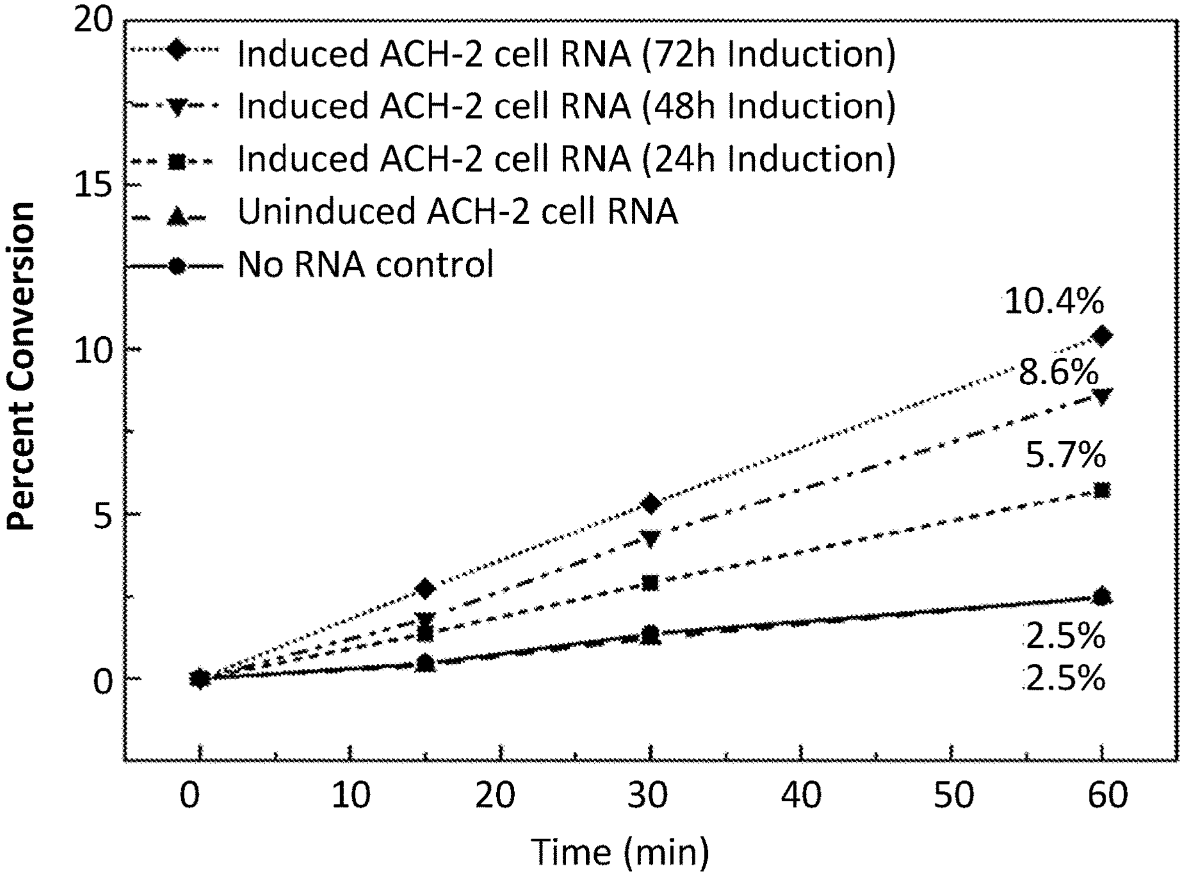

Example 4B: Quantitative detection of native HIV-1 TAR RNA in HIV-positive human cell total RNA. This assay utilized photocatalyst probe SEQ ID NO. 27 at 50 nM; profluorophore probe SEQ ID NO. 26 at 100 nM; and uninduced ACH-2 cell RNA extracted from $3\times10^6$ cells and diluted 1/10 (92 ng/μL), ACH-2 cell RNA extracted from $3\times10^6$ cells induced for 24 h and diluted 1/10(118 ng/μL), ACH-2 cell RNA extracted from $3\times10^6$ cells induced for 48 h and diluted 1/10(100 ng/μL), ACH-2 cell RNA extracted from $3\times10^6$ cells induced for 72 h and diluted 1/10(67 ng/μL). The reducing agent was ascorbate at 5 mM; the buffer was 5×PBS, pH 7.4, with 0.05% polysorbate 20. An initial heating step was performed (95° C. for 2 min, 65° C. for 5 min) with the following reaction components: photocatalyst probe, opener, template, and buffer. The reaction was placed at 4° C. and the profluorophore probe and reducing agent were added. The photoreduction reaction was then performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 290. The ΔRFUmax value is the measured full conversion of the same amount of the profluorophore probe reduced to fluorophore with a strong reducing agent (TCEP). The results (FIG. 4B) show that the OTP provides HIV-1 TAR RNA detection in induced ACH-2 cell total RNA but not in uninduced ACH-2 cell total RNA. Further, the level of HIV-1 TAR detection increases with the induction time, from 24 to 48 to 72 hr, despite a lower yield of total RNA from the same number of cells.

Figure 5A:
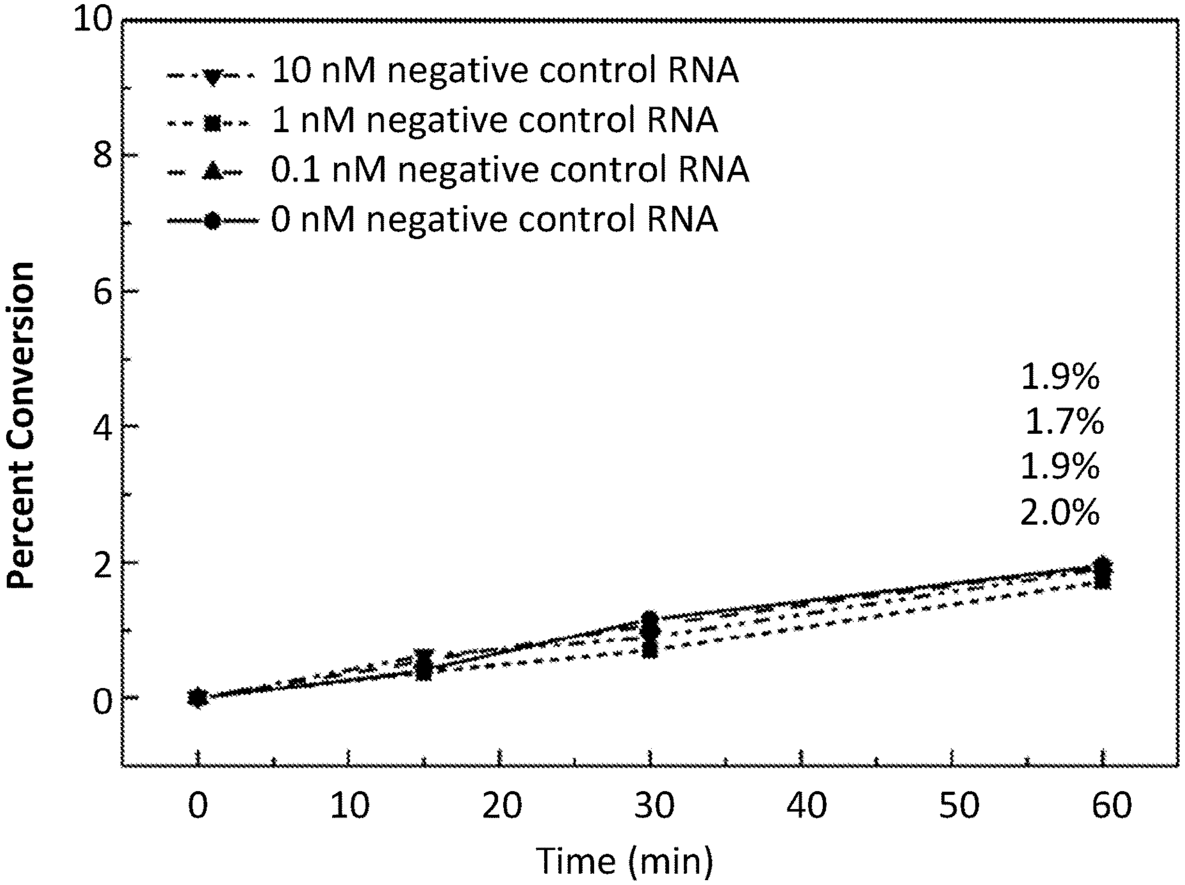
FIGS. 5A-5B show the specificity of the OTP reaction due to no detection of negative controls.

Example 5: OTP Probe Pairs are Specific and do Not Detect Non-Target RNA Sequences Example 5A: No detection seen for negative control RNA with HIV-1 Pol/Int probe pair. This assay utilized photocatalyst probe SEQ ID NO. 15 at 50 nM; profluorophore probe SEQ ID NO. 16 at 100 nM; and in vitro-transcribed HIV-1 Gag RNA, at 0, 100 pM, 1 nM, and 10 nM. The reducing agent was ascorbate at 5 mM; the buffer was 1×PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 245. The ΔRFUmax value is the measured full conversion of the same amount of the profluorophore probe reduced to fluorophore with a strong reducing agent (TCEP). The results (FIG. 5A) show that the HIV-1 Pol/Int OTP with a DNA-DNA probe set is specific in that it does not yield a false positive, or any detection above background, when tested with negative control HIV-1 RNA.

Figure 5B:
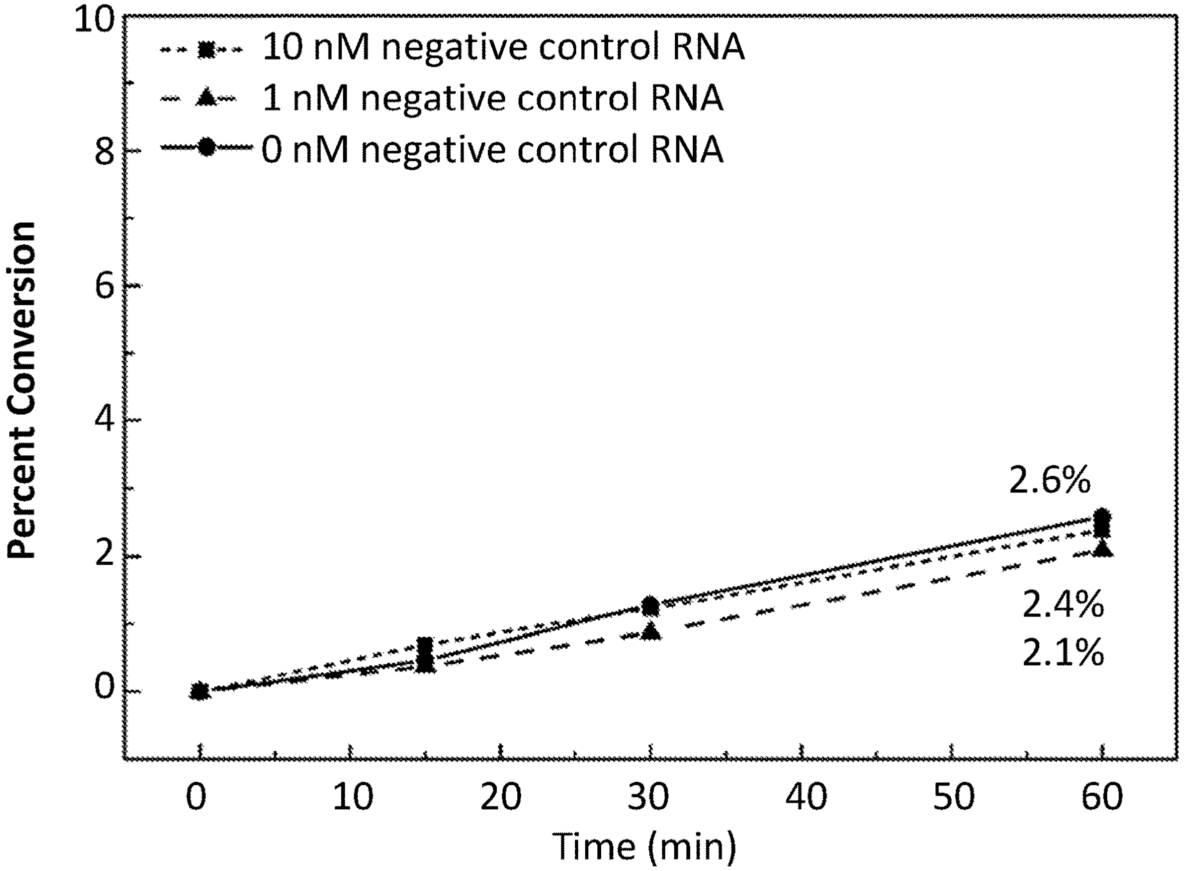

Example 5B: No detection seen for negative control RNA with HIV TAR probe pair. This assay utilized photocatalyst probe SEQ ID NO. 24 at 25 nM; profluorophore probe SEQ ID NO. 26 at 100 nM; and in vitro-transcribed HIV-1 Gag RNA negative control template at 0, 1 nM, and 10 nM. The reducing agent was ascorbate at 5 mM; the buffer was 5×PBS, pH 7.4, with 0.05% polysorbate 20. An initial heating step was performed (95° C. for 2 min, 65° C. for 5 min) with the following reaction components: precursor photocatalyst probe, opener, template, buffer, and reducing agent. The reaction was placed at 4° C. and the profluorophore probe was added. The photoreduction reaction was then performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 290. The ΔRFUmax value is the measured full conversion of the same amount of the profluorophore probe reduced to fluorophore with a strong reducing agent (TCEP). The results showed no detection above background, demonstrating that the templated reaction is highly specific for the target RNA sequences. The results (FIG. 5B) show that the HIV-1 TAR OTP with a DNA-PNA probe set is specific in that it does not yield a false positive, or any detection above background, when tested with negative control HIV-1 RNA.

Example 6: Probe Gap Distance on Template Affects Detection Differently for DNA-DNA Vs. PNA-PNA OTP Probes Example 6A: Probe gap distance has little effect over 0-4 nucleotides on OTP detection using a DNA-DNA probe set. This assay utilized photocatalyst probe SEQ ID NO. 15 at 50 nM; profluorophore probe SEQ ID NO. 16 at 100 nM; and HIV-1 Pol/Int template SEQ ID NO. 14 or HIV-1 Pol/Int template with a gap distance of 0, 1, 3, or 4 nucleotides at 1 nM. The reducing agent was ascorbate at 5 mM; the buffer was 1× PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 245. The ΔRFUmax value is the measured full conversion of the same amount of the profluorophore probe reduced to fluorophore with a strong reducing agent (TCEP). The results (FIG. 6A) show that a gap distance of 0-4 nucleotides between the binding sites for the probes on a template has very little effect on the fluorescence output of the reaction.

Example 6B: Probe gap distance has a large effect over 0-2 nucleotides on OTP detection using a PNA-PNA probe set. This assay utilized photocatalyst probe SEQ ID NO. 24 at 25 nM; profluorophore probe SEQ ID NO. 25 at 100 nM; and HIV-1 shortened TAR template SEQ ID No. 32 or HIV-1 shortened TAR template with a gap distance of 0 or 1 nucleotide at 1 nM. The reducing agent was ascorbate at 5 mM; the buffer was 1× PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 250. The ΔRFUmax value is the measured full conversion of the same amount of the profluorophore probe reduced to fluorophore with a strong reducing agent (TCEP). The results (FIG. 6B) show that a gap distance of 0-2 nucleotides between the binding sites for PNA-PNA OTP probes on a template has a large effect on the fluorescence output of the reaction, with 2 nucleotides yielding a much higher fluorescence output compared to 0 nucleotides and a lesser increase compared to 1 nucleotide.

Example 7: A Single Nucleotide Mismatch is Detected by the OTP Reaction

Figure 7:
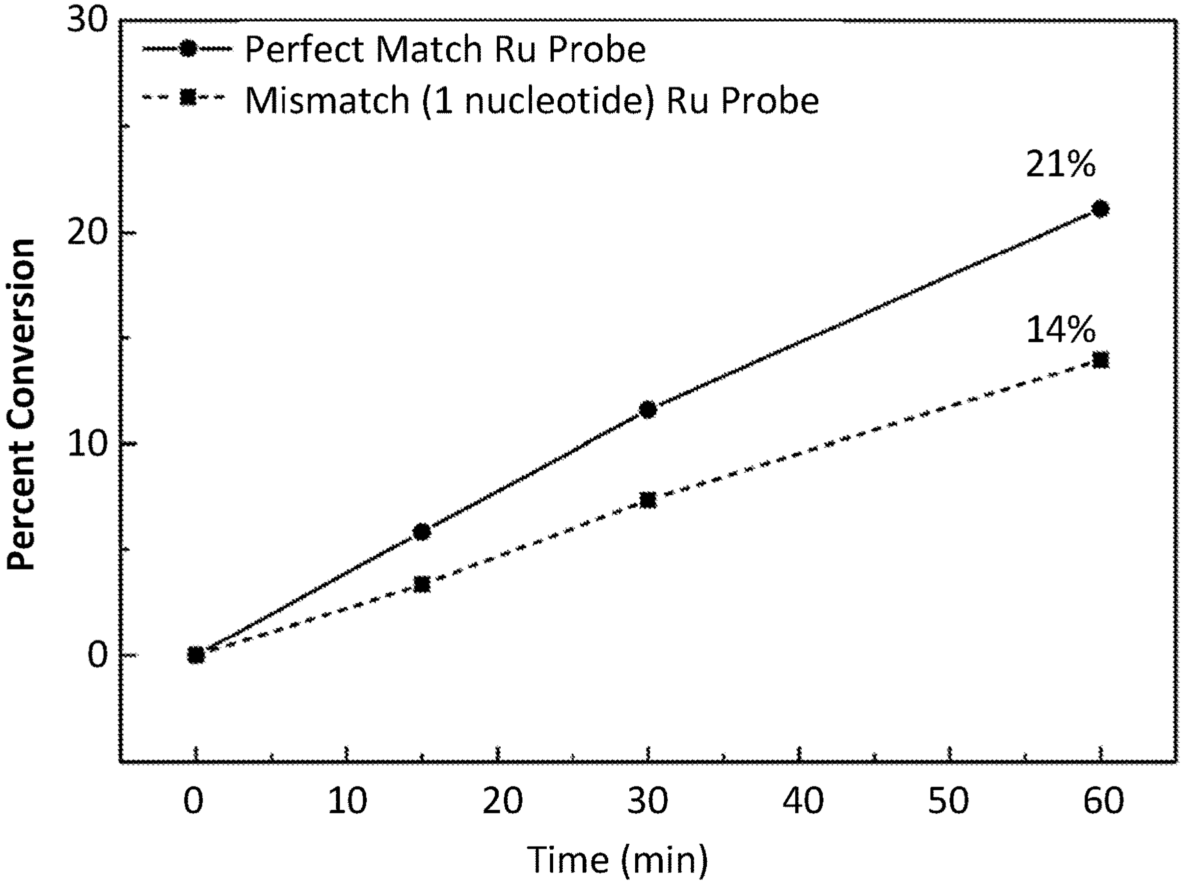
FIG. 7 shows the effect of single nucleotide mismatch between photocatalyst probe and target RNA sequence.

Example 7: A single nucleotide mismatch affects the OTP reaction. This assay utilized photocatalyst probe SEQ ID NO. 27 or SEQ ID NO. 28 (single mismatch) at 50 nM; profluorophore probe SEQ ID NO. 26 at 100 nM; and HIV-1 TAR RNA template SEQ ID No. 23 at 1 nM. The reducing agent was ascorbate at 5 mM; the buffer was 5× PBS, pH 7.4, with 0.05% polysorbate 20. An initial heating step was performed (95° C. for 2 min, 65° C. for 5 min) with the following reaction components: photocatalyst probe, PNA opener, template, and buffer. The reaction was placed at 4° C. and the profluorophore probe and reducing agent were added. The reaction was then performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 290. The ΔRFUmax value is the measured full conversion of the same amount of the profluorophore probe reduced to fluorophore with a strong reducing agent (TCEP). The results (FIG. 7) show that a single nucleotide mismatch within but not at an end of the photocatalyst probe reduces OTP detection by 7%.

Example 8: OTP Assay Detection is Highly Dependent on Profluorophore Probe Length Example 8: The OTP reaction requires probe length testing for optimal detection. This assay utilized photocatalyst probe SEQ ID NO. 15 at 50 nM; profluorophore probe SEQ ID NO. 16, 17, and 18 at 100 nM; and HIV-1 Pol/Int RNA template SEQ ID No. 14 at 1 nM. The reducing agent was ascorbate at 5 mM; the buffer was 1× PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 245. The ΔRFUmax value is the measured full conversion of the same amount of the profluorophore probe reduced to fluorophore with a strong reducing agent (TCEP). The results (FIG. 8) show that a shorter length (10 nucleotides) profluorophore probe is required for detection of 1 nM target RNA, while a longer length (15 and 18 nucleotides) profluorophore probe does not provide sufficient profluorophore probe cycling on and off the RNA target for 1 nM detection.

Example 9: Optimal Buffer Concentration for DNA-DNA Probe Set Targeting HIV-1 TAR RNA Example 9A: The OTP reaction using a DNA-DNA probe set with 1× PBS provides only low fluorescence detection of HIV-1 TAR RNA. This assay utilized photocatalyst probe SEQ ID NO. 27 at 50 nM; profluorophore probe SEQ ID NO. 26 at 100 nM; and HIV-1 TAR RNA template SEQ ID No. 23 at 0, 1, and 10 nM. The reducing agent was ascorbate at 5 mM; the buffer was 1×PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 290. The ΔRFUmax value is the measured full conversion of the same amount of the profluorophore probe reduced to fluorophore with a strong reducing agent (TCEP). The results (FIG. 9A) show that use of a 1× PBS buffer concentration does not provide for sufficient profluorophore probe cycling on and off the RNA target for 1 nM HIV-1 TAR RNA target detection.

Example 9B: The OTP reaction using a DNA-DNA probe set with 5× PBS provides greatly improved fluorescence detection of HIV-1 TAR RNA. This assay utilized photocatalyst probe SEQ ID NO. 27 at 50 nM; profluorophore probe SEQ ID NO. 26 at 100 nM; and HIV-1 TAR RNA template SEQ ID No. 23 at 0, 1, and 10 nM. The reducing agent was ascorbate at 5 mM; the buffer was 5× PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 290. The ΔRFUmax value is the measured full conversion of the same amount of the profluorophore probe reduced to fluorophore with a strong reducing agent (TCEP). The results (FIG. 9B) show that use of a 5× PBS buffer concentration provides sufficient profluorophore probe cycling on and off the RNA target for 1 nM HIV-1 TAR RNA target detection.

Example 10: Buffer Concentration for Improved Detection for PNA-PNA Probe Set Targeting HIV-1 TAR RNA Example 10A: The OTP reaction using a PNA-PNA probe set with 1× PBS provides suboptimal fluorescence detection of HIV-1 TAR RNA. This assay utilized photocatalyst probe SEQ ID NO. 24 at 25 nM; profluorophore probe SEQ ID NO. 25 at 100 nM; and HIV-1 TAR RNA template SEQ ID No. 23 at 0, 1, and 10 nM. The reducing agent was ascorbate at 5 mM; the buffer was 1× PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 250. The ΔRFUmax value is the measured full conversion of the same amount of the profluorophore probe reduced to fluorophore with a strong reducing agent (TCEP). The results (FIG. 10A) show that use of a 1× PBS buffer concentration does not provide for optimal detection of 1 and 10 nM HIV-1 TAR RNA target detection using a PNA-PNA probe set.

Example 10B: The OTP reaction using a PNA-PNA probe set with 0.1× PBS provides improved fluorescence detection of HIV-1 TAR RNA. This assay utilized photocatalyst probe SEQ ID NO. 24 at 25 nM; profluorophore probe SEQ ID NO. 25 at 100 nM; and HIV-1 TAR RNA template SEQ ID No. 23 at 0, 1, and 10 nM. The reducing agent was ascorbate at 5 mM; the buffer was 0.1× PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 250. The ΔRFUmax value is the measured full conversion of the same amount of the profluorophore probe reduced to fluorophore with a strong reducing agent (TCEP). The results (FIG. 10B) show that use of a 0.1× PBS buffer concentration provides better detection of 1 and 10 nM HIV-1 TAR RNA target detection using a PNA-PNA probe set.

Example 11: HIV-1 TAR RNA with Hybridized OTP Probes

Example 11: Schematic of HIV-1 TAR structure with an OTP probe pair hybridized to the stem-loop Region. Shown in FIG. 11 is an HIV-1 TAR predicted secondary structure (using any RNA secondary structure prediction free web software tool) with hybridized photocatalyst PNA probe (upper, right most, probe, spanning nucleotides 40 to 30 on HIV-1 TAR RNA) and hybridized profluorophore DNA/PNA probe (lower, left most, probe, spanning nucleotides 21 to 27 on HIV-1 TAR RNA).

Example 12: Profluorophores Incorporating Self-Immolative Linkers

Example 12A: In FIG. 12A, the self-immolative linker is shown circled in the structure of pyridinium-substituted rhodamine profluorophore. The pyridinium in the linker is reduced by the activated photocatalyst, causing self-immolation of the linker and release of the rhodamine-based fluorophore. The resulting fluorophore ends with an amine (—$NH_2$), after the release of carbon dioxide ($CO_2$) and the remainder of the linker.

Example 12B: In FIG. 12B, the self-immolative linker is shown circled in the structure of pyridinium-substituted fluorescein profluorophore. The pyridinium in the linker is reduced by the activated photocatalyst, causing self-immolation of the linker and release of the fluorescein-based fluorophore. The resulting fluorophore ends with a hydroxyl (—OH), after release of the linker.

Example 13: RNA Target Specificity Can Differ Dramatically for PNA-PNA vs. DNA-DNA Probe Sets Example 13A: Significant false-positive detection for negative control RNA with an HIV-1 Pol/Int PNA-PNA probe pair. This assay utilized photocatalyst probe SEQ ID NO. 19 at 50 nM; profluorophore probe SEQ ID NO. 20 at 100 nM; and in vitro-transcribed HIV-1 Gag RNA, at 0, 1 nM, and 10 nM. The reducing agent was ascorbate at 5 mM; the buffer was 0.05× PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 244. The ΔRFUmax value is the measured full conversion of the same amount of the profluorophore probe reduced to fluorophore with a strong reducing agent (TCEP). The results (FIG. 13A) show that the HIV-1 Pol/Int OTP using a PNA-PNA probe set is not specific in that it yields significant false positive detection above background, when tested with negative control HIV-1 RNA.

Example 13B: No false-positive detection for negative control RNA with an HIV-1 Pol/Int DNA-DNA probe pair. This assay utilized photocatalyst probe SEQ ID NO. 15 at 50 nM; profluorophore probe SEQ ID NO. 16 at 100 nM; and in vitro-transcribed HIV-1 Gag RNA, at 0, 1 nM, and 10 nM. The reducing agent was ascorbate at 5 mM; the buffer was 1× PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using a ΔRFUmax of 245. The ΔRFUmax value is the measured full conversion of the same amount of the profluorophore probe reduced to fluorophore with a strong reducing agent (TCEP). The results (FIG. 13A) show that the HIV-1 Pol/Int OTP is specific in that it does not yield a false positive, or any detection above background, when tested with negative control HIV-1 RNA.

Figure 14A:
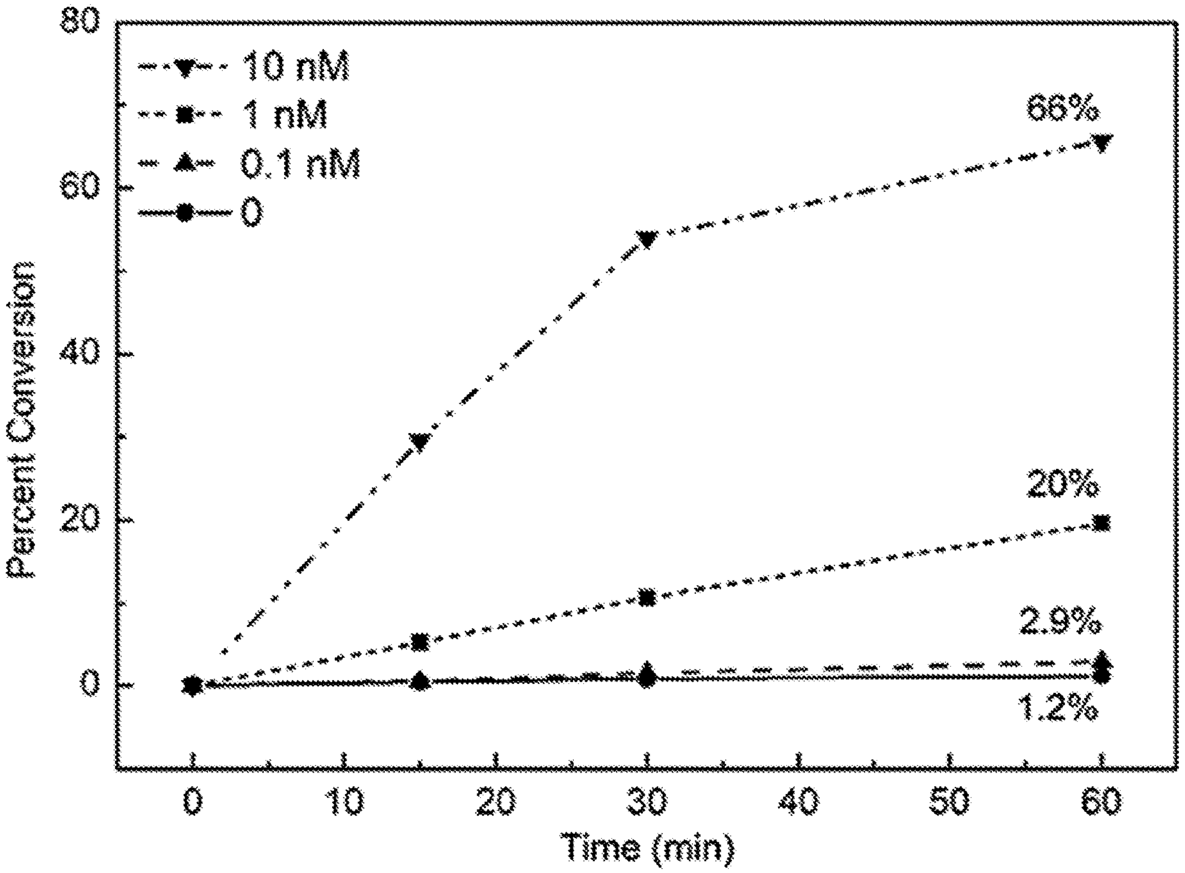
FIGS. 14A-14B show the reduction in background provided using a Pyridinium-Fluorescein PNA (FIG. 14A) or DNA (FIG. 14B) profluorophore probe for improved detection of HIV-1 TAR RNA.
Figure 14B:
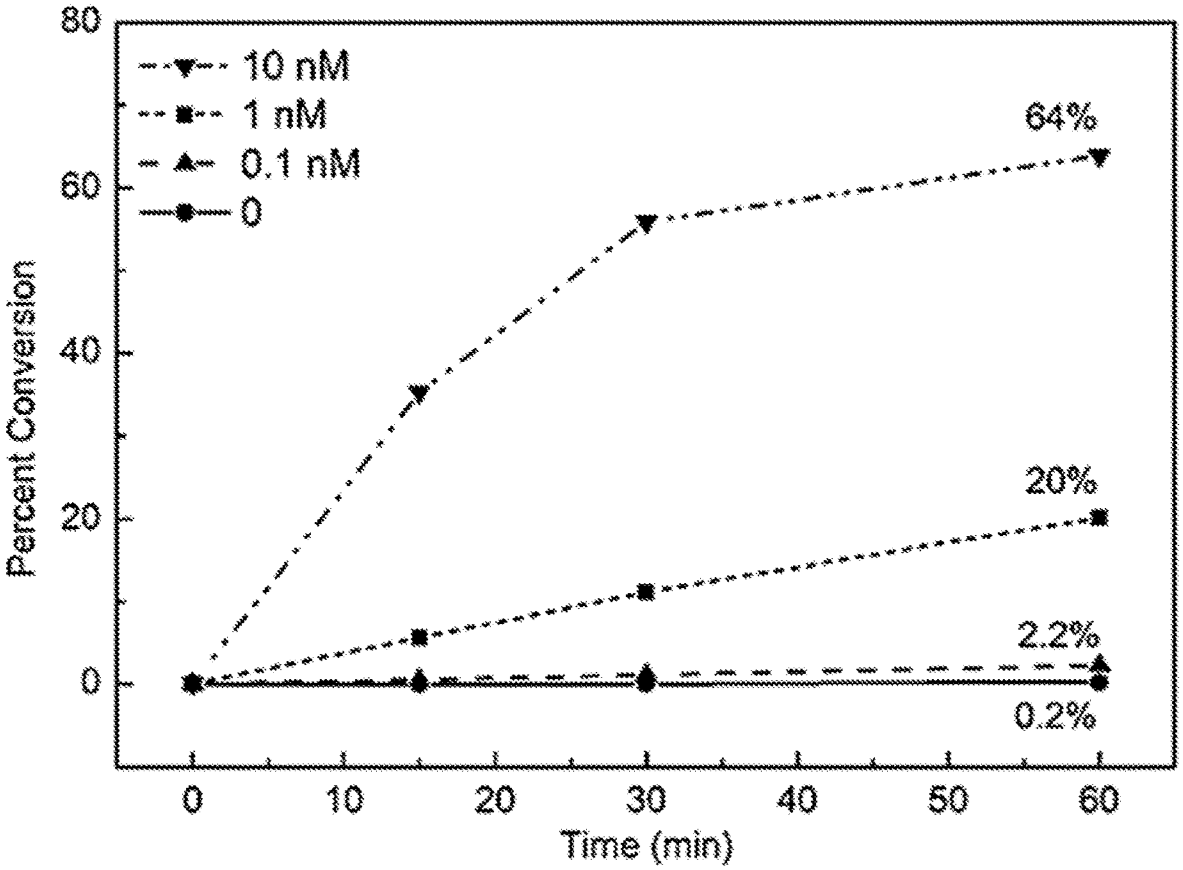

Example 14: Pyridinium-Fluorescein Profluorophore Probes can Reduce the Background Reaction Compared to the Azido-Coumarin Profluorophore Probes Example 14A: Quantitative detection of HIV-1 TAR RNA by PNA-PNA OTP probe set using a pyridinium-Fluorescein profluorophore PNA probe. This assay utilized photocatalyst probe SEQ ID NO. 24 at 25 nM; profluorophore probe SEQ ID NO. 33 at 100 nM; and HIV-1 shortened TAR RNA template SEQ ID No. 32 at 0, 100 pM, 1 nM, and 10 nM. The reducing agent was ascorbate at 5 mM; the buffer was 1× PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 480/525 nm. Percent conversion (profluorophore to fluorophore) was calculated using a ΔRFUmax of 50. The results (FIG. 14A) show that use of a pyridinium-Fluorescein profluorophore probe yields a lower background reaction (1.2%) when compared to Azido-Coumarin profluorophore probes (2-4%).

Example 14B: Quantitative detection of HIV-1 TAR RNA by DNA-DNA OTP probe set using a pyridinium-Fluorescein profluorophore DNA probe. This assay utilized photocatalyst probe SEQ ID NO. 27 at 25 nM; profluorophore probe SEQ ID NO. 35 at 100 nM; and HIV-1 shortened TAR RNA template SEQ ID No. 32 at 0, 100 pM, 1 nM, and 10 nM. The reducing agent was ascorbate at 5 mM; the buffer was 5× PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 460/520 nm. Percent conversion (profluorophore to fluorophore) was calculated using a ΔRFUmax of 100. The results (FIG. 14A) show that use of a pyridinium-Fluorescein profluorophore probe yields a lower background reaction (0.2%) when compared to Azido-Coumarin profluorophore probes (2-4%).

Example 15: Effect of Detergent Additive on Detection of HIV-1 TAR

Figure 15A:
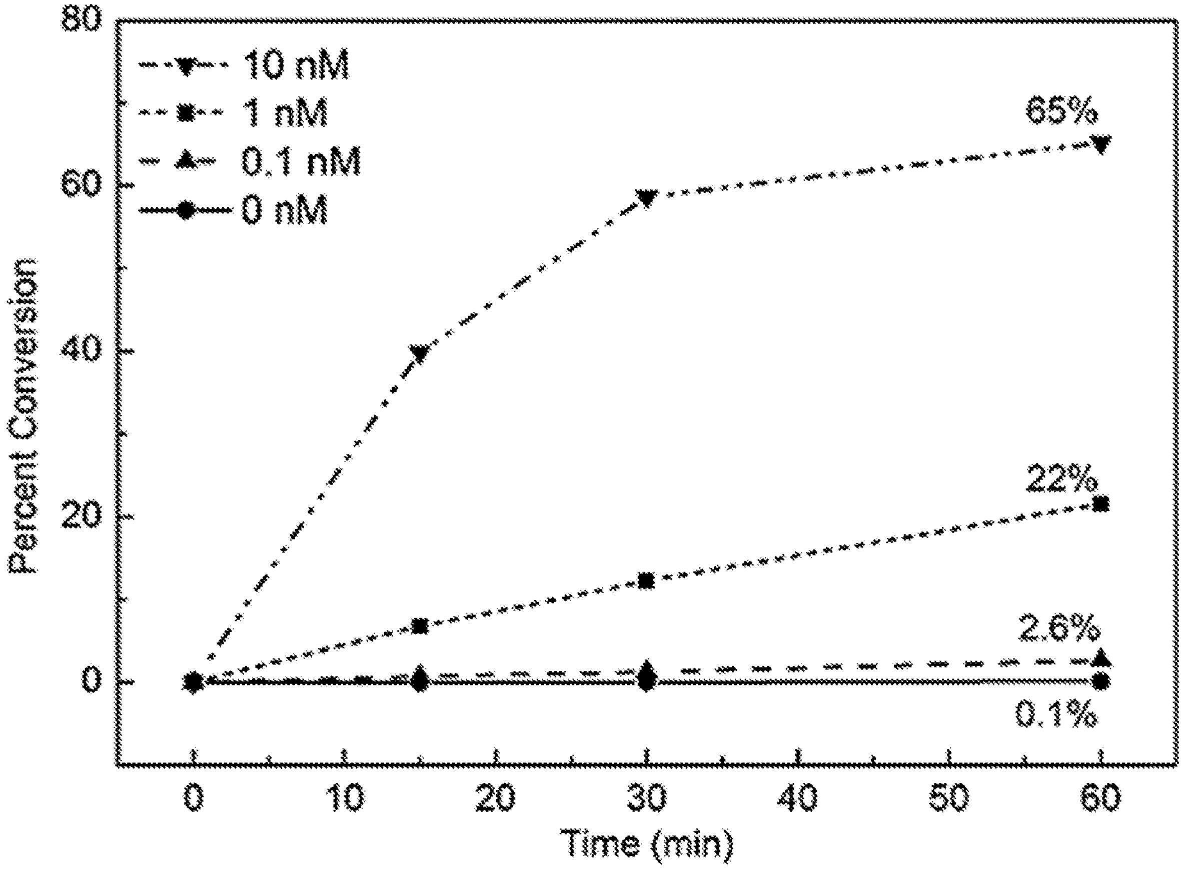
FIGS. 15A-15B show an improvement provided using digitonin (FIG. 15A) over polysorbate-20 (FIG. 15B) as the buffer additive with the Pyridinium-Fluorescein DNA profluorophore probe for improved detection of HIV-1 TAR RNA.
Figure 15B:
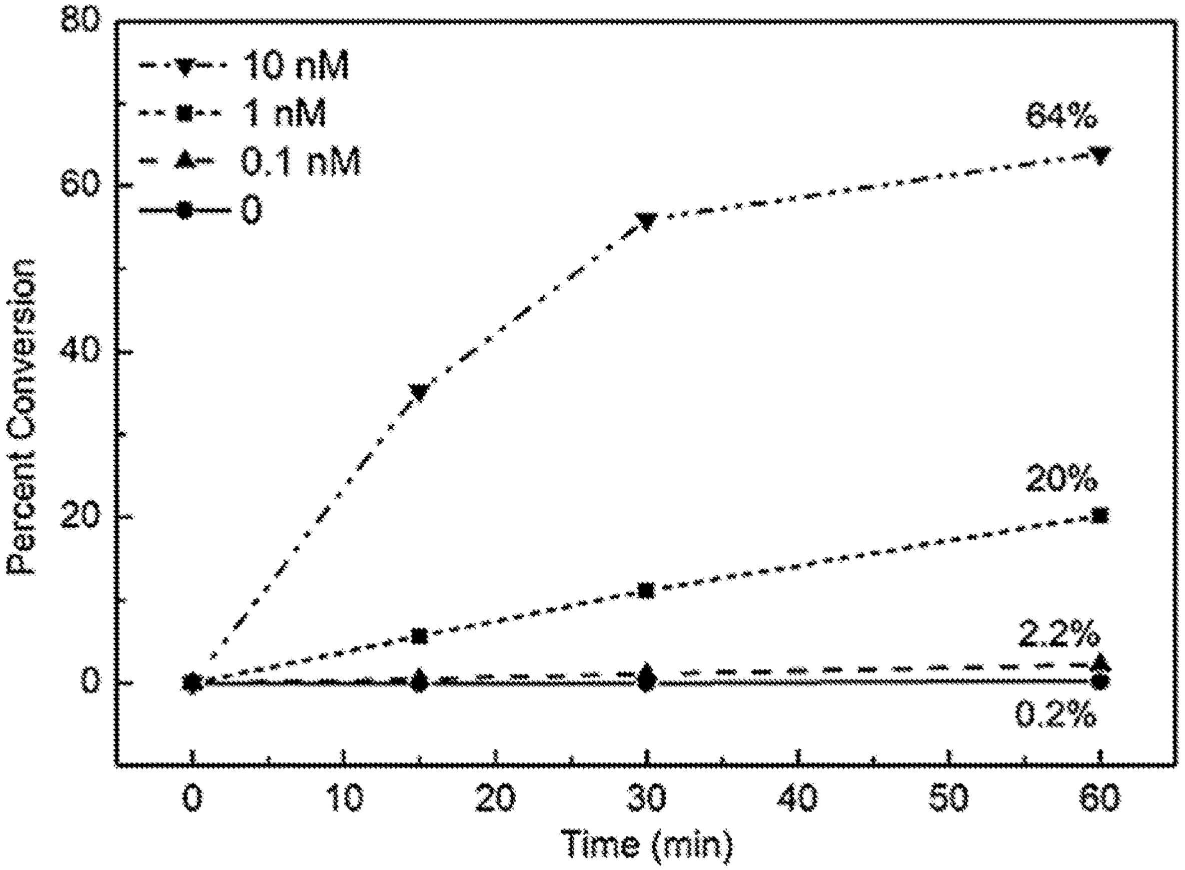

Example 15A: Quantitative detection of HIV-1 TAR RNA by DNA-DNA OTP probe set with added digitonin in reaction buffer. This assay utilized photocatalyst probe SEQ ID NO. 27 at 25 nM; profluorophore probe SEQ ID NO. 35 at 100 nM; and HIV-1 shortened TAR RNA template SEQ ID No. 32 at 0, 100 pM, 1 nM, and 10 nM. The reducing agent was ascorbate at 5 mM; the buffer was 5× PBS, pH 7.4, with 0.1% digitonin. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 460/520 nm. Percent conversion (profluorophore to fluorophore) was calculated using a ΔRFUmax of 100. The results in FIG. 15A show that the use of digitonin yields an improved detection of HIV-A TAR and a lower background reaction in comparison with polysorbate 20.

Example 15B: Quantitative detection of HIV-1 TAR RNA by DNA-DNA OTP probe set with added polysorbate 20 in reaction buffer. This assay utilized photocatalyst probe SEQ ID NO. 27 at 25 nM; profluorophore probe SEQ ID NO. 35 at 100 nM; and HIV-1 shortened TAR RNA template SEQ ID No. 32 at 0, 100 pM, 1 nM, and 10 nM. The reducing agent was ascorbate at 5 mM; the buffer was 5× PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 460/520 nm. Percent conversion (profluorophore to fluorophore) was calculated using a ΔRFUmax of 100.

Figure 16A:
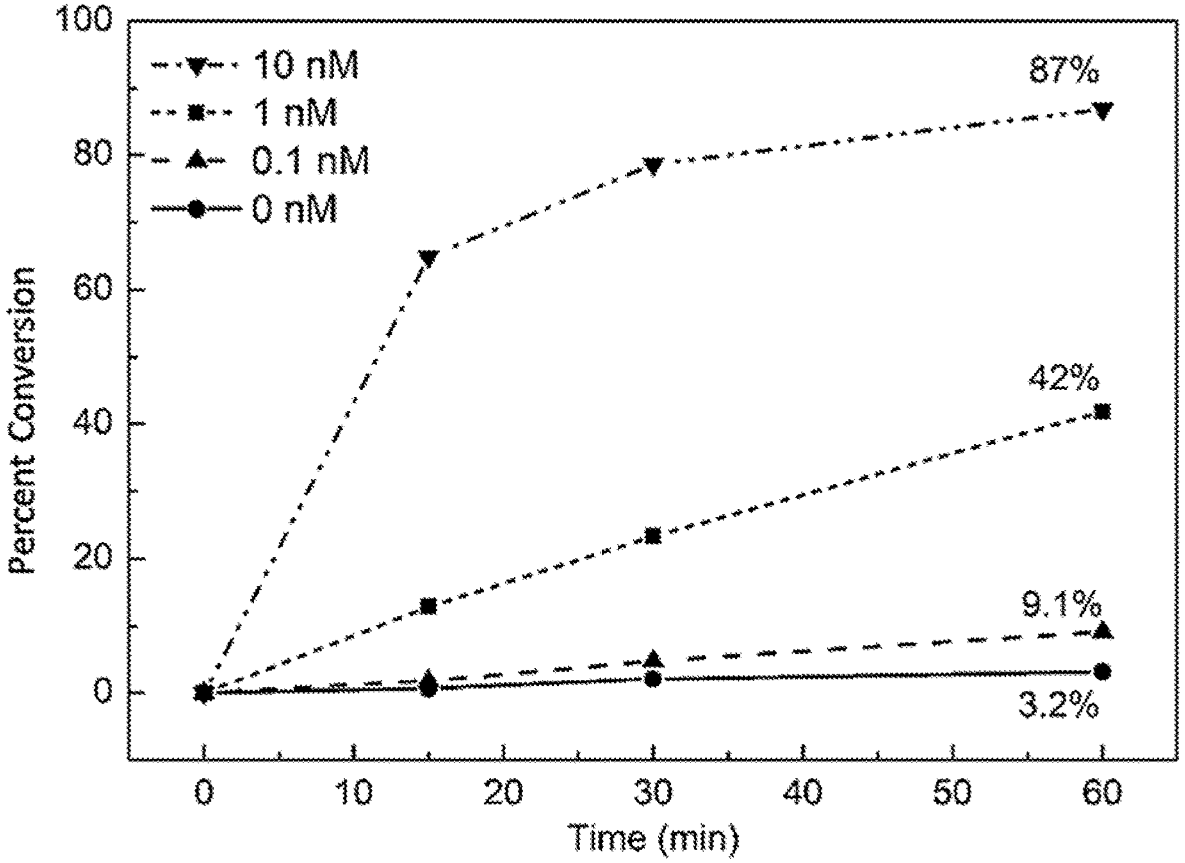
FIGS. 16A-16B show quantitative detection by OTP reaction of SARS-COV-2 Spike RNA (FIG. 16A) or SARS-COV-2 ORF8 RNA (FIG. 16B).

Example 16: In Vitro Detection of SARS-COV-2 Target RNA Sequences Example 16A: Quantitative detection by OTP of SARS-COV-2 Spike RNA. This assay utilized photocatalyst probe SEQ ID NO. 37 at 25 nM; profluorophore probe SEQ ID NO. 38 at 100 nM; and SARS-COV-2 Spike RNA template SEQ ID NO. 36, at 0, 100 pM, 1 nM, and 10 nM. The reducing agent was ascorbate at 5 mM; the buffer was 5× PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using the maximum change in relative fluorescence unit (ΔRFUmax) of 45. The ΔRFUmax value is the measured full conversion of the same amount of the profluorophore probe reduced to fluorophore with a strong reducing agent (TCEP). The results (FIG. 16A) show OTP detection at least as low as 100 pM for the SARS-COV-2 Spike RNA target sequence in vitro.

Figure 16B:
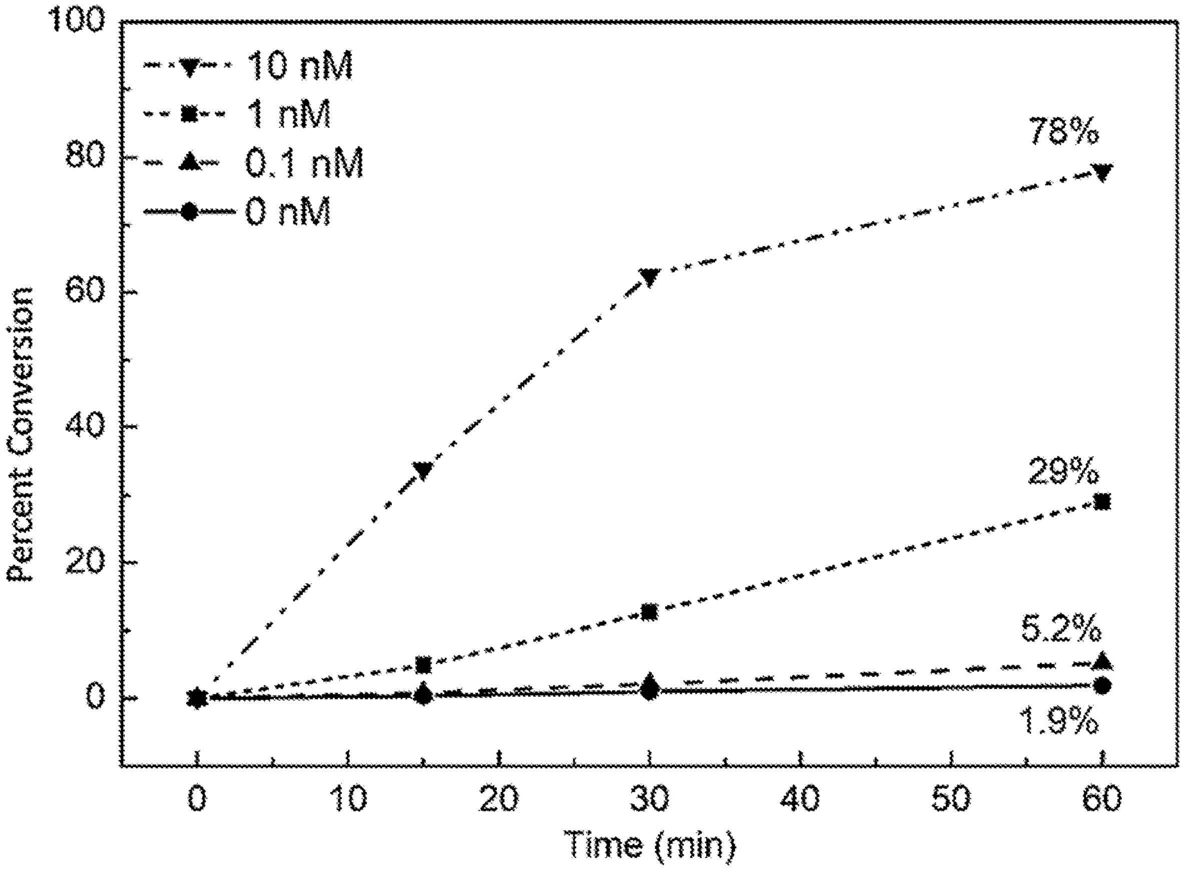

Example 16B: Quantitative detection by OTP of SARS-COV-2 ORF8 RNA. This assay utilized photocatalyst probe SEQ ID NO. 40 at 25 nM; profluorophore probe SEQ ID NO. 41 at 100 nM; and SARS-COV-2 ORF8 RNA template SEQ ID NO. 39, at 0, 100 pM, 1 nM, and 10 nM. The reducing agent was ascorbate at 5 mM; the buffer was 1× PBS, pH 7.4, with 0.05% polysorbate 20. The reaction was performed isothermally at 25° C. using a 455 nm light source with a +/−5 nm bandwidth filter and a filter to block light below 440 nm. Fluorescence output was measured in a fluorometer with a plate reader using excitation/emission wavelengths of 355/450 nm. Percent conversion (profluorophore to fluorophore) was calculated using the maximum change in relative fluorescence unit (ΔRFUmax) of 205. The ΔRFUmax value is the measured full conversion of the same amount of the profluorophore probe reduced to fluorophore with a strong reducing agent (TCEP). The results (FIG. 16B) show OTP detection at least as low as 100 pM for the SARS-COV-2 ORF8 RNA target sequence in vitro.

We claim:

1. A fluorogenic method for quantitatively detecting a target ribonucleic acid (RNA) sequence in a sample using a fluorogenic nucleic acid composition comprising at least one pair of oligonucleotide probes comprising a photocatalyst probe and a profluorophore probe, the method comprising:

a) hybridizing the photocatalyst probe to the target RNA sequence to form a hybridized sample in the reaction buffer in the presence or absence of a reducing agent;

b) the hybridizing in step a) is optionally performed in the presence of a DNA or PNA opener in the reaction buffer in the presence or absence of a reducing agent;

c) the hybridizing in step a) is optionally performed in the presence or absence of a DNA or PNA opener and exposing the mixture to denaturing conditions followed by a temperature 5° C. below the annealing temperature of the photocatalyst probe and/or opener to its target RNA sequence, in the reaction buffer in the presence or absence of a reducing agent;

d) hybridizing the profluorophore probe to the target RNA sequence to form a hybridized profluorophore probe, in the reaction buffer in the presence or absence of a reducing agent;

e) optionally performing steps a) and d) together, containing photocatalyst probe, profluorophore probe, and target RNA sequence, in the reaction buffer in the presence or absence of a reducing agent;

f) optionally performing steps b) and d) together, containing photocatalyst probe, profluorophore probe, DNA or PNA opener, and target RNA sequence, in the reaction buffer in the presence or absence of a reducing agent;

g) exposing the hybridization product from d), e), or f), comprising at least the target RNA sequence hybridized to the photocatalyst probe and to the profluorophore probe, optionally containing DNA or PNA opener, in reaction buffer to (i) light of a wavelength of about 440 nm to about 460 nm, and (ii) a reducing agent, thereby activating the photocatalyst to form a reduced, activated photocatalyst, which then spontaneously reduces the profluorophore on the hybridized profluorophore probe to a fluorophore, thereby forming a hybridized fluorophore probe and regenerating the photocatalyst;

h) denaturing the hybridized fluorophore probe from the target RNA sequence under conditions whereby the photocatalyst probe remains hybridized to the target RNA sequence;

i) optionally repeating step d), g) and step h); and j) detecting the amount of fluorescence emitted by the fluorophore using a fluorometer that provides the excitation wavelength for the fluorophore and can measure the emission wavelength of the fluorophore after excitation.

2. The method of claim 1, wherein the concentration of the profluorophore probe during the hybridization step is from about 25 nM to about 500 nM, or about 50 nM to about 200 nM, or about 100 nM;

the concentration of the photocatalyst probe during the hybridization step is from about 5 nM to about 200 nM, or about 25 to about 125 nM, or about 25 nM or 50 nM; and the reducing agent is sodium ascorbate, formamide, N-diisopropylethylamine, or NADPH.

3. The method of claim 1, wherein steps d), e), or f) and h) are performed under thermocycling conditions.

4. The method of claim 1, wherein step h) is performed at a temperature from about 40° C. to about 80° C., and step d), e), or f) is performed at a temperature from about 20° C. to about 60° C.

5. A fluorogenic method for quantitatively detecting a target ribonucleic acid (RNA) sequence in a sample using a fluorogenic nucleic acid kit comprising at least one pair of oligonucleotide probes comprising a photocatalyst probe and a profluorophore probe, the method comprising:

a) hybridizing the photocatalyst probe to the target RNA sequence to form a hybridized sample in the reaction buffer in the presence or absence of a reducing agent;

b) the hybridizing in step a) is optionally performed in the presence of a DNA or PNA opener in the reaction buffer in the presence or absence of a reducing agent;

c) the hybridizing in step a) is optionally performed in the presence or absence of a DNA or PNA opener and exposing the mixture to denaturing conditions followed by a temperature 5° C. below the annealing temperature of the photocatalyst probe and/or opener to its target RNA sequence, in the reaction buffer in the presence or absence of a reducing agent;

d) hybridizing the profluorophore probe to the target RNA sequence to form a hybridized profluorophore probe, in the reaction buffer in the presence or absence of a reducing agent;

e) optionally performing steps a) and d) together, containing photocatalyst probe, profluorophore probe, and target RNA sequence, in the reaction buffer in the presence or absence of a reducing agent;

f) optionally performing steps b) and d) together, containing photocatalyst probe, profluorophore probe, DNA or PNA opener, and target RNA sequence, in the reaction buffer in the presence or absence of a reducing agent;

g) exposing the hybridization product from d), e), or f), comprising at least the target RNA sequence hybridized to the photocatalyst probe and to the profluorophore probe, optionally containing DNA or PNA opener, in reaction buffer to (i) light of a wavelength of about 440 nm to about 460 nm, and (ii) a reducing agent, thereby activating the photocatalyst to form a reduced, activated photocatalyst, which then spontaneously reduces the profluorophore on the hybridized profluorophore probe to a fluorophore, thereby forming a hybridized fluorophore probe and regenerating the photocatalyst;

h) denaturing the hybridized fluorophore probe from the target RNA sequence under conditions whereby the photocatalyst probe remains hybridized to the target RNA sequence;

i) optionally repeating step d), g) and step h); and j) detecting the amount of fluorescence emitted by the fluorophore using a fluorometer that provides the excitation wavelength for the fluorophore and can measure the emission wavelength of the fluorophore after excitation.

6. The method of claim 1, wherein the photocatalyst probe comprises a first oligonucleotide covalently bound to a photocatalyst.

7. The method of claim 6, wherein the profluorophore probe comprises a second oligonucleotide covalently bound to a profluorophore.

8. The method of claim 7, wherein the covalent bond is a self-immolative covalent bond that is broken during a photoreduction reaction to release an activated fluorophore from the profluorophore probe.

9. The method of claim 7, wherein the photocatalyst is activatable by exposure to light and a reducing agent to form a reduced, activated photocatalyst such that, when both probes of the pair are hybridized to a target RNA sequence, is capable of photoreducing the profluorophore to form a detectable fluorophore.

10. The method of claim 1, wherein the profluorophore is:

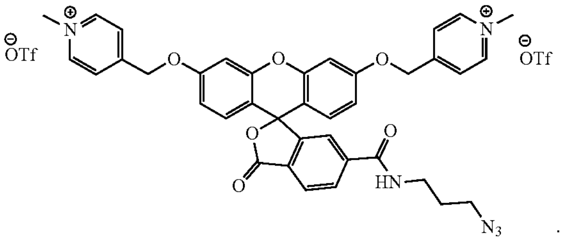

11. The method of claim 1, wherein the photocatalyst is:

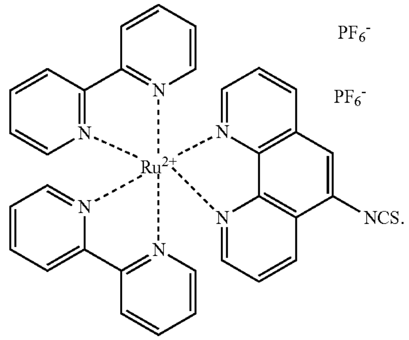

12. The method of claim 1, wherein the DNA or PNA opener is selected from:

(1) HIV-1 TAR DNA Opener
5'-GGTCTAACCAGAGAGACCCA-3' (SEQ ID NO: 30)

(2) HIV-1 TAR PNA Opener
5'-GGT*CTA*ACC*AGA*GAG*ACC*CA-3' (SEQ ID NO: 31), wherein A*, T*, C*, G* represent modified PNA base structures selected from:

(A)

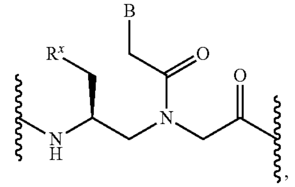

(B)

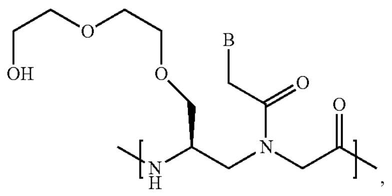

(C)

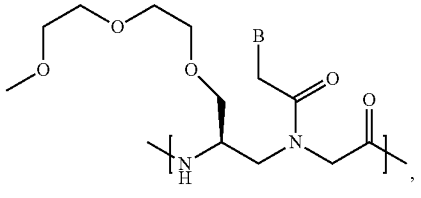

-continued (D)

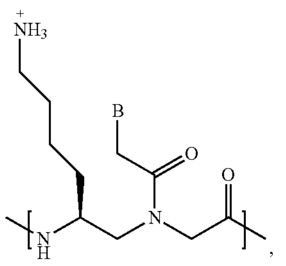

, and (E)

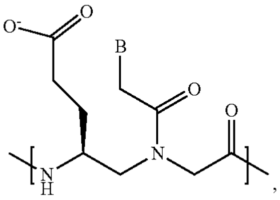

wherein $R^x$ is $-(OCH_2CH_2)_p-OH$ or $-(OCH_2CH_2)_p-OCH_3$, p is 0, 1, 2, 3, 4, or 5, and B is a nucleotide base adenine (A), thymine (T), guanine (G) or cytosine (C).

13. The method of claim 1, wherein the reducing agent is sodium ascorbate.

14. The method of claim 1, wherein the two probes in the pair are DNA probes, the two probes in the pair are PNA probes, or one probe in the pair is a DNA probe and the other probe is a PNA probe.

15. The method of claim 1, wherein the light in step g) is of a wavelength of 455 nm.

16. The method of claim 5, wherein:

(a) the photocatalyst probe comprises a first oligonucleotide covalently bound to a photocatalyst;

(b) the profluorophore probe comprises a second oligonucleotide covalently bound to a profluorophore, optionally wherein the covalent bond is a self-immolative covalent bond that is broken during a photoreduction reaction to release an activated fluorophore from the profluorophore probe, and/or (c) the photocatalyst is activatable by exposure to light and a reducing agent to form a reduced, activated photocatalyst such that, when both probes of the pair are hybridized to a target RNA sequence, is capable of photoreducing the profluorophore to form a detectable fluorophore.

17. The method of claim 5, wherein the profluorophore is:

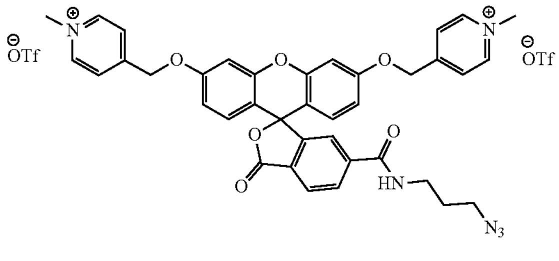

.

18. The method of claim 5, wherein the photocatalyst is:

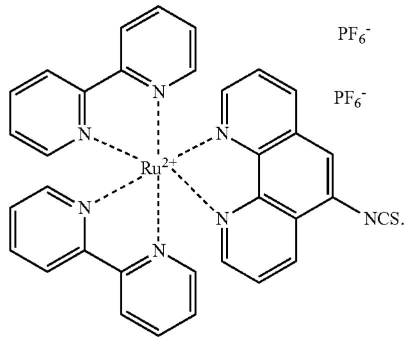

19. The method of claim 5, wherein the DNA or PNA opener is selected from:

(1) HIV-1 TAR DNA Opener

5'-GGTCTAACCAGAGAGACCCA-3' (SEQ ID NO: 30)

(2) HIV-1 TAR PNA Opener

5'-GGT*CTA*ACC*AGA*GAG*ACC*CA-3' (SEQ ID NO: 31), wherein A*, T*, C*, G* represent modified PNA base structures selected from:

(A)

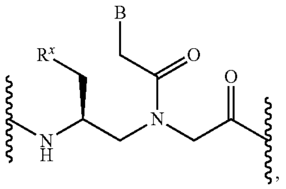

(B)

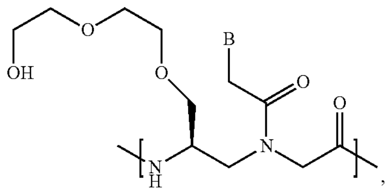

(C)

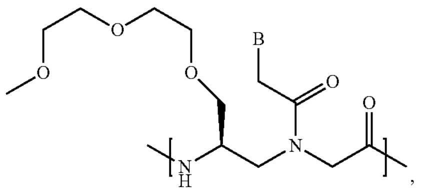

(D)

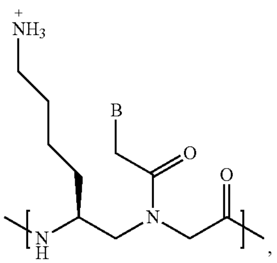

, and

-continued
(E)
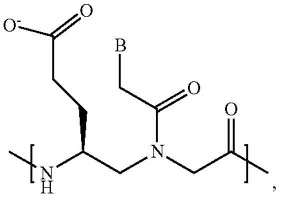
wherein $R^x$ is —$(OCH_2CH_2)_p$—OH or —$(OCH_2CH_2)_p$—$OCH_3$, p is 0, 1, 2, 3, 4, or 5, and B is a nucleotide base adenine (A), thymine (T), guanine (G) or cytosine (C).
20. The method of claim 5, wherein the light in step g) is of a wavelength of 455 nm.
* * * * *

SEQUENCE LISTING

<160> NUMBER OF SEQ ID NOS: 45

<210> SEQ ID NO 1
<211> LENGTH: 21
<212> TYPE: DNA
<213> ORGANISM: Artificial Sequence
<220> FEATURE:
<223> OTHER INFORMATION: Synthetic: HIV-1 Pol/Int DNA Probe

<400> SEQUENCE: 1
gcactgacta atttatctac t 21

<210> SEQ ID NO 2
<211> LENGTH: 10
<212> TYPE: DNA
<213> ORGANISM: Artificial Sequence
<220> FEATURE:
<223> OTHER INFORMATION: Synthetic: HIV-1 Pol/Int DNA Probe

<400> SEQUENCE: 2
ttcatttcct 10

<210> SEQ ID NO 3
<211> LENGTH: 15
<212> TYPE: DNA
<213> ORGANISM: Artificial Sequence
<220> FEATURE:
<223> OTHER INFORMATION: Synthetic: HIV-1 Pol/Int DNA Probe

<400> SEQUENCE: 3
ttcatttcct ccaat 15

<210> SEQ ID NO 4
<211> LENGTH: 18
<212> TYPE: DNA
<213> ORGANISM: Artificial Sequence
<220> FEATURE:
<223> OTHER INFORMATION: Synthetic: HIV-1 Pol/Int DNA Probe

<400> SEQUENCE: 4
ttcatttcct ccaattcc 18

<210> SEQ ID NO 5
<211> LENGTH: 10
<212> TYPE: DNA
<213> ORGANISM: Artificial Sequence
<220> FEATURE:
<223> OTHER INFORMATION: Synthetic: HIV-1 Pol/Int PNA Probe
<220> FEATURE:
<221> NAME/KEY: misc_feature
<223> OTHER INFORMATION: 5' Acetyl-O-
<220> FEATURE:
<221> NAME/KEY: misc_feature
<223> OTHER INFORMATION: 3' -Lys

<400> SEQUENCE: 5
tttatctact 10

<210> SEQ ID NO 6
<211> LENGTH: 8
<212> TYPE: DNA
<213> ORGANISM: Artificial Sequence
<220> FEATURE:
<223> OTHER INFORMATION: Synthetic: HIV-1 Pol/Int PNA Probe
<220> FEATURE:
<221> NAME/KEY: misc_feature
<223> OTHER INFORMATION: 3' -O linker

<400> SEQUENCE: 6 ttcatttc 8

<210> SEQ ID NO 7
<211> LENGTH: 7
<212> TYPE: DNA
<213> ORGANISM: Artificial Sequence
<220> FEATURE:
<223> OTHER INFORMATION: Synthetic: HIV-1 Pol/Int PNA Probe
<220> FEATURE:
<221> NAME/KEY: misc_feature
<223> OTHER INFORMATION: 3' -O linker

<400> SEQUENCE: 7 ttcattt 7

<210> SEQ ID NO 8
<211> LENGTH: 6
<212> TYPE: DNA
<213> ORGANISM: Artificial Sequence
<220> FEATURE:
<223> OTHER INFORMATION: Synthetic: HIV-1 Pol/Int PNA Probe
<220> FEATURE:
<221> NAME/KEY: misc_feature
<223> OTHER INFORMATION: 3' -O linker

<400> SEQUENCE: 8 ttcatt 6

<210> SEQ ID NO 9
<211> LENGTH: 10
<212> TYPE: DNA
<213> ORGANISM: Artificial Sequence
<220> FEATURE:
<223> OTHER INFORMATION: Synthetic: HIV-1 TAR PNA Probe
<220> FEATURE:
<221> NAME/KEY: misc_feature
<223> OTHER INFORMATION: 5' Acetyl-O-
<220> FEATURE:
<221> NAME/KEY: misc_feature
<223> OTHER INFORMATION: 3' -Lys
<220> FEATURE:
<221> NAME/KEY: modified_base
<222> LOCATION: (2)..(2)
<223> OTHER INFORMATION: modified PNA monomer
<220> FEATURE:
<221> NAME/KEY: modified_base
<222> LOCATION: (5)..(5)
<223> OTHER INFORMATION: modified PNA monomer
<220> FEATURE:
<221> NAME/KEY: modified_base
<222> LOCATION: (8)..(8)
<223> OTHER INFORMATION: modified PNA monomer

<400> SEQUENCE: 9
gagctcccag 10

<210> SEQ ID NO 10
<211> LENGTH: 18
<212> TYPE: DNA
<213> ORGANISM: Artificial Sequence
<220> FEATURE:
<223> OTHER INFORMATION: Synthetic: HIV-1 TAR DNA Probe

<400> SEQUENCE: 10
tagccagaga gctcccag 18

<210> SEQ ID NO 11
<211> LENGTH: 8

-continued

<212> TYPE: DNA
<213> ORGANISM: Artificial Sequence
<220> FEATURE:
<223> OTHER INFORMATION: Synthetic: HIV-1 TAR PNA Probe
<220> FEATURE:
<221> NAME/KEY: misc_feature
<223> OTHER INFORMATION: 3' -O linker
<220> FEATURE:
<221> NAME/KEY: modified_base
<222> LOCATION: (3)..(3)
<223> OTHER INFORMATION: modified PNA monomer
<220> FEATURE:
<221> NAME/KEY: modified_base
<222> LOCATION: (6)..(6)
<223> OTHER INFORMATION: modified PNA monomer

<400> SEQUENCE: 11 tcagatct 8

<210> SEQ ID NO 12
<211> LENGTH: 8
<212> TYPE: DNA
<213> ORGANISM: Artificial Sequence
<220> FEATURE:
<223> OTHER INFORMATION: Synthetic: HIV-1 TAR DNA Probe

<400> SEQUENCE: 12 tcagatct 8

<210> SEQ ID NO 13
<211> LENGTH: 11
<212> TYPE: DNA
<213> ORGANISM: Artificial Sequence
<220> FEATURE:
<223> OTHER INFORMATION: Synthetic: HIV-1 TAR DNA Probe

<400> SEQUENCE: 13
tcagatctgg t 11

<210> SEQ ID NO 14
<211> LENGTH: 45
<212> TYPE: RNA
<213> ORGANISM: Artificial Sequence
<220> FEATURE:
<223> OTHER INFORMATION: Synthetic: HIV-1 Pol/Int Target RNA Sequence

<400> SEQUENCE: 14
gaauuggagg aaaugaacaa guagauaaau uagucagugc uggaa 45

<210> SEQ ID NO 15
<211> LENGTH: 21
<212> TYPE: DNA
<213> ORGANISM: Artificial Sequence
<220> FEATURE:
<223> OTHER INFORMATION: Synthetic: HIV-1 Pol/Int DNA Probe
<220> FEATURE:
<221> NAME/KEY: misc_feature
<223> OTHER INFORMATION: 3' -Ru

<400> SEQUENCE: 15
gcactgacta atttatctac t 21

<210> SEQ ID NO 16
<211> LENGTH: 10
<212> TYPE: DNA
<213> ORGANISM: Artificial Sequence
<220> FEATURE:
<223> OTHER INFORMATION: Synthetic: HIV-1 Pol/Int DNA Probe
<220> FEATURE:

-continued

<221> NAME/KEY: misc_feature
<223> OTHER INFORMATION: 5' Azido-Coumarin-

<400> SEQUENCE: 16
ttcatttcct 10

<210> SEQ ID NO 17
<211> LENGTH: 15
<212> TYPE: DNA
<213> ORGANISM: Artificial Sequence
<220> FEATURE:
<223> OTHER INFORMATION: Synthetic: HIV-1 Pol/Int DNA Probe
<220> FEATURE:
<221> NAME/KEY: misc_feature
<223> OTHER INFORMATION: 5' Azido-Coumarin-

<400> SEQUENCE: 17
ttcatttcct ccaat 15

<210> SEQ ID NO 18
<211> LENGTH: 18
<212> TYPE: DNA
<213> ORGANISM: Artificial Sequence
<220> FEATURE:
<223> OTHER INFORMATION: Synthetic: HIV-1 Pol/Int DNA Probe
<220> FEATURE:
<221> NAME/KEY: misc_feature
<223> OTHER INFORMATION: 5' Azido-Coumarin-

<400> SEQUENCE: 18
ttcatttcct ccaattcc 18

<210> SEQ ID NO 19
<211> LENGTH: 10
<212> TYPE: DNA
<213> ORGANISM: Artificial Sequence
<220> FEATURE:
<223> OTHER INFORMATION: Synthetic: HIV-1 Pol/Int PNA Probe
<220> FEATURE:
<221> NAME/KEY: misc_feature
<223> OTHER INFORMATION: 5' Acetyl-O-
<220> FEATURE:
<221> NAME/KEY: misc_feature
<223> OTHER INFORMATION: 3' -Lys-Ru

<400> SEQUENCE: 19
tttatctact 10

<210> SEQ ID NO 20
<211> LENGTH: 8
<212> TYPE: DNA
<213> ORGANISM: Artificial Sequence
<220> FEATURE:
<223> OTHER INFORMATION: Synthetic: HIV-1 Pol/Int PNA Probe
<220> FEATURE:
<221> NAME/KEY: misc_feature
<223> OTHER INFORMATION: 5' Azido-Coumarin-
<220> FEATURE:
<221> NAME/KEY: misc_feature
<223> OTHER INFORMATION: 3' -O linker

<400> SEQUENCE: 20 ttcatttc 8

<210> SEQ ID NO 21
<211> LENGTH: 7
<212> TYPE: DNA
<213> ORGANISM: Artificial Sequence
<220> FEATURE:

<223> OTHER INFORMATION: Synthetic: HIV-1 Pol/Int PNA Probe
<220> FEATURE:
<221> NAME/KEY: misc_feature
<223> OTHER INFORMATION: 5' Azido-Coumarin-
<220> FEATURE:
<221> NAME/KEY: misc_feature
<223> OTHER INFORMATION: 3' -O linker

<400> SEQUENCE: 21 ttcattt 7

<210> SEQ ID NO 22
<211> LENGTH: 6
<212> TYPE: DNA
<213> ORGANISM: Artificial Sequence
<220> FEATURE:
<223> OTHER INFORMATION: Synthetic: HIV-1 Pol/Int PNA Probe
<220> FEATURE:
<221> NAME/KEY: misc_feature
<223> OTHER INFORMATION: 5' Azido-Coumarin-
<220> FEATURE:
<221> NAME/KEY: misc_feature
<223> OTHER INFORMATION: 3' -O linker

<400> SEQUENCE: 22 ttcatt 6

<210> SEQ ID NO 23
<211> LENGTH: 61
<212> TYPE: RNA
<213> ORGANISM: Artificial Sequence
<220> FEATURE:
<223> OTHER INFORMATION: Synthetic: HIV-1 TAR Target RNA Sequence

<400> SEQUENCE: 23
ugggucucuc ugguuagacc agaucugagc cugggagcuc ucuggcuaac uagggaaccc 60
a 61

<210> SEQ ID NO 24
<211> LENGTH: 10
<212> TYPE: DNA
<213> ORGANISM: Artificial Sequence
<220> FEATURE:
<223> OTHER INFORMATION: Synthetic: HIV-1 TAR PNA Probe
<220> FEATURE:
<221> NAME/KEY: misc_feature
<223> OTHER INFORMATION: 5' Acetyl-O-
<220> FEATURE:
<221> NAME/KEY: misc_feature
<223> OTHER INFORMATION: 3' -Lys-Ru
<220> FEATURE:
<221> NAME/KEY: modified_base
<222> LOCATION: (2)..(2)
<223> OTHER INFORMATION: modified PNA monomer
<220> FEATURE:
<221> NAME/KEY: modified_base
<222> LOCATION: (5)..(5)
<223> OTHER INFORMATION: modified PNA monomer
<220> FEATURE:
<221> NAME/KEY: modified_base
<222> LOCATION: (8)..(8)
<223> OTHER INFORMATION: modified PNA monomer

<400> SEQUENCE: 24
gagctcccag 10

<210> SEQ ID NO 25
<211> LENGTH: 8
<212> TYPE: DNA
<213> ORGANISM: Artificial Sequence
<220> FEATURE:
<223> OTHER INFORMATION: Synthetic: HIV-1 TAR PNA Probe
<220> FEATURE:
<221> NAME/KEY: misc_feature
<223> OTHER INFORMATION: 5' Azido-Coumarin-
<220> FEATURE:
<221> NAME/KEY: misc_feature
<223> OTHER INFORMATION: 3' -O linker
<220> FEATURE:
<221> NAME/KEY: modified_base
<222> LOCATION: (3)..(3)
<223> OTHER INFORMATION: modified PNA monomer
<220> FEATURE:
<221> NAME/KEY: modified_base
<222> LOCATION: (6)..(6)
<223> OTHER INFORMATION: modified PNA monomer

<400> SEQUENCE: 25 tcagatct 8

<210> SEQ ID NO 26
<211> LENGTH: 8
<212> TYPE: DNA
<213> ORGANISM: Artificial Sequence
<220> FEATURE:
<223> OTHER INFORMATION: Synthetic: HIV-1 TAR DNA Probe
<220> FEATURE:
<221> NAME/KEY: misc_feature
<223> OTHER INFORMATION: 5' Azido-Coumarin-

<400> SEQUENCE: 26 tcagatct 8

<210> SEQ ID NO 27
<211> LENGTH: 18
<212> TYPE: DNA
<213> ORGANISM: Artificial Sequence
<220> FEATURE:
<223> OTHER INFORMATION: Synthetic: HIV-1 TAR DNA Probe
<220> FEATURE:
<221> NAME/KEY: misc_feature
<223> OTHER INFORMATION: 3' -Ru

<400> SEQUENCE: 27
tagccagaga gctcccag 18

<210> SEQ ID NO 28
<211> LENGTH: 18
<212> TYPE: DNA
<213> ORGANISM: Artificial Sequence
<220> FEATURE:
<223> OTHER INFORMATION: Synthetic: HIV-1 TAR DNA Probe
<220> FEATURE:
<221> NAME/KEY: misc_feature
<223> OTHER INFORMATION: 3' -Ru

<400> SEQUENCE: 28
tagccagaga actcccag 18

<210> SEQ ID NO 29
<211> LENGTH: 11
<212> TYPE: DNA
<213> ORGANISM: Artificial Sequence
<220> FEATURE:
<223> OTHER INFORMATION: Synthetic: HIV-1 TAR DNA Probe
<220> FEATURE:
<221> NAME/KEY: misc_feature
<223> OTHER INFORMATION: 5' Azido-Coumarin-

<400> SEQUENCE: 29
tcagatctgg t 11

<210> SEQ ID NO 30
<211> LENGTH: 20
<212> TYPE: DNA
<213> ORGANISM: Artificial Sequence
<220> FEATURE:
<223> OTHER INFORMATION: Synthetic: HIV-1 TAR DNA Opener

<400> SEQUENCE: 30
ggtctaacca gagagaccca 20

<210> SEQ ID NO 31
<211> LENGTH: 20
<212> TYPE: DNA
<213> ORGANISM: Artificial Sequence
<220> FEATURE:
<223> OTHER INFORMATION: Synthetic: HIV-1 TAR PNA Opener
<220> FEATURE:
<221> NAME/KEY: modified_base
<222> LOCATION: (3)..(3)
<223> OTHER INFORMATION: modified PNA monomer
<220> FEATURE:
<221> NAME/KEY: modified_base
<222> LOCATION: (6)..(6)
<223> OTHER INFORMATION: modified PNA monomer
<220> FEATURE:
<221> NAME/KEY: modified_base
<222> LOCATION: (9)..(9)
<223> OTHER INFORMATION: modified PNA monomer
<220> FEATURE:
<221> NAME/KEY: modified_base
<222> LOCATION: (12)..(12)
<223> OTHER INFORMATION: modified PNA monomer
<220> FEATURE:
<221> NAME/KEY: modified_base
<222> LOCATION: (15)..(15)
<223> OTHER INFORMATION: modified PNA monomer
<220> FEATURE:
<221> NAME/KEY: modified_base
<222> LOCATION: (18)..(18)
<223> OTHER INFORMATION: modified PNA monomer

<400> SEQUENCE: 31
ggtctaacca gagagaccca 20

<210> SEQ ID NO 32
<211> LENGTH: 22
<212> TYPE: RNA
<213> ORGANISM: Artificial Sequence
<220> FEATURE:
<223> OTHER INFORMATION: Synthetic: HIV-1 Shortened TAR Target RNA
Sequence

<400> SEQUENCE: 32
cagaucugag ccugggagcu cu 22

<210> SEQ ID NO 33
<211> LENGTH: 8
<212> TYPE: DNA
<213> ORGANISM: Artificial Sequence
<220> FEATURE:
<223> OTHER INFORMATION: Synthetic: HIV-1 TAR PNA Probe
<220> FEATURE:
<221> NAME/KEY: misc_feature
<223> OTHER INFORMATION: 5' Pyridinium-Fluorescein-
<220> FEATURE:
<221> NAME/KEY: misc_feature
<223> OTHER INFORMATION: 3' -O linker
<220> FEATURE:
<221> NAME/KEY: modified_base
<222> LOCATION: (2)..(2)

<223> OTHER INFORMATION: modified PNA monomer
<220> FEATURE:
<221> NAME/KEY: modified_base
<222> LOCATION: (5)..(5)
<223> OTHER INFORMATION: modified PNA monomer
<220> FEATURE:
<221> NAME/KEY: modified_base
<222> LOCATION: (8)..(8)
<223> OTHER INFORMATION: modified PNA monomer

<400> SEQUENCE: 33 tcagatct 8

<210> SEQ ID NO 34
<211> LENGTH: 8
<212> TYPE: DNA
<213> ORGANISM: Artificial Sequence
<220> FEATURE:
<223> OTHER INFORMATION: Synthetic: HIV-1 TAR PNA Probe
<220> FEATURE:
<221> NAME/KEY: misc_feature
<223> OTHER INFORMATION: 5' Pyridinium-Fluorescein-O
<220> FEATURE:
<221> NAME/KEY: misc_feature
<223> OTHER INFORMATION: 3' -O linker
<220> FEATURE:
<221> NAME/KEY: modified_base
<222> LOCATION: (2)..(2)
<223> OTHER INFORMATION: modified PNA monomer
<220> FEATURE:
<221> NAME/KEY: modified_base
<222> LOCATION: (5)..(5)
<223> OTHER INFORMATION: modified PNA monomer
<220> FEATURE:
<221> NAME/KEY: modified_base
<222> LOCATION: (8)..(8)
<223> OTHER INFORMATION: modified PNA monomer

<400> SEQUENCE: 34 tcagatct 8

<210> SEQ ID NO 35
<211> LENGTH: 8
<212> TYPE: DNA
<213> ORGANISM: Artificial Sequence
<220> FEATURE:
<223> OTHER INFORMATION: Synthetic: HIV-1 TAR DNA Probe

<400> SEQUENCE: 35 tcagatct 8

<210> SEQ ID NO 36
<211> LENGTH: 34
<212> TYPE: RNA
<213> ORGANISM: Artificial Sequence
<220> FEATURE:
<223> OTHER INFORMATION: Synthetic: SARS-CoV-2 Spike (S) Target RNA
Sequence

<400> SEQUENCE: 36
acccauuggu gcagguauau gcgcuaguua ucag 34

<210> SEQ ID NO 37
<211> LENGTH: 22
<212> TYPE: DNA
<213> ORGANISM: Artificial Sequence
<220> FEATURE:
<223> OTHER INFORMATION: Synthetic: SARS-CoV-2 Spike DNA Probe
<220> FEATURE:
<221> NAME/KEY: misc_feature
<223> OTHER INFORMATION: 3' -Ru

<400> SEQUENCE: 37
tgataactag cgcatatacc tg 22

<210> SEQ ID NO 38
<211> LENGTH: 8
<212> TYPE: DNA
<213> ORGANISM: Artificial Sequence
<220> FEATURE:
<223> OTHER INFORMATION: Synthetic: SARS-CoV-2 Spike DNA Probe
<220> FEATURE:
<221> NAME/KEY: misc_feature
<223> OTHER INFORMATION: 5' Azido-Coumarin-

<400> SEQUENCE: 38 ccaatggg 8

<210> SEQ ID NO 39
<211> LENGTH: 35
<212> TYPE: RNA
<213> ORGANISM: Artificial Sequence
<220> FEATURE:
<223> OTHER INFORMATION: Synthetic: SARS-CoV-2 ORF8 Target RNA Sequence

<400> SEQUENCE: 39
gagcuagaaa aucagcaccu uuaauugaau ugugc 35

<210> SEQ ID NO 40
<211> LENGTH: 21
<212> TYPE: DNA
<213> ORGANISM: Artificial Sequence
<220> FEATURE:
<223> OTHER INFORMATION: Synthetic: SARS-CoV-2 ORF8 DNA Probe
<220> FEATURE:
<221> NAME/KEY: misc_feature
<223> OTHER INFORMATION: 3' -Ru

<400> SEQUENCE: 40
cacaattcaa ttaaaggtgc t 21

<210> SEQ ID NO 41
<211> LENGTH: 10
<212> TYPE: DNA
<213> ORGANISM: Artificial Sequence
<220> FEATURE:
<223> OTHER INFORMATION: Synthetic: SARS-CoV-2 ORF8 DNA Probe
<220> FEATURE:
<221> NAME/KEY: misc_feature
<223> OTHER INFORMATION: 5' Azido-Coumarin-

<400> SEQUENCE: 41
ttttctagct 10

<210> SEQ ID NO 42
<211> LENGTH: 22
<212> TYPE: DNA
<213> ORGANISM: Artificial Sequence
<220> FEATURE:
<223> OTHER INFORMATION: Synthetic: SARS-CoV-2 Spike DNA Probe

<400> SEQUENCE: 42
tgataactag cgcatatacc tg 22

<210> SEQ ID NO 43
<211> LENGTH: 8
<212> TYPE: DNA
<213> ORGANISM: Artificial Sequence -continued

```
<220> FEATURE:
<223> OTHER INFORMATION: Synthetic: SARS-CoV-2 Spike DNA Probe

<400> SEQUENCE: 43

ccaatggg                                                              8


<210> SEQ ID NO 44
<211> LENGTH: 21
<212> TYPE: DNA
<213> ORGANISM: Artificial Sequence
<220> FEATURE:
<223> OTHER INFORMATION: Synthetic: SARS-CoV-2 ORF8 DNA Probe

<400> SEQUENCE: 44

cacaattcaa ttaaaggtgc t                                              21


<210> SEQ ID NO 45
<211> LENGTH: 10
<212> TYPE: DNA
<213> ORGANISM: Artificial Sequence
<220> FEATURE:
<223> OTHER INFORMATION: Synthetic: SARS-CoV-2 ORF8 DNA Probe

<400> SEQUENCE: 45

ttttctagct                                                           10
```